(12) United States Patent
Li et al.

(10) Patent No.: US 9,321,809 B2
(45) Date of Patent: Apr. 26, 2016

(54) MACROCYCLIC COMPOUNDS FOR SUPPRESSING REPLICATION OF HEPATITIS C VIRUS

(71) Applicant: Ginkgo Pharma Co., Ltd., Suzhou, Jiangsu (CN)

(72) Inventors: Ben Li, Suzhou (CN); Li Chen, Suzhou (CN); Peibing Zhai, Suzhou (CN); Tao Jiang, Suzhou (CN)

(73) Assignee: GINKGO PHARAMA CO., LTD., Suzhou (CN)

( * ) Notice: Subject to any disclaimer, the term of this patent is extended or adjusted under 35 U.S.C. 154(b) by 0 days.

(21) Appl. No.: 14/375,418

(22) PCT Filed: Dec. 5, 2012

(86) PCT No.: PCT/CN2012/085912
§ 371 (c)(1),
(2) Date: Jul. 29, 2014

(87) PCT Pub. No.: WO2013/120371
PCT Pub. Date: Aug. 22, 2013

(65) Prior Publication Data
US 2015/0031603 A1    Jan. 29, 2015

(30) Foreign Application Priority Data

Feb. 16, 2012  (CN) .......................... 2012 1 0034872

(51) Int. Cl.
| | | |
|---|---|---|
| *C07K 5/12* | (2006.01) |
| *C07K 5/103* | (2006.01) |
| *C07K 5/087* | (2006.01) |
| *C07K 5/083* | (2006.01) |
| *A61K 38/07* | (2006.01) |
| *A61K 38/08* | (2006.01) |
| *A61K 45/06* | (2006.01) |
| *C07K 7/06* | (2006.01) |
| *A61K 38/00* | (2006.01) |
| *A61K 38/55* | (2006.01) |
| *C07K 5/065* | (2006.01) |
| *C07K 5/062* | (2006.01) |

(52) U.S. Cl.
CPC ............. *C07K 5/1013* (2013.01); *A61K 38/005* (2013.01); *A61K 38/07* (2013.01); *A61K 38/08* (2013.01); *A61K 38/55* (2013.01); *A61K 45/06* (2013.01); *C07K 5/0808* (2013.01); *C07K 5/0812* (2013.01); *C07K 7/06* (2013.01); *C07K 5/06034* (2013.01); *C07K 5/06078* (2013.01)

(58) Field of Classification Search
CPC .................................... C07K 5/10; C07K 5/12
USPC .................................................. 530/317, 330
See application file for complete search history.

(56) References Cited

FOREIGN PATENT DOCUMENTS

| | | |
|---|---|---|
| WO | WO 2010033466 | 3/2010 |
| WO | WO 2011009961 | 1/2011 |

OTHER PUBLICATIONS

McCauley, John, et al., "Discovery of Vaniprevir (MK-7009), a Macrocyclic Hepatitis C Virus NS3/4a Protease Inhibitor" "J. Med. Chem," Feb. 7, 2010, vol. 53, pp. 2443-2463.

*Primary Examiner* — David Lukton
(74) *Attorney, Agent, or Firm* — Weisun Rao; Greenberg Traurig, LLP

(57) ABSTRACT

A compound as represented by Formula (I) is provided, wherein groups are defined in the description. The compound is used as HCV protease inhibitor for treating HCV infection.

19 Claims, No Drawings

MACROCYCLIC COMPOUNDS FOR SUPPRESSING REPLICATION OF HEPATITIS C VIRUS

FIELD OF THE INVENTION

The present invention relates to macrocyclic compounds, preparation methods thereof, pharmaceutical compositions or drugs thereof, and uses thereof for treating, preventing or diagnosing HCV infection.

BACKGROUND OF THE INVENTION

Hepatitis C virus (HCV) infection is the main cause of liver diseases in the world. WHO estimates that approximately 170~200 million people are infected with chronic HCV worldwide, which is about 3% of the global population, and there are about 3~4 million new patients with HCV each year. While acute HCV has relatively mild clinical manifestations, it is likely to develop chronic infection. About 50-80% of patients with acute HCV will develop chronic HCV infection or even cirrhosis and hepatocellular carcinoma. Is has been reported that o those with chronic HCV infection, the risk of cirrhosis of the liver is 10-15% within 20 years. Currently, the mortality rate of hepatitis C is rated 10th among all the diseases in the world, while it is rated 5th in China.

The current standard treatment of HCV is using a combination of pegylated interferon alpha (PEG-IFN) and ribavirin (RBV). However, based on sustained virologic response (SVR), this treatment has unsatisfying clinical effects, and the cure rate for patients with genotype 1a/1b is about 50%. Further, the current treatment requires long courses. For example, the treatment of genotype 1 needs a 48 week course. Meanwhile, significant side effects (e.g., flu like symptoms, neuropsychiatric effects and anemia) may be associated with the current combination therapy, thereby resulting in the successful cure rate to be less than 10%. Thus, there is an urgent need for more effective HCV inhibitors with a novel mechanism and lower toxicity.

The hepatitis C virus is an RNA(+) virus that belongs to the family flaviviridae. The HCV genome is approximately 9.6 kilobases (kb) encoding a polypeptide of 3009-3030 amino acids. This large polypeptide is subsequently processed into 10 proteins with different functions, including the core protein—Core, the envelope proteins—E1 and E2, nonstructural proteins—NS2, NS3 (having serine protease activities, helicase activities), NS4A, NS4B, NSSA, NSSB (having polymerase activities), and a protein with unknown function—p7 (recently found likely to be an ion channel). In the protein maturation process, the cleavage of Core, E1, E2 and p7 is achieved by host signal peptidase, while the cleavage of NS2 and NS3 is catalyzed by their own cys-proteins and the mature NS3 is responsible for the cleavage processes of the remaining proteins. (Michael P. Manns et al., Nature Reviews Drug Discovery, 6, 991-1001 (2007)).

Most NS3 protease inhibitors are competitive with the substrate for the active site of the enzyme. In the beginning, some NS3 protease inhibitors are macrocyclic peptide-based mimetics, which have not been approved and are still in clinical trials. Another type of NS3 protease inhibitors is linear peptidomimetic inhibitors that possess an α-ketoamide group serine trap warhead forming a covalent but reversible complex with the enzyme.

Currently, Telaprevir and boceprevir have been approved as NS3 protease inhibitors. However, they show low in vitro activities and poor PK properties, thereby requiring high dosages. Therefore, a main goal of HCV protease inhibitors development is to develop protease inhibitors with high potency and excellent PK properties.

SUMMARY OF THE INVENTION

One purpose of the present invention is to provide novel compounds, which inhibit HCV replication, for treatment of HCV infection. The present invention also provides novel therapeutic methods as a new option for treating HCV infection.

Another purpose of the present invention is to provide pharmaceutical compositions, characterized in that each of the compositions comprises a therapeutically effective amount of a compound of Formula (I), or a pharmaceutically acceptable salt thereof.

Still another purpose of the present invention is to provide use of a compound of Formula (I), or a pharmaceutically acceptable salt thereof, for the manufacture of a medicament for inhibition of HCV replication.

The fourth purpose of the present invention is to provide use of a compound of Formula (I), or a pharmaceutically acceptable salt thereof, for the manufacture of a medicament for prevention of infection by HCV.

In one aspect, the present invention provides a compound of Formula (I) or a pharmaceutically acceptable salt, solvent, or prodrug thereof:

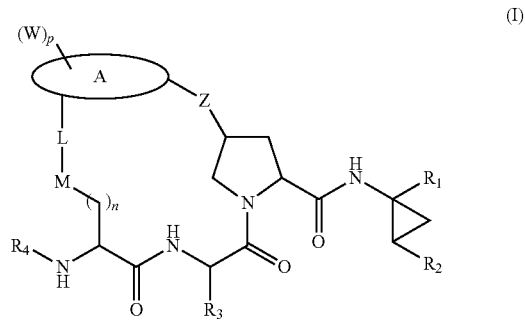

wherein
R$_1$ is CO$_2$R$_a$, —CONR$_b$SO$_2$R$_c$, —CONR$_d$SO$_2$NR$_e$R$_f$, or tetrazolyl;
R$_2$ is C$_1$-C$_6$ alkyl, C$_2$-C$_6$ alkenyl, or C$_3$-C$_8$ cycloalkyl, and said groups each are optionally substituted with 1-3 halo;
R$_3$ is C$_1$-C$_8$ alkyl, C$_3$-C$_8$ cycloalkyl, C$_1$-C$_8$ alkyl substituted with C$_3$-C$_8$ cycloalkyl, or C$_1$-C$_8$ alkyl or heteroalkyl substituted with aryl, and said groups each are optionally substituted with 1-3 halo;
R$_4$ is H, C$_1$-C$_6$ alkyl, —SO$_2$R$_c$, —SO$_2$NR$_d$R$_e$, —CONR$_f$R$_g$, —COOR$_h$, or —COR$_i$;
n is 1 or 2;
p is 0, 1, or 2;
M is —O—, —S— or —NH—;
L is C$_1$-C$_6$ alkylene, C$_2$-C$_6$ alkenyl, or C$_2$-C$_6$ alkynyl;
W is halo, hydroxyl, NO$_2$, CN, CF$_3$, OCF$_3$, —NR$_a$R$_b$, —SO$_2$R$_c$, —SOR$_c$, —SR$_c$, —SO$_2$NR$_d$R$_e$, —CONR$_f$R$_g$, —COOR$_h$, —NR$_i$COR$_j$, —NR$_k$SO$_2$R$_l$, C$_1$-C$_6$ alkyl, —O—C$_1$-C$_6$ alkyl, C$_3$-C$_7$ cycloalkyl, aryl, or heteroaryl;
Z is C$_1$-C$_6$ alkylene, —O—, —O—C$_1$-C$_5$ alkylene, —C(O)O—, C$_1$-C$_5$ alkylene-C(O)O—, —C(O)NR$_a$R$_b$—, or C$_1$-C$_5$ alkylene-C(O)NR$_a$R$_b$—;
ring A is an 8-14 membered fused bicyclic or tricyclic carbon structure, optionally substituted with 1-4 N, O, or S heteroatoms;

each of $R_a$, $R_b$, $R_c$, $R_d$, $R_e$, $R_f$, $R_g$, $R_h$, $R_i$, $R_j$, $R_k$, $R_l$ is independently H, $C_1$-$C_6$ alkyl, $C_3$-$C_7$ cycloalkyl, $C_5$-$C_{10}$ aryl or heteroaryl, or $C_1$-$C_6$ alkylene $C_5$-$C_{10}$ aryl or heteroaryl.

In another embodiment, the compounds provided by the present invention have Formula (IIa):

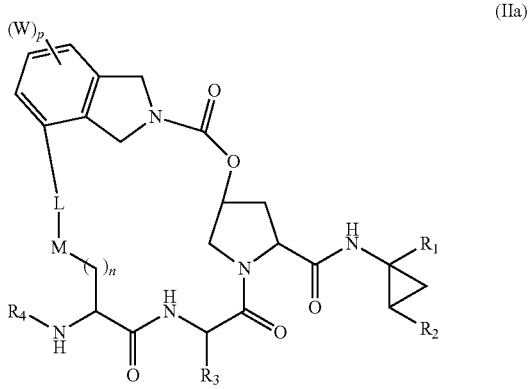

(IIa)

In another embodiment, the compounds provided by the present invention have Formula (IIb)

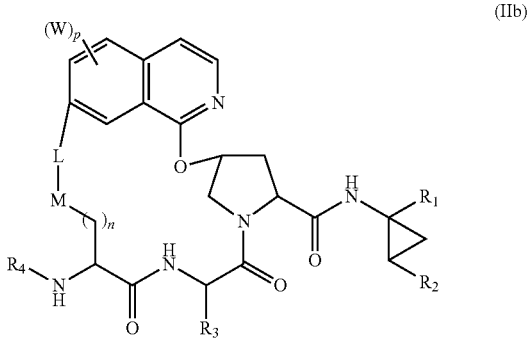

(IIb)

In a second aspect, the present invention provides a pharmaceutical composition comprising a pharmaceutically acceptable carrier and a compound of Formula (I) or a pharmaceutically acceptable salt, solvent, or prodrug thereof.

Preferably, said pharmaceutical composition further comprises a second therapeutic agent selected from the group consisting of an HCV antiviral agent, an immunomodulator, and an anti-infective agent; wherein the HCV antiviral agent is selected from an HCV protease inhibitor and an HCV NS5B polymerase inhibitor.

In one embodiment, the pharmaceutical composition may be formulated, for example, by employing aqueous dispersions, liquid, gels, syrups, elixirs, slurries, suspensions, sprays, controlled-release formulations, instantizing agents, effervescing agents, lyophilized agents, tablets, powders, pills, dragees, capsules, relayed release preparations, sustained-release dosages, pulsed release tablets, microgranules, or immediate release agents.

In a third aspect, the present invention provides a use of a compound of Formula (I), or a pharmaceutically acceptable salt, solvent, or prodrug thereof, for the manufacture of a medicament for prevention or treatment of infection by HCV.

Thus, the present invention provides anti-HCV virus compounds with high potency and excellent PK properties.

DETAILED DESCRIPTION OF THE INVENTION

After intensive and extensive study, the inventors discovered a kind of macrocyclic compounds that can effectively inhibit HCV.

Compounds

In one aspect, the present invention provides a compound of Formula (I) or a pharmaceutically acceptable salt, solvent, or prodrug thereof:

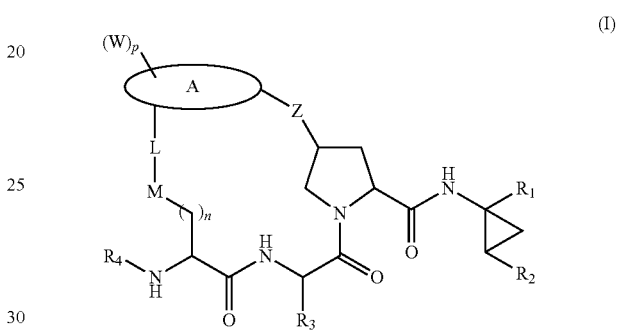

(I)

wherein $R_1$ is $CO_2R_a$, —$CONR_bSO_2R_c$, —$CONR_dSO_2NR_eR_f$, or tetrazolyl;

$R_2$ is $C_1$-$C_6$ alkyl, $C_2$-$C_6$ alkenyl, or $C_3$-$C_8$ cycloalkyl, and said groups each are optionally substituted with 1-3 halo;

$R_3$ is $C_1$-$C_8$ alkyl, $C_3$-$C_8$ cycloalkyl, $C_1$-$C_8$ alkyl substituted with $C_3$-$C_5$ cycloalkyl, or $C_1$-$C_8$ alkyl or heteroalkyl substituted with aryl, and said groups each are optionally substituted with 1-3 halo;

$R_4$ is H, $C_1$-$C_6$ alkyl, —$SO_2R_c$, —$SO_2NR_dR_e$, —$CONR_fR_g$, —$COOR_h$, or —$COR_i$;

n is 1 or 2;

p is 0, 1 or 2;

M is —O—, —S— or —NH—;

L is $C_1$-$C_6$ alkylene, $C_2$-$C_6$ alkenyl or $C_2$-$C_6$ alkynyl;

W is halo, hydroxyl, $NO_2$, CN, $CF_3$, $OCF_3$, —$NR_aR_b$, —$SO_2R_c$, —$SOR_c$, —$SR_c$, —$SO_2NR_dR_e$, —$CONR_fR_g$, —$COOR_h$, —$NR_iCOR_j$, —$NR_kSO_2R_l$, $C_1$-$C_6$ alkyl, —O—$C_1$-$C_6$ alkyl, $C_3$-$C_7$ cycloalkyl, aryl or heteroaryl;

Z is $C_1$-$C_6$ alkylene, —O—, —O—$C_1$-$C_5$ alkylene, —C(O)O—, $C_1$-$C_5$ alkylene-C(O)O—, —C(O)$NR_aR_b$— or $C_1$-$C_5$ alkylene-C(O)$NR_aR_b$—;

ring A is a 8-14 membered fused bicyclic or tricyclic carbon structure, optionally substituted with 1-4 N, O, or S heteroatoms;

each $R_a$, $R_b$, $R_c$, $R_d$, $R_e$, $R_f$, $R_g$, $R_h$, $R_i$, $R_j$, $R_k$, $R_l$ is independently selected from H, $C_1$-$C_6$ alkyl, $C_3$-$C_7$ cycloalkyl, $C_5$-$C_{10}$ aryl or heteroaryl.

In an aspect of the present invention, $R_1$ is —$CONR_bSO_2R_c$ and/or $R_4$ is —$COOR_h$;

In an aspect the present invention, the compounds of Formula (I) have Formula (IIa):

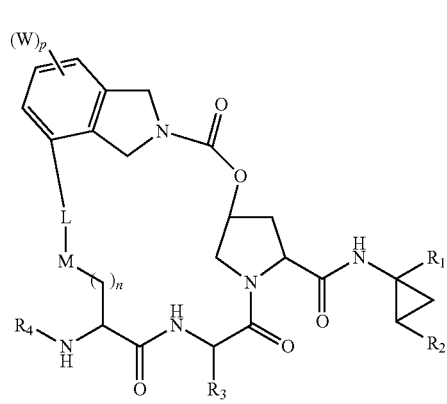

(IIa)

wherein $R_1$, $R_2$, $R_3$, $R_4$, n, p, M, L and W are defined as above.

In an aspect of the present invention, the compounds of Formula (I) have Formula (IIb):

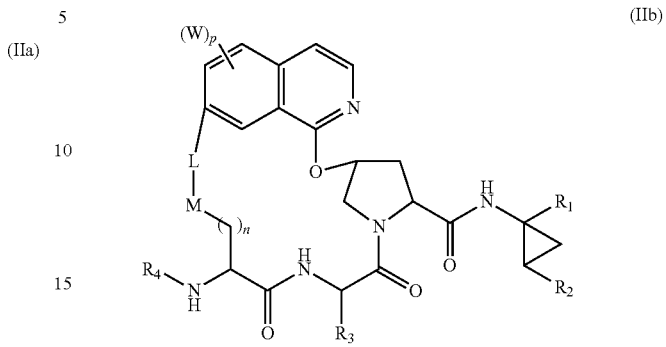

(IIb)

wherein $R_1$, $R_2$, $R_3$, $R_4$, n, p, M, L and W are defined as above.

Any combination of the variables as described above can be expected.

In a preferred embodiment, the compound of formula (IIa) includes, but not limited to, the compounds showed in Table 1.

TABLE 1

| Number | Structure | Name |
|---|---|---|
| IIa-1 | | tert-butyl N-[(1R,12E,17S,20S, 23S)-20-tert-butyl-23-{[(1R,2S)-1-[(cyclopropanesulfonyl) carbamoyl]-2-ethenylcyclopropyl] carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate |
| IIa-2 | | (1R,12E,17S,20S,23S)-17-amino-20-tert-butyl-N-[(1R,2S)-1-[(cyclopropanesulfonyl) carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide |

TABLE 1-continued

| Number | Structure | Name |
|---|---|---|
| IIa-3 | | tert-butyl N-[(1R,12E,17R,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl] carbamate |
| IIa-4 | | (1R,12E,17R,20S,23S)-17-amino-20-tert-butyl-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide |
| IIa-5 | | (1R,12E,17S,20S,23S)-20-tert-butyl-23-N-[(1R,2S)-1-[(cyclopropanesulfonyl)carbamoyl]-2-ethenylcyclopropyl]-3,18,21-trioxo-17-C-pyrazine-2-2,15-dioxa-4,19,22-triazatetracyclo[20.2.1.1$^{4,7}$.0$^{6,11}$]hexacosa-6,8,10,12-tetraene-17,23-diamido |
| IIa-6 | | (1R,12E,17R,20S,23S)-20-tert-butyl-23-N-[(1R,2S)-1-[(cyclopropanesulfonyl)carbamoyl]-2-ethenylcyclopropyl]-3,18,21-trioxo-17-C-pyrazine-2-2,15-dioxa-4,19,22-triazatetracyclo[20.2.1.1$^{4,7}$.0$^{6,11}$]hexacosa-6,8,10,12-tetraene-17,23-diamido |

TABLE 1-continued

| Number | Structure | Name |
|---|---|---|
| IIa-7 | | (1R,12E,17S,20S,23S)-20-tert-butyl-N-[(1R,2S)-1-[(cyclopropanesulfonyl)carbamoyl]-2-ethenylcyclopropyl]-17-acetamido-3,18,21-trioxo-2,15-dioxa-4,19,22-triazatetracyclo[20.2.1.1$^{4,7}$.0$^{6,11}$]hexacosa-6,8,10,12-tetraene-23-carboxamide |
| IIa-8 | | (1R,12E,17S,20S,23S)-20-tert-butyl-N-[(1R,2S)-1-[(cyclopropanesulfonyl)carbamoyl]-2-ethenylcyclopropyl]-17-methanesulfonamido-3,18,21-trioxo-2,15-dioxa-4,19,22-triazatetracyclo[20.2.1.1$^{4,7}$.0$^{6,11}$]hexacosa-6,8,10,12-tetraene-23-carboxamide |
| IIa-9 | | ethyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate |
| IIa-10 | | benzyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate |

TABLE 1-continued

| Number | Structure | Name |
|---|---|---|
| IIa-11 | | cyclopentyl N-[(1R,12E,17S,20S, 23S)-20-tert-butyl-23-{[(1R,2S)-1-[(cyclopropanesulfonyl) carbamoyl]-2-ethenylcyclopropyl] carbamoyl}-3,18,21-trioxo-2,15-dioxa-4,19,22-triazatetracyclo [20.2.1.1$^{4,7}$.0$^{6,11}$]hexacosa-6,8,10,12-tetraen-17-yl]carbamate |
| IIa-12 | | (1R,12E,17S,20S,23S)-20-tert-butyl-17-[(tert-butylcarbamoyl) amino]-N-[(1R,2S)-1-[(cyclopropanesulfonyl) carbamoyl]-2-ethenylcyclopropyl]-3,18,21-trioxo-2,15-dioxa-4,19,22-triazatetracyclo[20.2.1.1$^{4,7}$.0$^{6,11}$] hexacosa-6,8,10,12-tetraene-23-carboxamide |
| IIa-13 | | tert-butyl N-[(1R,17S,20S,23S)-20-tert-butyl-23-{[(1R,2S)-1-[(cyclopropanesulfonyl) carbamoyl]-2-ethenylcyclopropyl] carbamoyl}-3,18,21-trioxo-2,15-dioxa-4,19,22-triazatetracyclo [20.2.1.1$^{4,7}$.0$^{6,11}$]hexacosa-6,8,10-trien-17-yl]carbamate |
| IIa-14 | | tert-butyl N-[(1R,17S,20S,23S)-20-tert-butyl-23-{[(1R,2R)-1-[(cyclopropanesulfonyl) carbamoyl]-2-ethylcyclopropyl] carbamoyl}-3,18,21-trioxo-2,15-dioxa-4,19,22-triazatetracyclo [20.2.1.1$^{4,7}$.0$^{6,11}$]hexacosa-6,8,10-trien-17-yl]carbamate |

TABLE 1-continued

| Number | Structure | Name |
|---|---|---|
| IIa-15 | | tert-butyl N-[(1R,12E,17S,20S, 23S)-20-tert-butyl-23-{[(1R,2R)-1-[(cyclopropanesulfonyl) carbamoyl]-2-ethylcyclopropyl] carbamoyl}-3,18,21-trioxo-2,15-dioxa-4,19,22-triazatetracyclo [20.2.1.1$^{4,7}$.0$^{6,11}$]hexacosa-6,8,10,12-tetraen-17-yl]carbamate |
| IIa-16 | | tert-butyl N-[(1R,12E,17S,20S, 23S)-20-cyclohexyl-23-{[(1R,2S)-1-[(cyclopropanesulfonyl) carbamoyl]-2-ethenylcyclopropyl] carbamoyl}-3,18,21-trioxo-2,15-dioxa-4,19,22-triazatetracyclo [20.2.1.1$^{4,7}$.0$^{6,11}$]hexacosa-6,8,10,12-tetraen-17-yl]carbamate |
| IIa-17 | | tert-butyl N-[(1R,17S,20S,23S)-20-cyclohexyl-23-{[(1R,2S)-1-[(cyclopropanesulfonyl) carbamoyl]-2-ethenylcyclopropyl] carbamoyl}-3,18,21-trioxo-2,15-dioxa-4,19,22-triazatetracyclo [20.2.1.1$^{4,7}$.0$^{6,11}$]hexacosa-6,8,10-trien-17-yl]carbamate |

TABLE 1-continued

| Number | Name |
|---|---|
| IIa-18 | tert-butyl N-[(1R,17S,20S,23S)-20-cyclohexyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate |
| IIa-19 | tert-butyl N-[(1R,12E,17S,20S,23S)-20-cyclohexyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate |
| IIa-20 | tert-butyl N-[(1R,12E,18S,21S,24S)-21-cyclohexyl-24-{[(1R,2S)-1-[(cyclopropanesulfonyl)carbamoyl]-2-ethenylcyclopropyl]carbamoyl}-3,19,22-trioxo-2,15-dioxa-4,20,23-triazatetracyclo[21.2.1.1$^{4,7}$.0$^{6,11}$]heptacosa-6,8,10,12-tetraen-18-yl]carbamate |

TABLE 1-continued

| Number | Sructure | Name |
|---|---|---|
| IIa-21 | | tert-butyl N-[(1R,12E,17R,20S,23S)-20-tert-butyl-23-{[(1R,2S)-1-[(cyclopropanesulfonyl)carbamoyl]-2-ethenylcyclopropyl]carbamoyl}-3,18,21-trioxo-2-oxa-15-thia-4,19,22-triazatetracyclo[20.2.1.1$^{4,7}$.0$^{6,11}$]hexacosa-6,8,10,12-tetraen-17-yl]carbamate |
| IIa-22 | | tert-butyl N-[(1R,12E,17S,20S,23S)-20-cyclopentyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate |

The compounds of Formula (IIb) include, but are not limited to, the following compounds in Table 2.

TABLE 2

| Number | Structure | Name |
|---|---|---|
| IIb-1 | 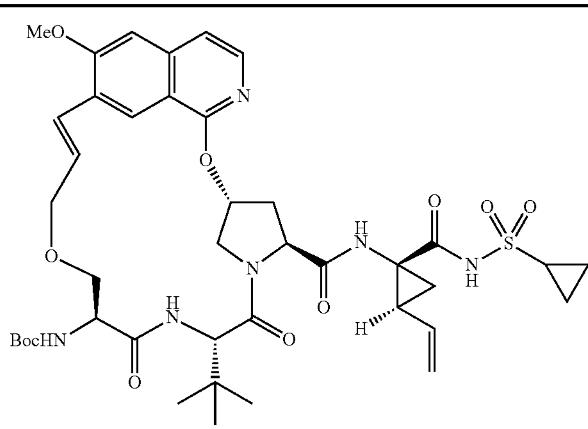 | tert-butyl N-[(3R,5S,8S,11S,15E)-8-tert-butyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),15,17(25),18,20(24),21-hexaen-11-yl]carbamate |

TABLE 2-continued

| Number | Structure | Name |
|---|---|---|
| IIb-2 | 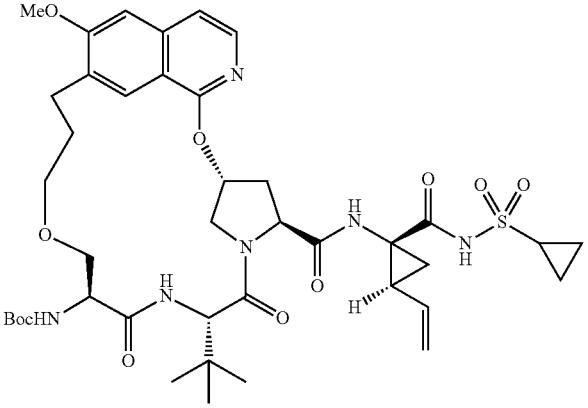 [SMILES: C=C[C@@H]1C[C@]1(NC(=O)[C@@H]1C[C@@H]2CN1C(=O)[C@H](C(C)(C)C)NC(=O)[C@@H](NC(=O)OC(C)(C)C)COCCCc1cc3c(nccc3cc1OC)O2)C(=O)NS(=O)(=O)C1CC1] | tert-butyl N-[(3R,5S,8S,11S)-8-tert-butyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),17(25),18,20(24),21-pentaen-11-yl]carbamate |
| IIb-3 | 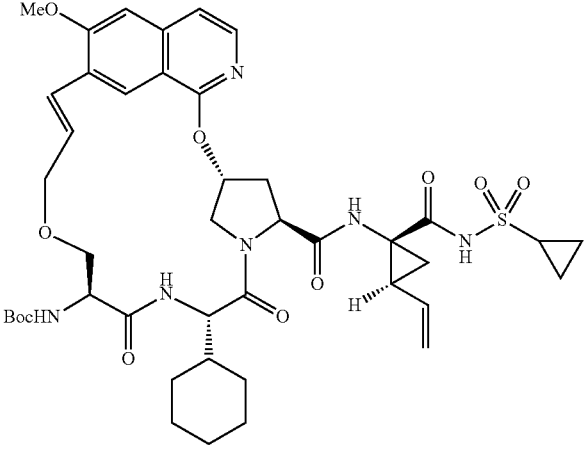 [SMILES: C=C[C@@H]1C[C@]1(NC(=O)[C@@H]1C[C@@H]2CN1C(=O)[C@H](C1CCCCC1)NC(=O)[C@@H](NC(=O)OC(C)(C)C)COC/C=C/c1cc3c(nccc3cc1OC)O2)C(=O)NS(=O)(=O)C1CC1] | tert-butyl N-[(3R,5S,8S,11S,15E)-8-cyclohexyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),15,17(25),18,20(24),21-hexaen-11-yl]carbamate |
| IIb-4 | 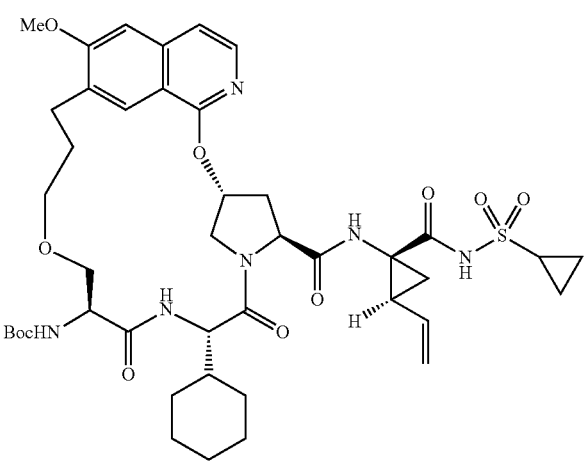 [SMILES: C=C[C@@H]1C[C@]1(NC(=O)[C@@H]1C[C@@H]2CN1C(=O)[C@H](C1CCCCC1)NC(=O)[C@@H](NC(=O)OC(C)(C)C)COCCCc1cc3c(nccc3cc1OC)O2)C(=O)NS(=O)(=O)C1CC1] | tert-butyl N-[(3R,5S,8S,11S)-8-cyclohexyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),17(25),18,20(24),21-pentaen-11-yl]carbamate |

TABLE 2-continued

| Number | Structure | Name |
|---|---|---|
| IIb-5 | 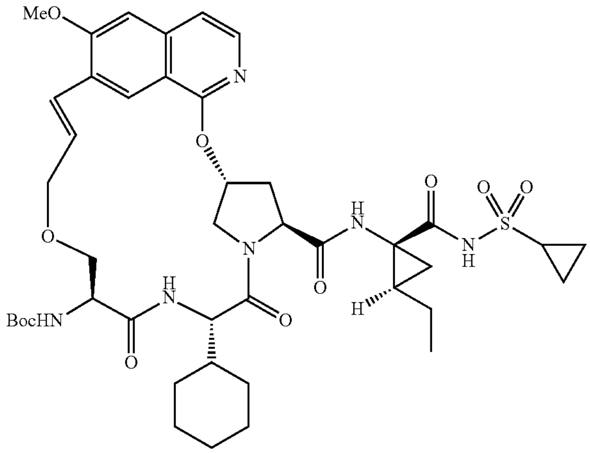 [SMILES: CC[C@@H]1C[C@]1(NC(=O)[C@@H]1C[C@@H]2CN1C(=O)[C@H](C1CCCCC1)NC(=O)[C@@H](NC(=O)OC(C)(C)C)COC/C=C/c1cc3c(nccc3cc1OC)O2)C(=O)NS(=O)(=O)C1CC1] | tert-butyl N-[(3R,5S,8S,11S,15E)-8-cyclohexyl-5-{[(1R,2R)-1-[(cyclopropanesulfonyl)carbamoyl]-2-ethylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),15,17(25),18,20(24),21-hexaen-11-yl]carbamate |
| IIb-6 | 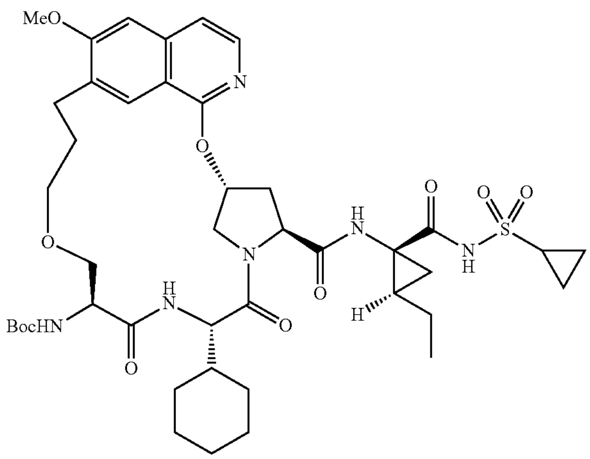 [SMILES: CC[C@@H]1C[C@]1(NC(=O)[C@@H]1C[C@@H]2CN1C(=O)[C@H](C1CCCCC1)NC(=O)[C@@H](NC(=O)OC(C)(C)C)COCCCc1cc3c(nccc3cc1OC)O2)C(=O)NS(=O)(=O)C1CC1] | tert-butyl N-[(3R,5S,8S,11S)-8-cyclohexyl-5-{[(1R,2S)-1-[(cyclopropanesulfonyl)carbamoyl]-2-ethylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),17(25),18,20(24),21-pentaen-11-yl]carbamate |
| IIb-7 | 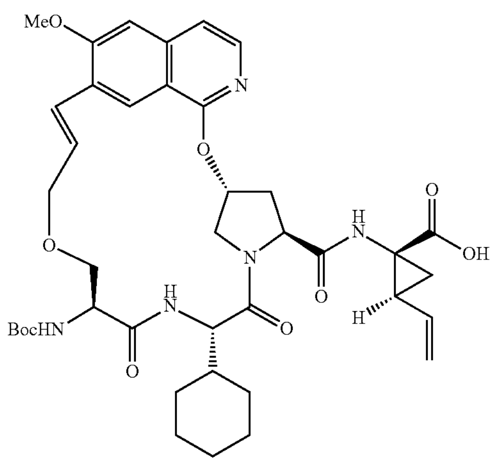 [SMILES: C=C[C@@H]1C[C@]1(NC(=O)[C@@H]1C[C@@H]2CN1C(=O)[C@H](C1CCCCC1)NC(=O)[C@@H](NC(=O)OC(C)(C)C)COC/C=C/c1cc3c(nccc3cc1OC)O2)C(=O)O] | (1R,2S)-1-[(3R,5S,8S,11S,15E)-11-{[(tert-butoxy)carbonyl]amino}-8-cyclohexyl-18-methoxy-7,10-dioxo-2,13-dioxa-6,9,23-triazatetracyclo[15.6.2.1$^{3,6}$.0$^{20,24}$]hexacosa-1(23),15,17(25),18,20(24),21-hexaene-5-amido]-2-ethenylcyclopropane-1-carboxylic acid |

Synthesis of Compounds

The compounds of Formula (I) as described above can be synthesized using standard techniques known in the art or in conjunction with the text method of synthesis. Further, the solvent, temperature and other reaction conditions as mentioned herein may be changed.

For synthesis of the compounds of Formula (I), the starting material can be synthesized or obtained from commercial sources on, such as, but not limited to, Aldrich Chemical Co. (Milwaukee, Wis.) Or Sigma Chemical Co. (St. Louis, Mo.). Other compounds described herein having different substituents and related compounds can be synthesized using standard techniques and materials known in the art, which include the methodology described in March, Advanced Organic Chemistry 4th Ed. (Wiley 1992); Carey and Sundherg, Advanced Organic Chemistry 4th Ed.; Vols. A and B (Plenum 2000, 2001); Green and Wuts, Protective Groups in Organic Synthesis 3rd Ed., (Wiley 1999). The general method of preparation of compounds can use appropriate reagents or introduce various groups into the formula.

Synthesis of Compounds of Formula IIa by Scheme I

Scheme I: Synthesis of left macrocyclic fragment A9

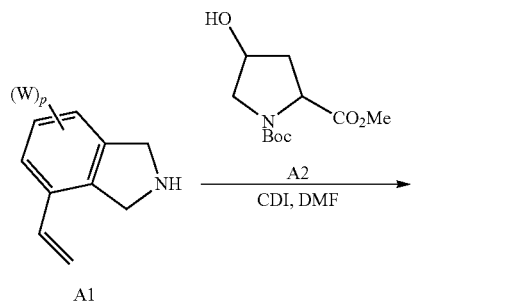

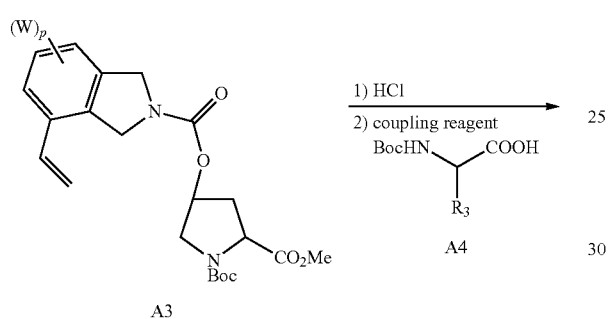

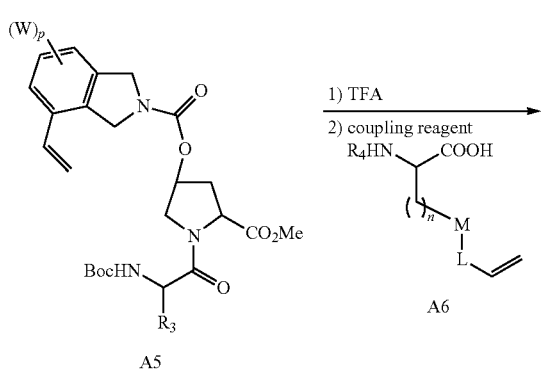

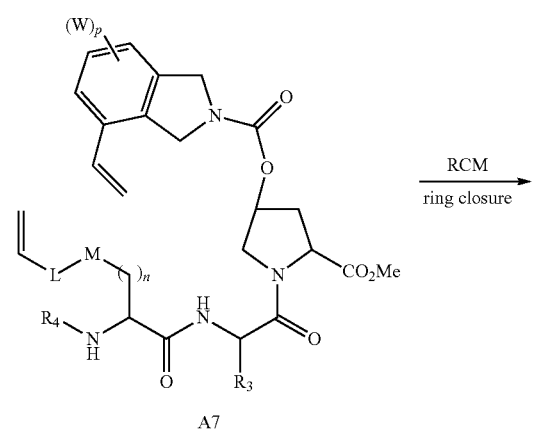

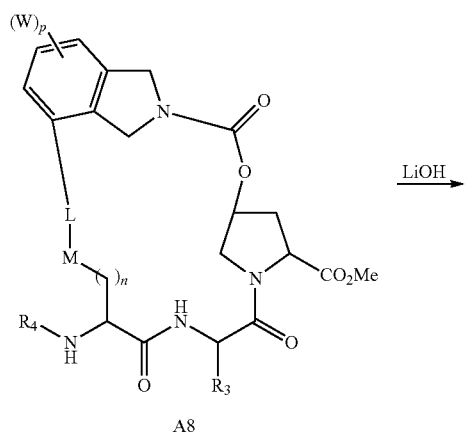

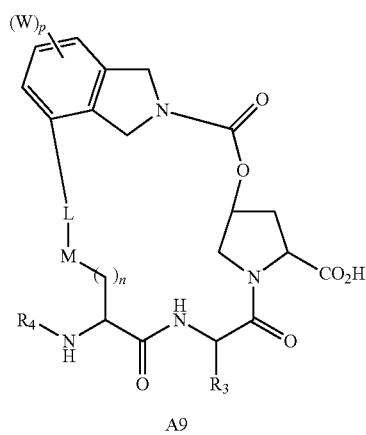

A condensation reaction between an alkenyl substituted isoindoline A1 and a protected 4-hydroxyproline methyl ester A2 took place to give carbamate A3. After removal of the protected group Boc, the resulting compound was coupled with amine acid A4 to give dipeptide A5. The intermediate A5 can be deprotected, then reacted with A6 (by condensation) to give bis olefin A7. A7 is macrocyclized by ring closing metathesis to give compound A8. Then, A8 is hydrolyzed to give macrocyclic fragment A9.

Synthesis of Compounds of Formula IIb by Scheme II

Scheme II: Synthesis of left macrocyclic fragment B7

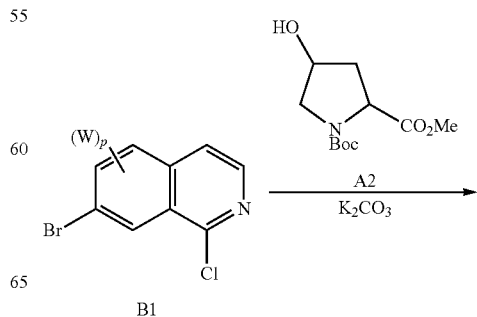

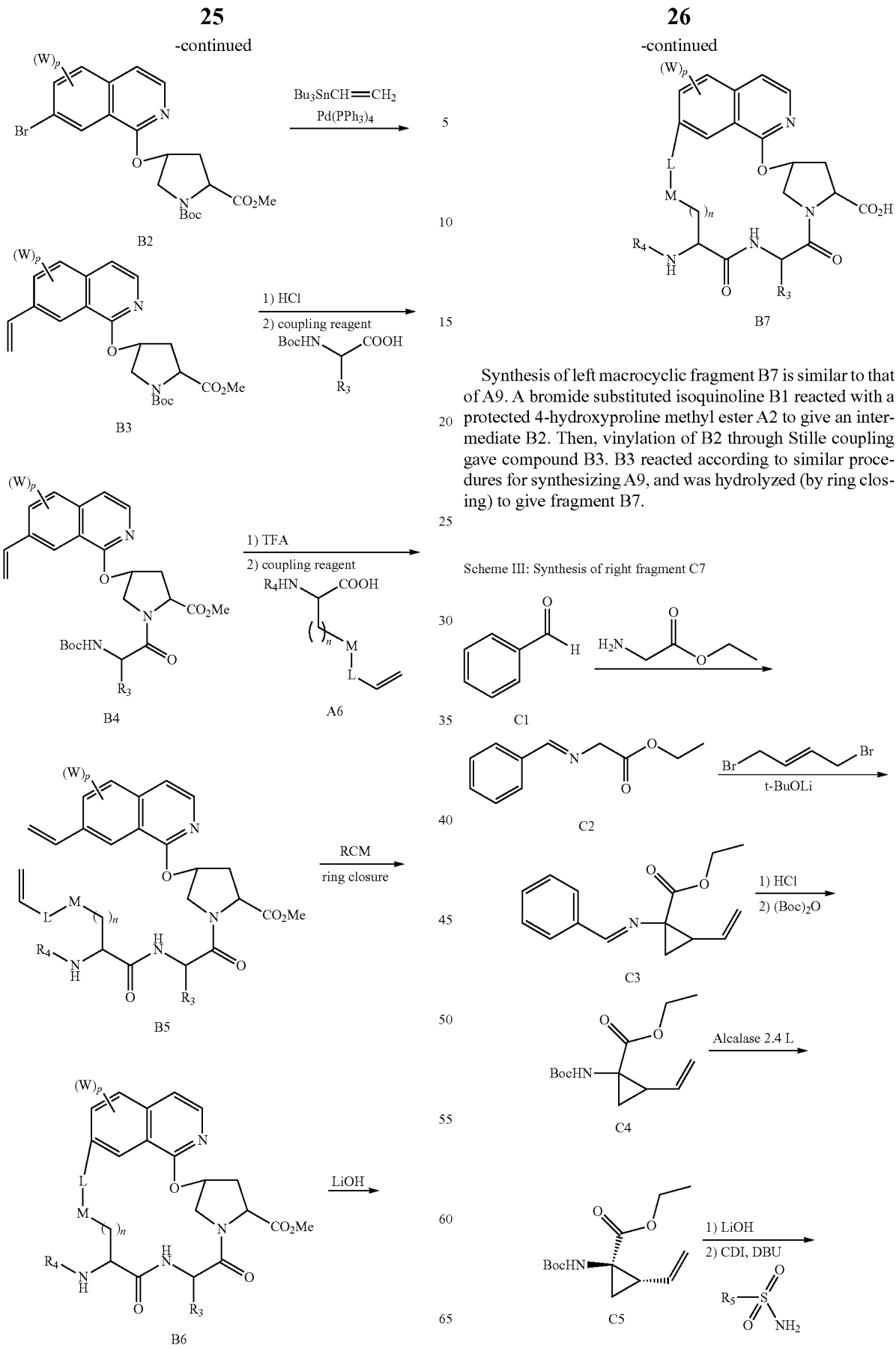

Synthesis of left macrocyclic fragment B7 is similar to that of A9. A bromide substituted isoquinoline B1 reacted with a protected 4-hydroxyproline methyl ester A2 to give an intermediate B2. Then, vinylation of B2 through Stille coupling gave compound B3. B3 reacted according to similar procedures for synthesizing A9, and was hydrolyzed (by ring closing) to give fragment B7.

Scheme III: Synthesis of right fragment C7

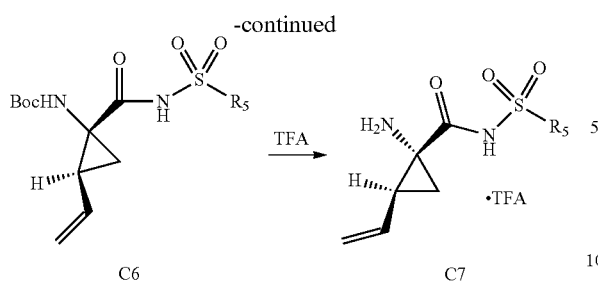

According to the reference (J. Org. Chem. 2005, 70, 5869-5879), benzaldehyde was mixed with ethyl glycinate and dehydrated to give imine C2. Then, a base was added, C2 reacted with trans-1,4-dibromo-2-butene and a base to give major trans cyclopropyl derivative C3. An Acid was added to remove benzyl to give racemic C4. The enzymatic resolution of vinyl-ACCA ester C4 affords optically pure (1R,2S) ethyl ester C5. C5 was hydrolyzed with LiOH, and condensated with sulfonamide to give intermediate C6. Then CF3 was used to remove Boc group to give the right fragment C7.

Scheme IV: Synthesis of compounds of Formula IIa

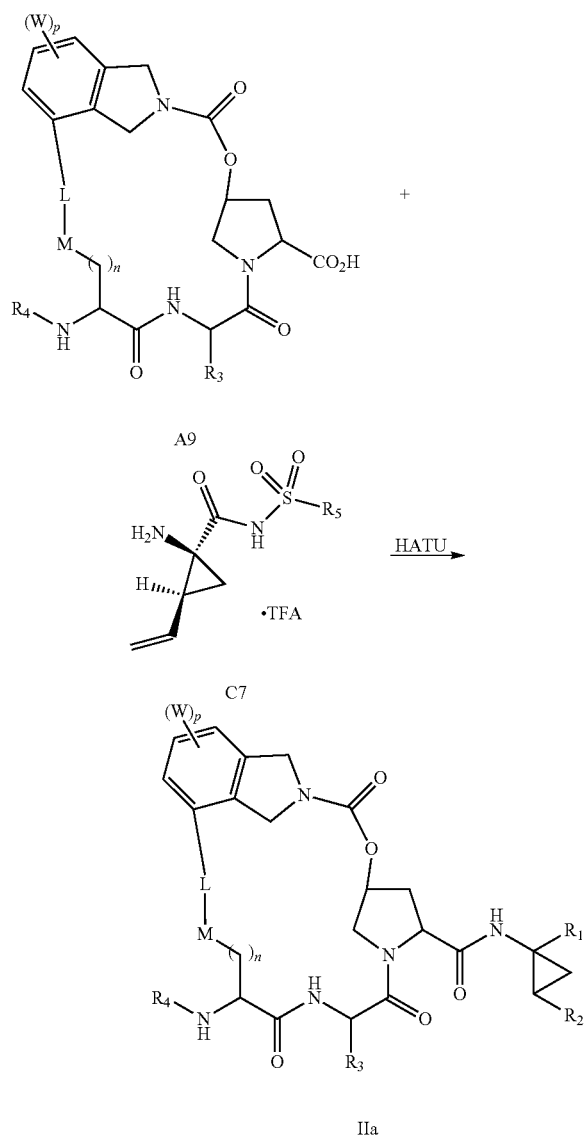

The left macrocyclic fragment A9 was coupled with amine C7 to give a compound of formula IIa. Optionally, a further hydrogenation or addition of the compound IIa may take place to give analogues of compound IIa.

Scheme V: Synthesis of compounds of Formula IIb

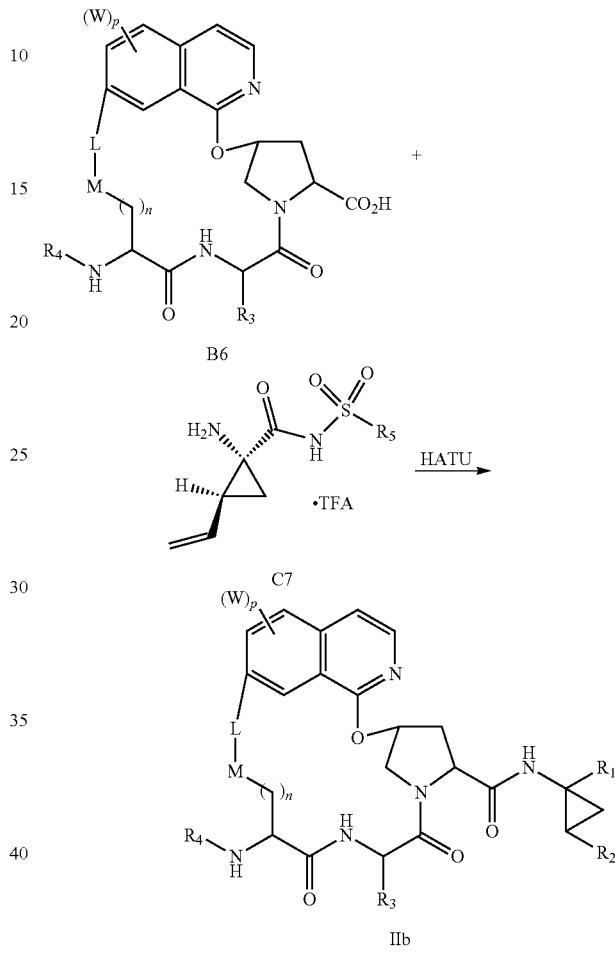

The left macrocyclic fragment B6 can be coupled with amine C7 to give a compound of formula IIb. Optionally, a further hydrogenation or addition of the compound IIb may take place to give analogues of compound IIb.

Further Forms of Compounds

It should be clear that some of the compounds of Formula (I) may be present tautomerism. The compounds of Formula (I) can exist in either unsolvated or solvated. In some embodiments of the present invention, the compounds of Formula (I) may exist polymorphism.

The compounds of Formula (I) may be administered in the form of pharmaceutically acceptable salts which are derived from acids or bases. Examples of the salts include, but are not limited to, those derived from inorganic acids such as hydrochloric acid, sulfuric acid, nitric acid, phosphoric acid and the like; and the salts prepared from organic acids such as acetic acid, oxalic acid, succinic acid, tartaric acid, methanesulfonic acid, maleic acid and the like. Examples of the other salt include a salt with alkali metal or alkaline earth metal (e.g., sodium, potassium calcium, magnesium). Examples of the salts also include other pharmaceutically acceptable salts, which the active ingredient are converted into in vivo when administered in free form. Examples of the prodrug of the compound of Formula (I) include ester, carbamate and other conventional forms, which are converted into the active ingredient in vivo when administered in this form.

THE TERMS

If not otherwise stated, the terms in the present application, including the specification and claims, are defined as follows. It is noted that, in the specification and appended claims, if the text without another clear indication, the singular forms "a" include plural significance. If not otherwise stated, conventional methods of mass spectrometry, NMR, HPLC, protein chemistry, biochemistry, recombinant DNA technology and pharmacology are used herein. In the present application, if not otherwise stated, the use of "or" or "and" means "and/or".

As used herein, the term "compound of Formula (I)" refers to a compound of Formula (I), (IIa), (IIb).

As used herein, the term "alkyl" includes both branched and straight-chain saturated aliphatic hydrocarbon groups having 1-8, preferably 1-6 carbon atoms. $C_{1-n}$ alkyl refers to both branched and straight-chain saturated aliphatic hydrocarbon groups having 1-n carbon atoms. ("$C_{1-20}$" represents branched or straight-chain saturated aliphatic hydrocarbon groups having 1-20 carbon atoms, which can be from 1 carbon atom, 2 carbon atoms, 3 carbon atoms, and so on up to and including 20 carbon atoms. 1-20 restrictions which do not include a substituted alkyl group carbon atoms, such as substituted alkylamino "alkyl", when not particularly limited the number of carbon atoms, which refers only to the alkyl portion of the specified 1-20 carbon atoms, and does not include a substituent on the alkyl carbon atoms and other substituents on the amino group which has a carbon atom number. The use of "$C_{1-8}$ alkyl" indicates that the formulation containing alkyl group of 1 to 8 carbon atoms.) As used herein, the term "alkenyl" includes straight or branched hydrocarbon groups having at least one carbon-carbon double bond and 2-8 (preferably 2-6) carbon atoms. As used herein, the term "alkynyl" includes straight or branched hydrocarbon groups having at least one carbon-carbon triple bond and 2-8 (preferably 2-6) carbon atoms. The term "haloalkyl" includes the alkyl containing one or more halo groups, wherein alkyl is described as above. $C_{1-8}$ haloalkyl represents the alkyl having 1-8 carbon atoms. Haloalkyl refers to the alkyl group wherein the H atom is substituted with halogen atom. For example, a perfluoroalkyl group is an alkyl wherein all of the H atoms are substituted by F.

The term "aralkyl group" refers to an aryl group-substituted alkyl, wherein alkyl and aryl are defined as in the invention.

As used herein, the term "aryl" refers to aromatic system and may be monocyclic or polycyclic aryl group fused together or attached together, thus making at least a portion of fused or attached rings forming conjugated aromatic system. Examples of aryl groups include, but are not limited to, phenyl, naphthyl or tetrohydronaphthyl (tetralin). The aryl groups are optionally substituted with 1-4 groups, wherein said group is selected from halo, cyano, hydroxy, nitro, amino, alkyl, cycloalkyl, alkenyl, alkynyl, alkoxy, aryloxy, substituted alkoxy, alkylcarbonyl, alkylcarboxy, alkylamino or arylthiol. Preferred substituents are halo and $C_{1-4}$ alkyl.

The term "cycloalkyl" means a non-aromatic monocyclic or polycyclic aromatic group, form a ring in which each atom (i.e., backbone atoms) is a carbon atom. Cycloalkyl group may be saturated or partially unsaturated. Cycloalkyl may be fused to an aromatic ring wherein the link place is not at the carbon atom of aryl group. Cycloalkyl group has 3 to 10 ring atoms. Carbocyclic alkyl groups include, but are not limited to cyclopropyl, cyclobutyl, cyclopentyl, cyclohexyl, cycloheptyl and cyclooctyl. Cycloalkyl is optionally substituted or unsubstituted.

As used herein, the term "halo" or "halogen" refers to fluorine (fluoro), chlorine (chloro), bromine (bromo) or iodine (iodo).

The term "heterocycloalkyl" means those cyclic group containing N, O, S heteroatoms and consisting of 3 to 8 ring atoms. In the group, the hetero atoms may include only N, or also O or S. The number of hetero atoms may be one, or more than one. The heterocyclic ring may be saturated or unsaturated. More specifically, the term nitrogen-containing heterocyclic groups include, but are not limited to, pyrrolyl, tetrahydro-pyrrolyl, piperidinyl, piperazinyl, morpholinyl, piperazinyl, pyrimidinyl, imidazolyl group and the like.

The term "bond" or "single bond" refers to a fragment between the two or between two atoms (as atoms connected by a key to be considered part of the overall structure) of the bond. In one aspect, described herein, when a group key, the reference group is missing, allowing the determination of the residual between the groups form a bond.

As used herein, the term "ring (membered ring)" can contain an arbitrary ring structure. The term "element" is used to indicate the ring skeleton composed of the number of atoms. Thus, for example, cyclohexyl, pyridine, pyran and thiopyran ring of six, and cyclopentyl, pyrrole, furan and thiophene ring of five.

As used herein, the term "fragment" refers to a particular part of the molecule or functional group, generally considered to be the chemical fragment contained in or attached to the molecule chemical entities.

The term "optionally substituted" or "substituted" means that a group may be substituted with additional groups each individually and independently selected from alkyl, cycloalkyl, aryl, heteroaryl, heteroalkyl, hydroxy, alkylthio, arylthio, alkylsulfinyl, arylsulfinyl, alkylsulfonyl, arylsulfonyl, a cyano group, halogen, a carbonyl group, nitro, haloalkyl, fluoroalkyl, amino (including mono- and di-substituted amino group, and protected derivatives thereof). For example, a group may be optionally substituted with halo, —CN, —NO₂, or LsRs, wherein each Ls is independently selected from a bond, —O—, —C(=O)—, —C(=O)O—, —S—, —S(=O)—, —S(=O)₂—, —NH—, —NHC(=O)—, —C(=O)NH—, S(=O)₂NH—, —NHS(=O)₂, —OC(=O)NH—, —NHC(=O)O—, or —(C₁-C₆ alkyl); each Rs is selected from hydrogen, alkyl, fluoroalkyl, heteroalkyl, cycloalkyl, aryl, heteroaryl, or heterocycloalkyl. Protecting groups which can form a protected derivative of the above substituents are described in Greene and Wuts, supra. In one aspect, an optionally substituted group selected from halogen, CF₃, OH, CN, NO₂, SO₃H, SO₂NH₂, SO₂Me, NH₂, COOH, CONH₂, alkoxy, —N(CH₃)₂ and alkyl.

In certain embodiments, the compound having one or more stereocenters and each centre exists independently R or S type. Compounds mentioned herein include all diastereomers, enantiomers, epimers and their proper mixture. Stereoisomers can be obtained by, for example on a chiral HPLC column.

The methods described herein and include the use of formula acceptable N-oxides (if appropriate), crystalline forms (also known as polymorphs), or Formula (I) pharmaceutically acceptable salts of the compounds of Formula (I), and active metabolites of these compounds. In some cases, the compounds may exist as tautomers. All tautomers are included within the scope of the compounds mentioned herein. In a specific embodiment, the compound is in the form of a solvate, pharmaceutically acceptable solvents such as water, ethanol and the like. In other embodiments, the compound is a non-solvated form.

LIST OF ABBREVIATIONS

DMF=N, N-dimethylformamide
NMR=Nuclear Magnetic Resonance
LDA=Lithium diisopropylamide
THF=Tetrahydrofuran
PE=Petroleum ether
EA=Ethyl acetate
MS=Mass spectrometry
DCM=Dichloromethane
MeOH=Methanol
DMSO=Dimethyl sulfoxide
mCPBA=3-Chloroperbenzoic acid
HOBt=Hydroxybenzotriazole
HATU=O-(7-Azabenzotriazol-1-yl)-N,N,N',N'-tetramethyluronium hexafluorophosphate
DBU=1,8-Diazabicyclo[5.4.0]undec-7-ene
NADPH=Nicotinamide adenine dinucleotide phosphate
ACN=Acetonitrile The Pharmaceutically and Medically Specific Terminology The term "acceptable", as used herein, means that a component of the composition or the active ingredient has no excessively harmful effects on the health of general subject.

The term "HCV infection", as used herein, means that HCV viruses reach new organisms through blood or other transmissions, enter host-cells of organisms and initiate replication and proliferation.

The term "HCV inhibition", as used herein, means that compounds can show diminution of replication and reinfection of HCV viruses. Specifically, it means that copies of hereditary material RNA decrease in host-cells or blood.

The term "co-administration" or similar terms, as used herein, refers to administering several selected therapeutic agents for a patient in the same or different route of administration at the same time or different times.

The term "subject" or "patient" includes mammals and non-mammals. Examples of mammals include, but are not limited to, any member of mammalian: human, non-human primates such as chimpanzees and other apes and monkey species, farm animals such as cattle, horses, sheep, goats, pigs, livestock such as rabbits, dogs and cats, laboratory animals including rodents such as rats, mice and guinea pigs. Examples of non-mammals include, but are not limited to, birds, and fish. In one preferable embodiment, the mammal is a human.

As used herein, the term "treatment", "therapeutic process" or "therapy" includes reducing, reduction or improved disease or condition symptoms, preventing additional symptoms, improvement or prevention of symptoms of underlying metabolic causes, inhibiting the disease or condition such as preventing a disease or condition and alleviate the disease or condition, resulting in degenerative diseases or disorders, diseases or disorders caused by reducing illness, or termination of the symptoms of a disease or condition.

As used herein, a compound or its pharmaceutical composition, after administration, can make a disease, condition or symptom improvement, especially improve the severity, delay the onset and regress the disease, or reduce illness duration. Whether routine or temporary administration, continuous or intermittent administration, improvement may be attributed to the truth of administration.

Therapeutic Use and Administration Routes

The present invention also provides pharmaceutical compositions and treating methods, which comprise administering to the mammal an effective amount of a compound of Formula (I). The compounds in the present invention can be used for treating infection by HCV. Preferably the mammal is human being.

When used for treating the above diseases, the compounds of the present invention may be mixed with one or more pharmaceutically acceptable carriers or excipients, such as solvents and diluents. The compounds of the invention can be administered orally in the form of tablets, capsules, dispersible powders, granules, suspensions (e.g., containing about 0.05-5% suspending agent), syrups (e.g., containing about 10-50% sugar), elixirs (e.g., containing about 20-50% alcohol); or administered parenterally in the form of sterile injectable solutions or suspensions (e.g., containing 0.05-5% suspending agent in isotonic medium). For example, these pharmaceutics may contain about 25-90%, generally about 5-60% (by weight) active ingredients, which are mixed with the carriers.

The effective dose level of the active ingredient may vary with the specific compound employed, route of administration and the severity of the disease to be treated. However, when the daily dose of the compounds of this invention is administered in amounts from 0.5 to 500 mg/kg body weight, the effect is generally satisfying. Preferably, 2-4 divided dosages may be administered daily, and the dosage may be administered in slow-released forms. For most large mammals, daily total dosage is about 1-100 mg, preferably about 2-80 mg. Dosage forms suitable for oral administration include 0.5-500 mg active compound mixed with pharmaceutically acceptable solid or liquid carriers. The dosage scheme may be adjusted to provide the best therapeutic response. For example, according to the urgent need to suppress the disease condition, the dosage may be divided to several parts, or the dosage may be reduced proportionally.

The compounds of the present invention may be administered by any suitable means, for example, parenterally, such as by oral or intravenous, intramuscular, subcutaneous injection. Solid carrier includes: starch, lactose, dicalcium phosphate, microcrystalline cellulose, sucrose and kaolin. While liquid carrier includes: sterile water, polyethylene glycol, non-ionic surfactant and edible oil (such as corn oil, peanut oil and sesame oil), as long as they are suitable for the active ingredient and the specific administration route. Adjuvants, such as flavoring agent, pigment, preservative and antioxidant, such as vitamin E, vitamin C, BHT and BHA may be advantageously included in the preparation of pharmaceutically composition.

In view of ease to manufacture and administration, the preferred pharmaceutically composition is a solid composition, in particular, tablets or capsules filled with solid or liquid. Oral administration of compounds is preferred.

These active compounds may also be administered both parentally and intraperitoneally, and the solution or suspension of the active ingredients (as free base or pharmaceutically acceptable salt) can be manufactured in water mixed with surfactants (such as hydroxypropyl cellulose). Besides, the dispersion may be made in glycerin, liquid, polyethylene glycol and the mixture of polyethylene glycol in oil. Under the condition of regular storage and use, preservatives should be included in the preparations to inhibit the growth of microorganisms.

Dosage forms suitable for injection include: sterile water solution, dispersion and steriled powder (for instant preparation of steriled injectable solution or dispersion). Under all conditions, these dosage forms must be sterile and liquid, for the ejection from the syringes. The dosage forms must be stable under manufacturing and storage conditions, and must be spared the contamination of microorganisms (such as bacteria and fungi). The pharmaceutical carrier can be solvent or dispersing medium, including water, alcohol (such as glycerin, propylene glycol and liquid polyethylene glycol), the appropriate mixtures thereof and vegetable oils.

The present inventors have found that the macrocyclic compounds in the present invention can inhibit the HCV viruses efficiently. HCV viruses could be killed off standing out in an effective amount of these compounds. Thus the compounds in the present invention can be used for the manufacture of a medicament for treatment of infection by HCV, which can consist of a pharmaceutically acceptable carrier as it should be.

This specification (including any accompanying claims, abstract and drawings) described in the present invention, all features disclosed and/or disclosure of any such method or process steps can be any combination of all groups. Together, except where such features and/or steps are mutually exclusive combinations of at least some outside.

The present invention over the prior art, has the following advantages:

The present invention found a kind of compounds for preventing and treating HCV infection and unexpectedly, they can kill off HCV viruses efficiently. When the compound was incubated with the cells infected by HCV, it interfered with the replication of HCV, or at least some components of the virus. The present invention found the compounds with new molecular skeleton, which had high anti-HCV virus potency and excellent PK properties.

The invention is further illustrated by the following examples. These examples are only intended to illustrate the invention, but not to limit the scope of the invention.

Generally speaking, $^1$H NMR spectra were recorded on Bruker-400 magnetic resonance spectrometers. Chemical shifts are recorded in parts per million (ppm) relative to tetramethylsilane. Coupling constant is Hz. The abbreviations thereof are described as the following: s, singlet; d, doublet; t, triplet; q, quartet; qu, quint; m, multiplet; br, broad. Mass spectral data were obtained on Waters 2795 single quadrupole mass spectrometer, operating in electro-spray ionization (ESI) mode. Silica gel was used for column chromatography.

EXAMPLE 1

Compound IIa-1 tert-butyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$] hexacosa-6,8,10,12-tetraen-17-yl]carbamate

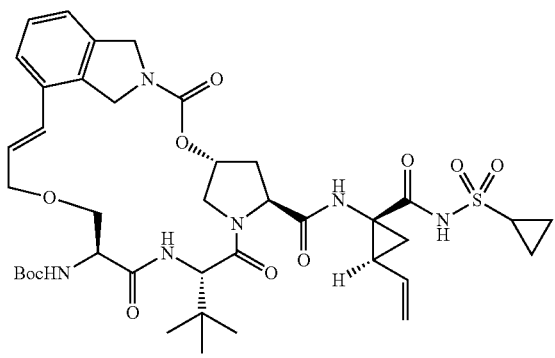 [SMILES: C=C[C@@H]1C[C@]1(NC(=O)[C@@H]1C[C@@H]2CN1C(=O)[C@H](C(C)(C)C)NC(=O)[C@@H](NC(=O)OC(C)(C)C)COC/C=C/c1cccc3c1CN(C3)C(=O)O2)C(=O)NS(=O)(=O)C1CC1]

Compound IIa-1 was prepared according to Schemes I, III and IV.

Intermediate A3: (2S,4R)-1-tert-butyl 2-methyl 4-(4-vinylisoindoline-2-carbonyloxy)pyrrolidine-1,2-dicarboxylate

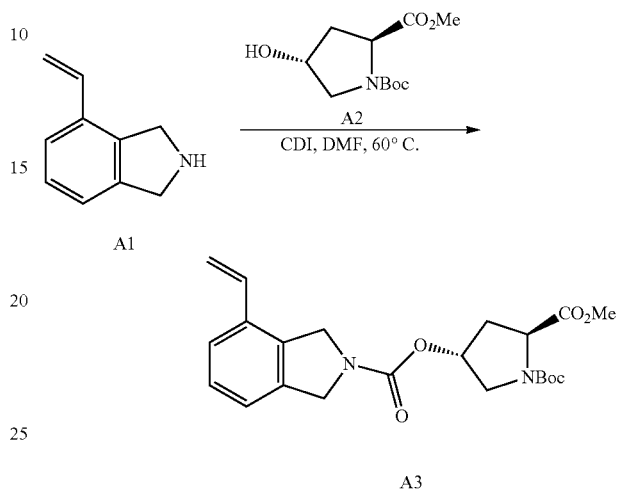

Following the procedure in Scheme I, alcohol A2 (2.21 g, 9.03 mmol) was dissolved in DMF (20 m L) and cooled to 0° C. Solid CDI (1.47 g, 9.03 mmol) was added in small portions while stirring. After stirring for a further 18 h at the room temperature, a solution of amine A1 (1.4 g, 9.03 mmol, J. Med. Chem. 2010, 53, 2443-2463) in DMF was added dropwise. The mixture was stirred for another 2 h at 60° C. and cooled to the room temperature. Ice water followed by 5% potassium hydrogen sulfate was added, and the mixture was extracted with EtOAc (3×). The combined organic layer was washed with water and brine, dried over Na$_2$SO$_4$, filtered, concentrated and purified by flash column chromatography to give the title compound A3 (2.3 g, 61%).

$^1$H NMR (400 MHz, CDC$_3$) δ 7.41-7.38 (m, 1H), 7.30-7.27 (m, 1H), 7.18-7.12 (m, 1H), 6.70 (dd, J=17.6, 10.8 Hz, 1H), 5.73 (dd, J=17.6, 4.0 Hz, 1H), 5.39 (d, J=10.8 Hz, 1H), 5.34 (brs, 1H), 4.79-4.67 (m, 4H), 4.52-4.37 (m, 1H), 3.78-3.76 (m, 5H), 2.54-2.43 (m, 1H), 2.28-2.20 (m, 1H), 1.47-1.44 (m, 9H).

Intermediate A5: (3R,5S)-1-((S)-2-(tert-butoxycarbonylamino)-3,3-dimethylbutanoyl)-5-(methoxycarbonyl)pyrrolidin-3-yl 4-vinylisoindoline-2-carboxylate

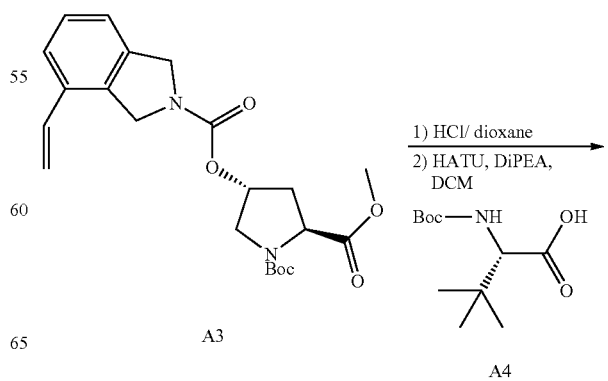

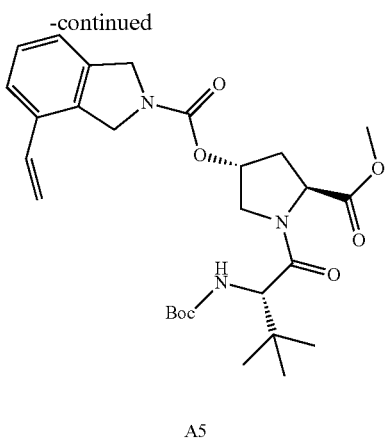

A5

Following the procedure in Scheme I, A3 (2.2 g, 5.28 mmol) was dissolved in 4N HCl/dioxane (30 mL) and stirred for 18 hours at the room temperature. After the reaction was completed, the mixture was concentrated to give crude deprotected compound (1.8 g, 100%), which was used directly in the next reaction without further purification.

N-BocLeu (2.4 g, 10.0 mmol), deprotected compound (3.5 g, 10.0 mmol), HATU (5.7 g, 14.9 mmol) and DiPEA (1.9 g, 14.9 mmol) were dissolved in DCM (40 mL). After stirring overnight at the room temperature, water was added and the mixture was extracted with DCM (3×). The combined organic layer was washed with water and brine, dried over Na$_2$SO$_4$, filtered, concentrated and purified by flash column chromatography to give the title compound A5 (2.9 g, 50%) as brown oil.

ESI-MS m/z 530.2 (M+H)$^+$.

Intermediate A6: (S)-3-(allyloxy)-2-(tert-butoxycarbonylamino)propanoic acid

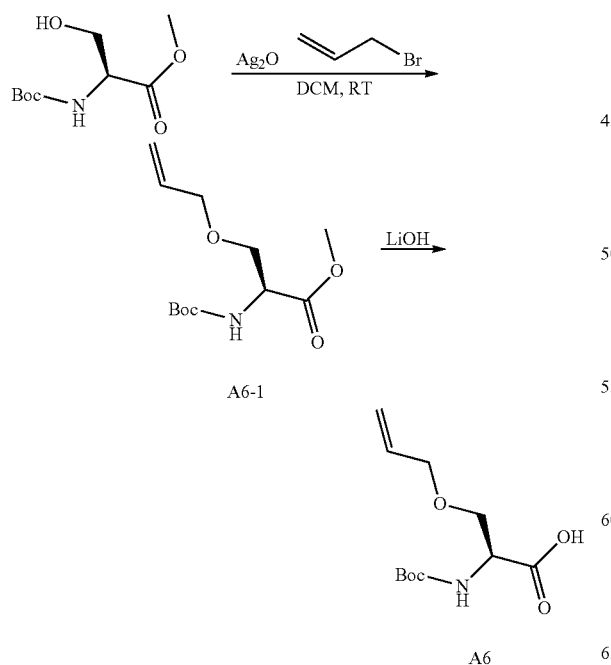

(S)-methyl 3-(allyloxy)-2-(tert-butoxycarbonylamino)propanoate (200 mg, 0.91 mmol) and 3-bromoprop-1-ene (552 mg, 4.56 mmol) were dissolved in DCM (10 mL). Then Ag$_2$O (654 mg, 2.74 mmol) was added at the room temperature. After stirring for 3 hours, the mixture was filtered, concentrated and purified by flash column chromatography to give the title compound A6-1 (149 mg, 63.1%) as light yellow oil.

$^1$H NMR (400 MHz, CDC$_3$) δ: 7.19 (d, J=8.0 Hz, 1H), 5.89-5.80 (m, 1H), 5.26 (dd, J=17.6, 1.6 Hz, 1H), 5.16 (d, J=11.6 Hz, 1H), 4.25 (dd, J=13.6, 5.6 Hz, 1H), 3.94 (d, J=6.8 Hz, 2H), 3.63 (s, 3H), 3.61-3.59 (m, 2H), 1.39 (s, 9H).

Intermediate A6-1 (120 mg, 0.46 mmol) was added in a solution of LiOH (53 mg, 1.28 mmol) in THF/H$_2$O (5 mL/2.5 mL). After stirring for 1 hour at the room temperature, the pH was adjusted to ~4 with 1.0 N HCl, aqueous layer was separated, and the mixture was extracted with ethyl acetate (EA) twice. The combined organic layer was washed with brine, dried over Na$_2$SO$_4$, filtered and concentrated to give the title compound A6 (110 mg, 97.3%) as light yellow oil, which was used directly in the next condensation reaction without further purification.

Intermediate A7: (3R,5S)-1-((S)-2-((S)-3-(allyloxy)-2-(tert-butoxycarbonylamino)propanamido)-3,3-dimethylbutanoyl)-5-(methoxycarbonyl)pyrrolidin-3-yl 4-vinylisoindoline-2-carboxylate

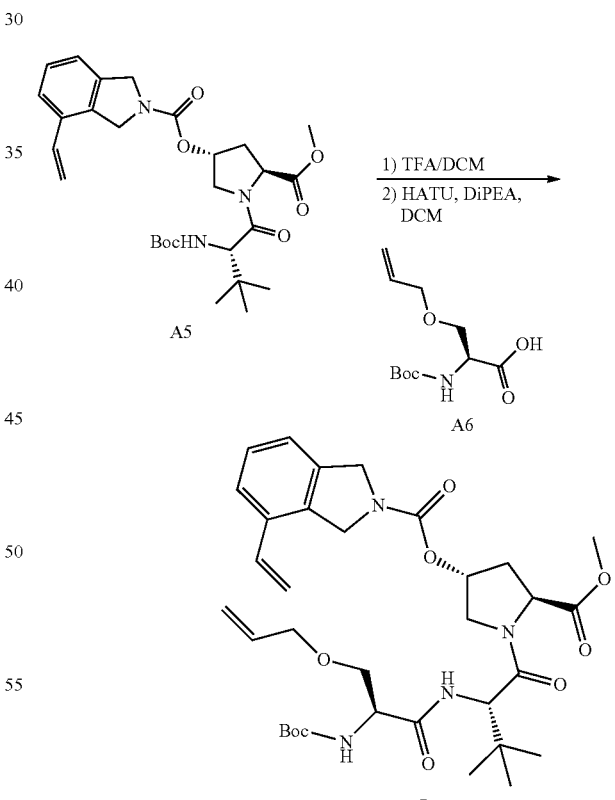

Following the procedure in Scheme I, A5 (2.9 g, 5.5 mmol) was dissolved in dichloromethane (DCM) (50 mL) and TFA (10 mL, 20%) was added dropwise. Then the mixture was stirred for 3 hours at the room temperature and concentrated. Water and DCM was added and the pH was adjusted to ~12 with 2N NaOH. The mixture was extracted with three times.

The combined organic layer was washed with brine, dried over $Na_2SO_4$, filtered and concentrated to give the crude Boc-removed product (2.0 g, 85.1%), which was used directly in the next reaction without further purification.

Amino acid A6 (1.1 g, 4.7 mmol), the crude Boc-removed product (2.0 g, 4.7 mmol), HATU (2.3 g, 6.1 mmol) and DiPEA (0.9 g, 7.0 mmol) were dissolved in DCM (30 mL). After stirring overnight at the room temperature, water was added and the mixture was extracted three times. The combined organic layer was washed with water and brine, dried over $Na_2SO_4$, filtered, concentrated and purified by flash column chromatography to give the title compound A7 (1.25 g, 40.3%) as light yellow oil.

$^1$H NMR (400 MHz, $CDC_3$) δ 7.41-7.38 (m, 1H), 7.24-7.14 (m, 2H), 6.71-6.62 (m, 0.5H), 5.91-5.81 (m, 1H), 5.72-5.65 (m, 0.5H), 5.42-5.36 (m, 2H), 5.30-5.15 (m, 3H), 4.86-4.61 (m, 5H), 4.55-4.51 (m, 1H), 4.22-4.13 (m, 2H), 4.00-3.88 (m, 4H), 3.45-3.38 (m, 1H), 2.54-2.48 (m, 1H), 2.27-2.20 (m, 1H), 1.47-1.43 (m, 9H), 1.00 (s, 9H).

Intermediate A8: tert-butyl N-[(1R,12E,17S,20S, 23S)-20-tert-butyl-23-methoxycarbonyl-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

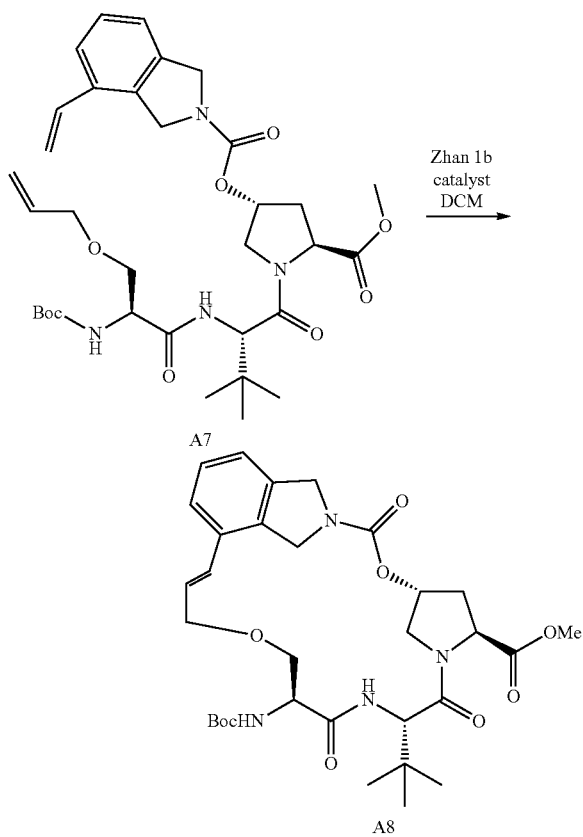

A7

Following the procedure in Scheme I, A7 (31 mg, 0.047 mmol) was dissolved in DCM (20 mL) and Zhan catalyst (3.5 mg, 0.005 mmol) was added. Then the mixture was stirred overnight at r.t. 0.1 mL DMSO was added into the mixture. Then the mixture was concentrated and purified by flash column chromatography to give the title compound A8 (10 mg, 34.4%).

$^1$H NMR (400 MHz, $CDC_3$) δ 7.31-7.25 (m, 2H), 7.20-7.15 (m, 1H), 6.83 (d, J=16.0 Hz, 1H), 6.08 (d, J=16.0 Hz, 1H), 5.58 (d, J=7.6 Hz, 1H), 5.29 (brs, 1H), 4.90-4.65 (m, 5H), 4.48-4.32 (m, 4H), 4.17-4.09 (m, 2H), 3.80-3.76 (m, 4H), 3.43-3.38 (m, 1H), 2.78-2.72 (m, 1H), 2.20-2.14 (m, 1H), 1.49 (s, 9H), 1.10 (s, 9H).

Intermediate A9: tert-butyl N-[(1R,12E,17S,20S, 23S)-20-tert-butyl-23-hydroxycarbonyl-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

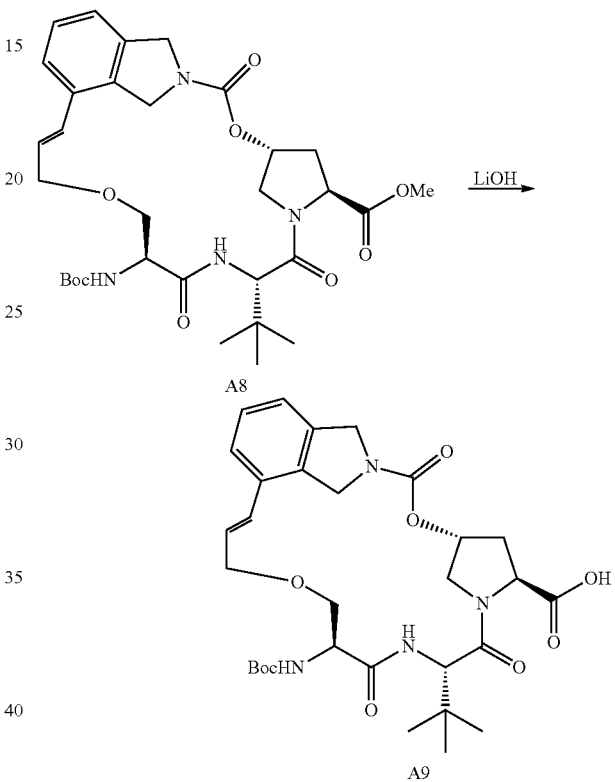

Intermediate A8 (66 mg, 0.11 mmol) was added in a solution of LiOH (53 mg, 1.28 mmol) in THF/$H_2O$ (5 mL/2.5 mL). After stirring for 1 hour at the room temperature, the pH was adjusted to ~4 with 1N HCl, aqueous layer was separated, and the mixture was extracted with EA twice. The combined organic layer was washed with brine, dried over $Na_2SO_4$, filtered and concentrated to give the title compound A9 (56 mg, 86.8%) as light yellow oil, which was used directly in the next reaction without further purification.

Intermediate C2: (E)-ethyl 2-(benzylideneamino)acetate

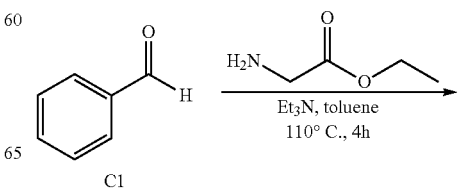

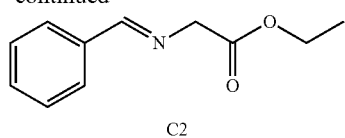

C2

Following the procedure in Scheme III, ethyl glycine (65.0 g, 0.64 mol) and Et₃N (100 mL, 0.71 mol) were dissolved in toluene (500 mL). To the mixture was added benzaldehyde (50.0 g, 0.47 mol). After refluxed for 4 hours, the mixture was concentrated. Then 200 mL EA was added and extracted three times. The combined organic layer was washed with water and brine, dried over Na₂SO₄, filtered and concentrated to give brown oil C2 (80.0 g, 88.9%), which was used directly in the next reaction without further purification.

Intermediate C3: (E)-ethyl 1-(benzylideneamino)-2-vinylcyclopropanecarboxylate

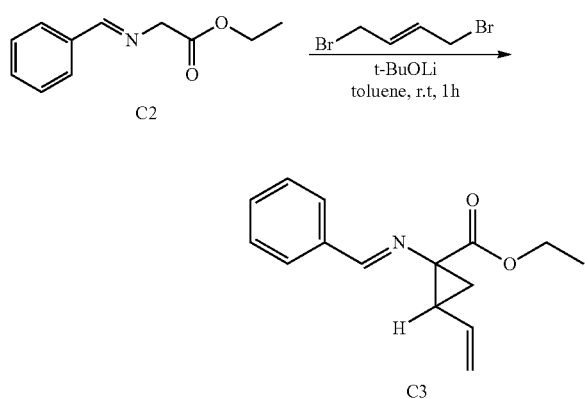

Following the procedure in Scheme III, C2 (40.0 g, 0.20 mol) and (E)-1,4-dibromobut-2-ene (44.0 g, 0.20 mol) were dissolved in toluene (100 mL) under N₂ atmosphere. A solution of ᵗBuOK (32.0 g, 0.40 mol) in toluene (100 mL) was added dropwise while stirring. After stirring for another 1 h, water and EA (20 mL×3) were added, and the mixture was extracted three times. The combined organic layer was washed with water and brine, dried over Na₂SO₄, filtered and concentrated to give intermediate C3, which was used directly in the next reaction without further purification.

Intermediate C4: ethyl 1-(tert-butoxycarbonylamino)-2-vinylcyclopropanecarboxylate

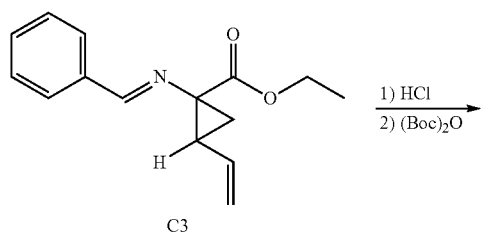

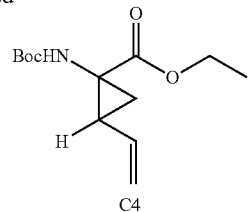

C4

Following the procedure in Scheme III, the above intermediate C3 was dissolved in EA (50 mL) and, while stirring, 1N HCl (200 mL) was added dropwise. Then the mixture was stirred for 2 hours and allowed to stand and separate into layers. The organic layer was extracted with water twice. The combined water layer was washed with EA and the pH was adjusted to ~12 with 2N NaOH. Then the mixture was extracted with MTBE twice, washed with brine, dried over Na₂SO₄, filtered and concentrated to afford crude amine intermediate. Such crude intermediate was redissolved in MTBE. (Boc)₂O (68.0 g, 0.30 mol) and (50 mL, 0.30 mol) were added. After stirring for 2 h at r.t., water and EA (20 mL×3) were added, and the mixture was extracted three times. The combined organic layer was washed with 1N HCl and brine, dried over Na₂SO₄, filtered, concentrated and purified by flash column chromatography to give the title compound C4 (26.0 g, 49.1%) as light yellow oil.

¹H NMR (400 MHz, DMSO-d6) δ 5.80-5.51 (m, 1H), 5.30-5.09 (m, 2H), 4.19-4.13 (m, 2H), 2.16 (q, J=10.8 Hz, 1H), 1.80-1.75 (m, 1H), 1.50-1.45 (m, 1H), 1.44 (s, 9H), 1.27 (t, J=6.8 Hz, 3H).

Intermediate C5: (1R,2S)-ethyl 1-(tert-butoxycarbonylamino)-2-vinylcyclopropanecarboxylate

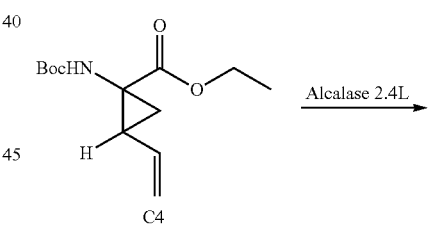

Following the procedure in Scheme III, Alcalase 2.4 L (100 mL) was dissolved in buffer (500 ml) at 40° C. and the pH was adjusted to ~8 with 50% NaOH. A solution of C4 (26.0 g, 0.11 mol) in DMSO (100 mL) was added into the mixture dropwise. After stirring for further 72 h, the pH was adjusted to ~8.5. Then the mixture was extracted with water and EA twice. The combined organic layer was washed with 1N HCl and brine, dried over Na₂SO₄, filtered, concentrated and purified by flash column chromatography to give the title compound C5 (13.0 g, 49.1%, 100% ee) as light yellow oil.

Intermediate C6: tert-butyl (1R,2S)-1-(cyclopropylsulfonylcarbamoyl)-2-vinylcyclopropylcarbamate

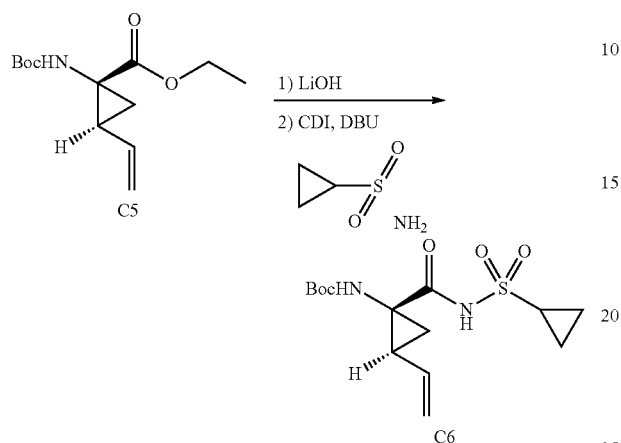

Following the procedure in Scheme III, Intermediate C5 (6.0 g, 23.5 mmol) was added in a solution of LiOH (3.0 g, 73.5 mmol) in THF/MeOH/H₂O (20 mL/20 mL/10 mL). After 1 h at r.t., the pH was adjusted to ~4 with 1N HCl, aqueous layer was separated, EA was added, and the mixture was extracted with EA twice. The combined organic layer was washed with brine, dried over Na₂SO₄, filtered and concentrated to give the yellow oil, which was used directly in the next reaction without further purification.

Then the intermediate (5.6 g, 24.2 mmol) and CDI (5.2 g, 31.5 mmol) were dissolved in THF (20 mL). After refluxed for 1 h, the mixture was cooled to r.t. and then a solution of cyclopropanesulfonamide (3.8 g, 31.5 mmol) in DCM (30 mL) was added followed by adding DBU (5.2 mg, 34.0 mmol). The mixture was stirred overnight at the room temperature, concentrated and extracted with EA twice. The combined organic layer was washed with brine, dried over Na₂SO₄, filtered, concentrated and purified by flash column chromatography to give the title compound C6 (2.8 g, 36.4%) as white solid.

$^1$H NMR (400 MHz, CDC₃) δ 9.52 (s, 1H), 5.66-5.57 (m, 1H), 5.32 (d, J=13.2 Hz, 1H), 5.17 (dd, J=10.4, 0.8 Hz, 1H), 2.94-2.87 (m, 1H), 2.17 (q, J=8.4 Hz, 1H), 1.92-1.89 (m, 1H), 1.48 (s, 9H), 1.45-1.39 (m, 1H), 1.32-1.25 (m, 2H), 1.13-1.00 (m, 2H).

Intermediate C7: (1R,2S)-1-amino-N-(cyclopropylsulfonyl)-2-vinylcyclopropanecarboxamide

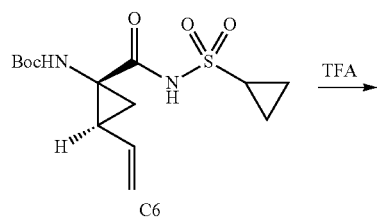

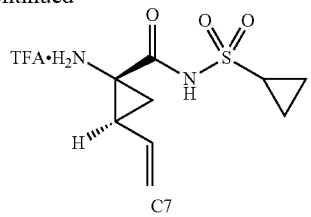

Following the procedure in Scheme III, C6 (1.0 g, 3.0 mmol) was dissolved in DCM (10 mL), and TFA (2 mL, 20%) was added dropwise. Then the mixture was stirred for 2 h and concentrated to give the title product C7 (1.2 g, 100%) as brown oil, which was used directly in the next reaction without further purification.

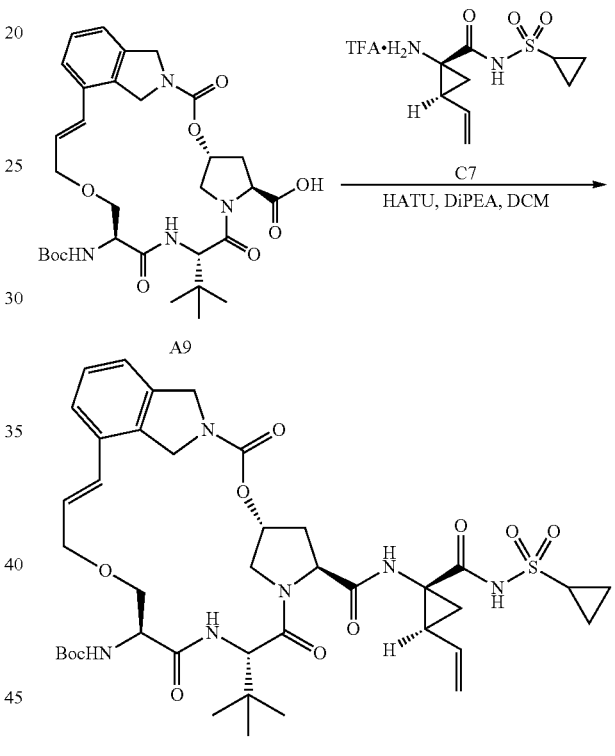

Following the procedure in Scheme IV, left acid fragment A9 (56 mg, 0.10 mmol), the amine fragment C7 (24 mg, 0.10 mmol), HATU (58 mg, 0.15 mmol) and DiPEA (27 mg, 0.20 mmol) were dissolved and mixed in DCM (10 mL). After stirring overnight at the room temperature, water and DCM was added and the mixture was extracted with DCM three times. The combined organic layer was washed with water and brine, dried over Na₂SO₄, filtered, concentrated and purified by flash column chromatography to give the title compound IIa-1 (17 mg, 22.7%) as white powder.

$^1$H NMR (400 MHz, CDC₃) δ 9.91 (brs, 1H), 7.42-7.38 (m, 1H), 7.19-7.07 (m, 2H), 6.75 (d, J=20.8 Hz, 1H), 6.02 (d, J=20.8 Hz, 1H), 5.61-5.55 (m, 2H), 5.23-5.05 (m, 3H), 4.80-4.64 (m, 4H), 4.39-4.26 (m, 5H), 4.10-3.95 (m, 2H), 3.66-3.64 (m, 4H), 3.40-3.32 (m, 1H), 2.82-2.72 (m, 1H), 2.50-2.40 (m, 1H), 2.35-2.20 (m, 1H), 2.00-1.80 (m, 4H), 1.40 (s, 9H), 1.35-1.30 (m, 2H), 1.26-1.15 (m, 2H), 0.98 (s, 9H); ESI-MS m/z 849.00 (Manna)⁺.

EXAMPLE 2

Compound IIa-2

(1R,12E,17S,20S,23S)-17-amino-20-tert-butyl-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide

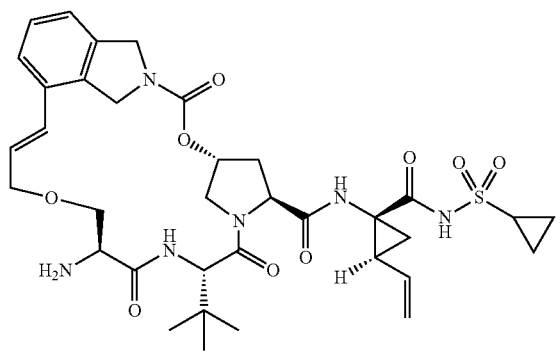 [SMILES: C=C[C@@H]1C[C@]1(NC(=O)[C@@H]1C[C@@H]2CN1C(=O)[C@H](C(C)(C)C)NC(=O)[C@@H](N)COC/C=C/c1cccc3c1CN(C3)C(=O)O2)C(=O)NS(=O)(=O)C1CC1]

IIa-1 (10 mg, 0.012 mmol) was dissolved in DCM (5 mL), and TFA (1 mL, 20%) was added dropwise. Then the mixture was stirred for 2 hours at the room temperature. After the reaction was completed, the mixture was concentrated. Water and DCM was added to the residue and the pH was adjusted to ~12 with 2N NaOH. Then the mixture was extracted with DCM (3×), washed with brine, dried over Na$_2$SO$_4$, filtered, concentrated and purified by flash column chromatography to give the title compound IIa-2 (2.3 mg, 26.1%) as white powder.

ESI-MS m/z 727.00 (M+H)$^+$.

EXAMPLE 3

Compound IIa-3 tert-butyl N-[(1R,12E,17R,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

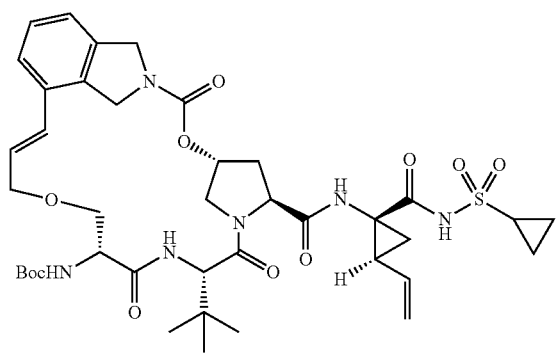 [SMILES: C=C[C@@H]1C[C@]1(NC(=O)[C@@H]1C[C@@H]2CN1C(=O)[C@H](C(C)(C)C)NC(=O)[C@H](NC(=O)OC(C)(C)C)COC/C=C/c1cccc3c1CN(C3)C(=O)O2)C(=O)NS(=O)(=O)C1CC1]

Compound IIa-3 was prepared in accordance with the procedures as described in Example 1 by using N-Boc-D-Serine methyl ester as the starting material.

$^1$H NMR (400 MHz, CDC$_3$) δ 9.97 (brs, 1H), 7.28-7.08 (m, 3H), 6.55 (d, J=17.6 Hz, 1H), 5.90-5.65 (m, 3H), 5.52 (s, 1H), 5.28-5.14 (m, 2H), 4.82-4.60 (m, 6H), 4.47-4.26 (m, 6H), 3.94-3.79 (m, 2H), 3.42-3.32 (m, 1H), 2.92-2.82 (m, 1H), 2.50-2.36 (m, 2H), 2.11-1.96 (m, 3H), 1.52 (s, 9H), 1.35-1.30 (m, 3H), 1.06 (s, 9H), 1.06-1.02 (m, 2H); ESI-MS m/z 849.00 (M+Na)$^+$.

EXAMPLE 4

Compound IIa-4

(1R,12E,17R,20S,23S)-17-amino-20-tert-butyl-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide

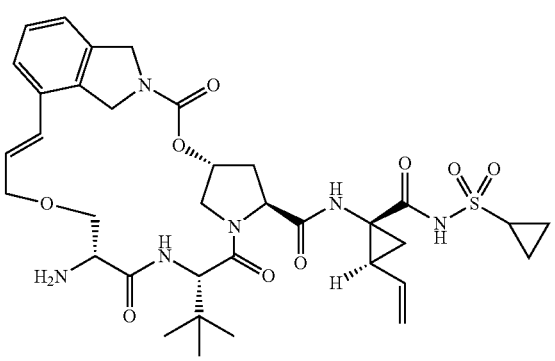 [SMILES: C=C[C@@H]1C[C@]1(NC(=O)[C@@H]1C[C@@H]2CN1C(=O)[C@H](C(C)(C)C)NC(=O)[C@H](N)COC/C=C/c1cccc3c1CN(C3)C(=O)O2)C(=O)NS(=O)(=O)C1CC1]

In accordance with the procedures as described in Example 2, IIa-3 removes the Boc group and then was purified to give Compound IIa-4.

ESI-MS m/z 727.00 (M+H)$^+$.

EXAMPLE 5

Compound IIa-5

(1R,12E,17S,20S,23S)-20-tert-butyl-23-N-[(1R,2S)-1-[(cyclopropanesulfonyl)carbamoyl]-2-ethenylcyclopropyl]-3,18,21-trioxo-17-C-pyrazine-2-2,15-dioxa-4,19,22-triazatetracyclo[20.2.1.1$^{4,7}$.0$^{6,11}$]hexacosa-6,8,10,12-tetraene-17,23-diamido

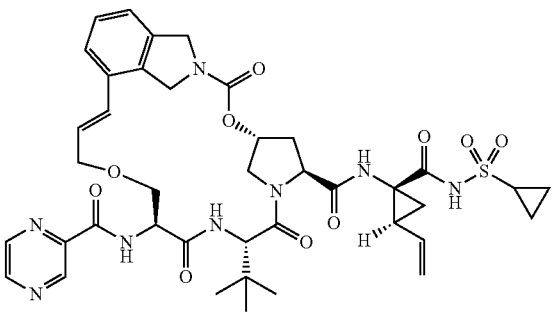 [SMILES: C=C[C@@H]1C[C@]1(NC(=O)[C@@H]1C[C@@H]2CN1C(=O)[C@H](C(C)(C)C)NC(=O)[C@@H](NC(=O)c1cnccn1)COC/C=C/c1cccc3c1CN(C3)C(=O)O2)C(=O)NS(=O)(=O)C1CC1]

Compound IIa-2 was coupled with pyrazine-2-carboxylic acid, and then purified to give Compound IIa-5.

$^1$H NMR (400 MHz, CDC$_3$) δ 9.46 (s, 1H), 8.80 (d, J=2.8 Hz, 1H), 8.72 (d, J=8.0 Hz 1H), 8.56 (s, 1H), 7.75 (d, J=8.0 Hz 1H), 7.59 (brs, 1H), 7.26-7.23 (m, 2H), 7.19 (d, J=6.8 Hz, 1H), 6.75 (d, J=17.2 Hz, 1H), 6.05-6.00 (m, 1H), 5.78-5.69 (m, 1H), 5.38 (s, 1H), 5.28-5.14 (m, 2H), 5.05-5.01 (m, 1H), 4.91-4.87 (m, 1H), 4.80-4.76 (m, 3H), 4.59-4.51 (m, 2H), 4.36-4.33 (m, 2H), 4.19-4.07 (m, 2H), 3.85-3.81 (m, 1H), 3.68-3.65 (m, 1H), 2.90-2.86 (m, 1H), 2.65-2.60 (m, 1H), 2.40-2.33 (m, 1H), 2.19-2.00 (m, 1H), 1.96-1.92 (m, 1H), 1.47-1.41 (m, 1H), 1.10-1.02 (m, 11H); ESI-MS m/z 855.00 (M+Na)$^+$.

EXAMPLE 6

Compound IIa-6

(1R,12E,17R,20S,23S)-20-tert-butyl-23-N-[(1R,2S)-1-[(cyclopropanesulfonyl)carbamoyl]-2-ethenylcyclopropyl]-3,18,21-trioxo-17-C-pyrazine-2-2,15-dioxa-4,19,22-triazatetracyclo[20.2.1.1$^{4,7}$.0$^{6,11}$]hexacosa-6,8,10,12-tetraene-17,23-diamido

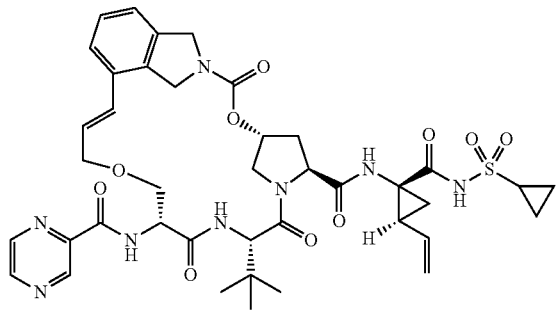 [SMILES: C=C[C@@H]1C[C@]1(NC(=O)[C@@H]1C[C@@H]2CN1C(=O)[C@H](C(C)(C)C)NC(=O)[C@H](NC(=O)c1cnccn1)COC/C=C/c1cccc3c1CN(C3)C(=O)O2)C(=O)NS(=O)(=O)C1CC1]

Compound IIa-4 was coupled with pyrazine-2-carboxylic acid, and then purified to give Compound IIa-6.

$^1$H NMR (400 MHz, CDC$_3$) δ 10.0 (s, 1H), 9.43 (s, 1H), 8.78 (s, 1H), 8.73 (d, J=7.8 Hz, 1H), 8.55 (s, 1H), 7.63 (d, J=7.8 Hz, 1H), 7.45 (s, 1H), 7.26-7.16 (m, 2H), 6.75 (d, J=16.0 Hz, 1H), 6.06-6.01 (m, 1H), 5.78-5.72 (m, 1H), 5.35 (s, 1H), 5.28-5.15 (m, 2H), 4.92-4.74 (m, 6H), 4.51-4.13 (m, 7H), 3.85-3.77 (m, 2H), 3.68-3.62 (m, 2H), 2.90-2.86 (m, 1H), 2.65-2.58 (m, 1H), 2.38-2.33 (m, 1H), 2.18-1.94 (m, 4H), 1.47-1.41 (m, 2H), 1.02 (s, 9H); ESI-MS m/z 855.00 (M+Na)$^+$.

EXAMPLE 7

Compound IIa-7

(1R,12E,17S,20S,23S)-20-tert-butyl-N-[(1R,2S)-1-[(cyclopropanesulfonyl)carbamoyl]-2-ethenylcyclopropyl]-17-acetamido-3,18,21-trioxo-2,15-dioxa-4,19,22-triazatetracyclo[20.2.1.1$^{4,7}$.0$^{6,11}$]hexacosa-6,8,10,12-tetraene-23-carboxamide

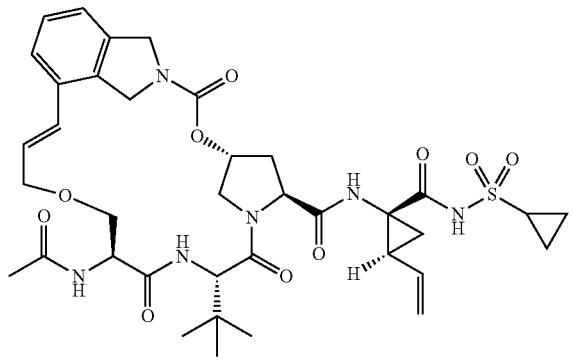 [SMILES: C=C[C@@H]1C[C@]1(NC(=O)[C@@H]1C[C@@H]2CN1C(=O)[C@H](C(C)(C)C)NC(=O)[C@@H](NC(C)=O)COC/C=C/c1cccc3c1CN(C3)C(=O)O2)C(=O)NS(=O)(=O)C1CC1]

In accordance with the procedures as described in Example 5, Compound IIa-2 was coupled with acetyl chloride, and then purified to give Compound IIa-7.

$^1$H NMR (400 MHz, CDC$_3$) δ 10.0 (brs, 1H), 7.75-7.70 (m, 2H), 7.24-7.22 (m, 2H), 7.16 (d, J=6.8 Hz, 1H), 6.69 (s, 1H), 6.75 (d, J=16.8 Hz, 1H), 5.98 (d, J=16.4 Hz, 1H), 5.68-5.60 (m, 1H), 5.34 (s, 1H), 5.30-5.11 (m, 2H), 4.86-4.74 (m, 5H), 4.55-4.49 (m, 2H), 4.32-4.25 (m, 2H), 3.82-3.80 (m, 1H), 3.46-3.40 (m, 1H), 2.85-2.82 (m, 1H), 2.59-2.50 (m, 1H), 2.35-2.31 (m, 1H), 2.17 (s, 3H), 1.91-1.80 (m, 2H), 1.40-1.33 (m, 4H), 1.05 (s, 9H); ESI-MS m/z 791.00 (M+Na)$^+$.

EXAMPLE 8

Compound IIa-8

(1R,12E,17S,20S,23S)-20-tert-butyl-N-[(1R,2S)-1-[(cyclopropanesulfonyl)carbamoyl]-2-ethenylcyclopropyl]-17-methanesulfonamido-3,18,21-trioxo-2,15-dioxa-4,19,22-triazatetracyclo[20.2.1.1$^{4,7}$.0$^{6,11}$]hexacosa-6,8,10,12-tetraene-23-carboxamide

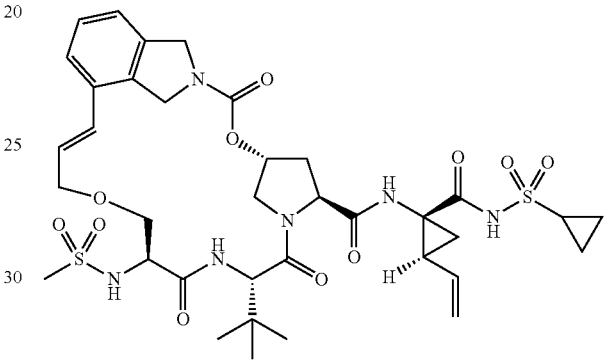

In accordance with the procedures as described in Example 5, Compound IIa-2 was coupled with methanesulfonyl chloride, and then purified to give Compound IIa-8.

$^1$H NMR (400 MHz, CDC$_3$) δ 10.0 (brs, 1H), 7.45 (d, J=7.6 Hz, 1H), 7.34 (s, 1H), 7.24-7.20 (m, 2H), 7.15 (d, J=6.8 Hz, 1H), 6.59 (d, J=16.4 Hz, 1H), 5.91 (d, J=16.4 Hz, 1H), 5.78-5.60 (m, 1H), 5.52 (d, J=8.8 Hz, 1H), 5.35 (s, 1H), 5.23-5.12 (m, 2H), 4.77-4.73 (m, 4H), 4.52 (d, J=8.0 Hz, 1H), 4.40-4.19 (m, 5H), 4.11-4.03 (m, 2H), 3.81-3.77 (m, 1H), 3.54-3.40 (m, 1H), 2.89-2.82 (m, 1H), 2.59-2.53 (m, 1H), 2.35-2.28 (m, 1H), 2.17 (s, 3H), 2.08-2.00 (m, 1H), 1.96-1.90 (m, 1H), 1.40-1.33 (m, 1H), 1.07 (s, 9H), 1.07-1.02 (m, 3H); ESI-MS m/z 827.00 (M+Na)$^+$.

EXAMPLE 9

Compound IIa-9 ethyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

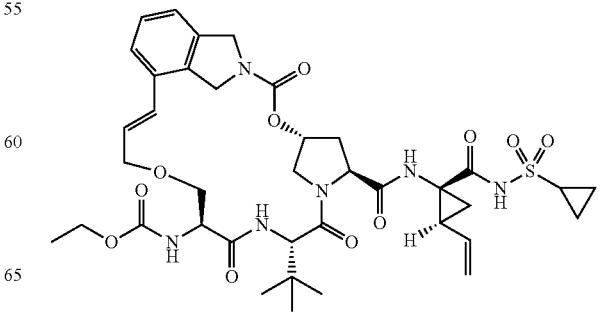

In accordance with the procedures as described in Example 5, Compound IIa-2 was coupled with cathyl chloride, and then purified to give Compound IIa-9.

$^1$H NMR (400 MHz, CDC$_3$) δ 9.94 (brs, 1H), 7.43-7.26 (m, 3H), 7.16 (s, 1H), 6.70 (d, J=15.2 Hz, 1H), 5.98 (d, J=16.4 Hz, 1H), 5.70-5.60 (m, 2H), 5.34 (s, 1H), 5.23-5.14 (m, 2H), 4.83-4.72 (m, 4H), 4.52-3.98 (m, 9H), 3.81-3.79 (m, 1H), 3.54-3.47 (m, 1H), 2.89-2.82 (m, 1H), 2.57-2.53 (m, 1H), 2.38-2.28 (m, 1H), 2.22-2.15 (m, 1H), 2.08-1.91 (m, 3H), 1.42-1.33 (m, 2H), 1.27-1.25 (m, 3H), 1.05 (s, 9H); ESI-MS m/z 821.00 (M+Na)$^+$.

EXAMPLE 10

Compound IIa-10 benzyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

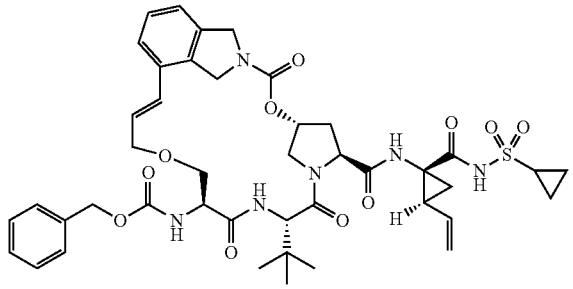 [SMILES: C=C[C@@H]1C[C@]1(NC(=O)[C@@H]1C[C@@H]2CN1C(=O)[C@H](C(C)(C)C)NC(=O)[C@@H](NC(=O)OCc1ccccc1)COC/C=C/c1cccc3c1CN(C3)C(=O)O2)C(=O)NS(=O)(=O)C1CC1]

In accordance with the procedures as described in Example 5, Compound IIa-2 was coupled with Benzyl chloroformate, and then purified to give Compound IIa-10.

$^1$H NMR (400 MHz, CDC$_3$) δ 7.51 (s, 1H), 7.48-7.26 (m, 7H), 7.15 (s, 1H), 6.70 (d, J=17.2 Hz, 1H), 5.98 (d, J=16.0 Hz, 1H), 5.85-5.60 (m, 2H), 5.40-5.09 (m, 5H), 4.85-4.73 (m, 4H), 4.48-4.40 (m, 3H), 4.28-4.20 (m, 2H), 4.09-3.97 (m, 2H), 3.81-3.76 (m, 1H), 3.54-3.47 (m, 1H), 2.88-2.82 (m, 1H), 2.58-2.53 (m, 1H), 2.34-2.26 (m, 1H), 2.06-1.91 (m, 2H), 1.39-1.33 (m, 2H), 1.31-1.25 (m, 2H), 0.99 (s, 9H); ESI-MS m/z 882.65 (M+Na)$^+$.

EXAMPLE 11

Compound IIa-11 cyclopentyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

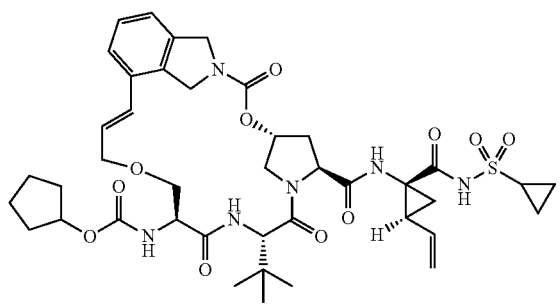 [SMILES: C=C[C@@H]1C[C@]1(NC(=O)[C@@H]1C[C@@H]2CN1C(=O)[C@H](C(C)(C)C)NC(=O)[C@@H](NC(=O)OC1CCCC1)COC/C=C/c1cccc3c1CN(C3)C(=O)O2)C(=O)NS(=O)(=O)C1CC1]

In accordance with the procedures as described in Example 5, Compound IIa-2 was coupled with cyclopentyl chloroformate, and then purified to give Compound IIa-11.

$^1$H NMR (400 MHz, CDC$_3$) δ 7.50 (s, 2H), 7.30-7.26 (m, 2H), 7.16 (s, 1H), 6.70 (d, J=16.8 Hz, 1H), 5.98 (d, J=16.8 Hz, 1H), 5.80-5.67 (m, 2H), 5.33-5.12 (m, 4H), 4.83-4.72 (m, 4H), 4.52-4.40 (m, 3H), 4.31-4.25 (m, 2H), 4.09-3.99 (m, 2H), 3.81-3.77 (m, 1H), 3.54-3.48 (m, 1H), 2.89-2.82 (m, 1H), 2.57-2.53 (m, 1H), 2.36-2.26 (m, 1H), 2.08-1.80 (m, 6H), 1.59-1.50 (m, 4H), 1.39-1.33 (m, 2H), 1.10-1.05 (m, 2H), 1.05 (s, 9H); ESI-MS m/z 861.00 (M+Na)$^+$.

EXAMPLE 12 Compound IIa-12

(1R,12E,17S,20S,23S)-20-tert-butyl-17-[(tert-butylcarbamoyl)amino]-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide

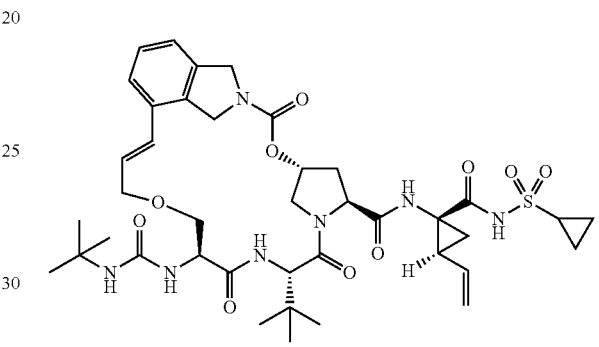

In accordance with the procedures as described in Example 5, Compound IIa-2 was coupled with tert-butylisocyanate, and then purified to give Compound IIa-11.

$^1$H NMR (400 MHz, CDC$_3$) δ 8.39 (brs, 1H), 8.02 (d, J=8.0 Hz, 1H), 7.22 (d, J=7.2 Hz, 1H), 7.13-7.11 (m, 2H), 7.19-7.07 (m, 2H), 6.52 (d, J=15.6 Hz, 1H), 5.88 (d, J=16.0 Hz, 1H), 5.61-5.55 (m, 2H), 5.37 (s, 1H), 5.25-5.12 (m, 2H), 4.85-4.20 (m, 10H), 3.91-3.83 (m, 3H), 3.40-3.38 (m, 1H), 2.89-2.72 (m, 1H), 2.59-2.50 (m, 1H), 2.34-2.20 (m, 1H), 2.10-2.04 (m, 2H), 1.88-1.80 (m, 2H), 1.33 (s, 9H), 1.06 (s, 9H); ESI-MS m/z 848.00 (M+Na)$^+$.

EXAMPLE 13

Compound IIa-13 tert-butyl N-[(1R,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate

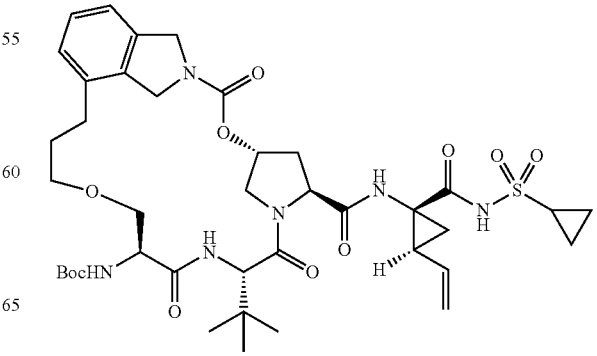

Intermediate A8 in Example 1 was hydrogenated and hydrolyzed, coupled with right fragment C7, and then purified to give Compound IIa-13.

Step 1: Preparation of the intermediate A9-1

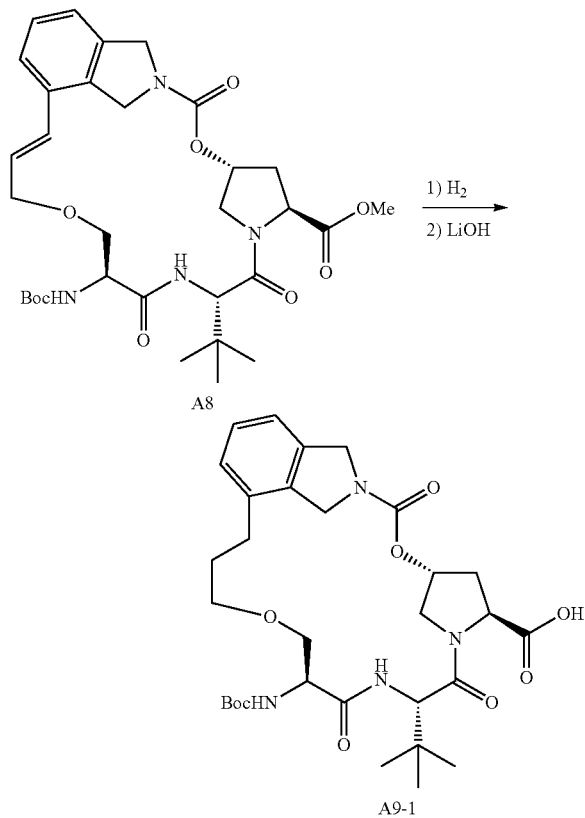

10% Pd/C (30 mg, 20%) was added into a solution of A8 (75 mg, 0.12 mmol) in EA (10 mL). The mixture was stirred overnight under $H_2$ at the normal pressure, filtered and concentrated to the crude product (57 mg, 76.0%) as light yellow oil, which was used directly in the next reaction without further purification.

The hydrogenated product (57 mg, 0.09 mmol) was added into a solution of LiOH (12 mg, 0.27 mmol) in THF/$H_2O$ (5 mL/2.5 mL). After stirring for 1 h at r.t., the pH was adjusted to ~4 with 1N HCl and the mixture was extracted with EA (2×). The combined organic layer was washed with brine, dried over $Na_2SO_4$, filtered and concentrated to give the light yellow oil A9-1 (52 mg, 93.4%), which was used directly in the next reaction without further purification.

Step 2: Preparation of Compound IIa-13

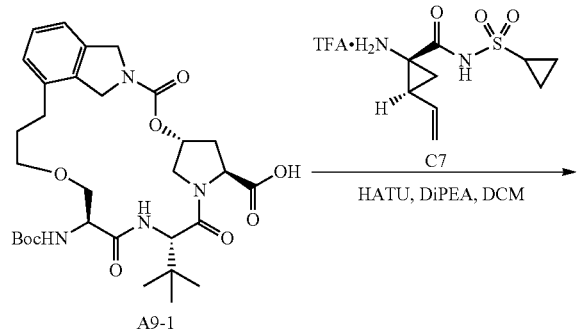

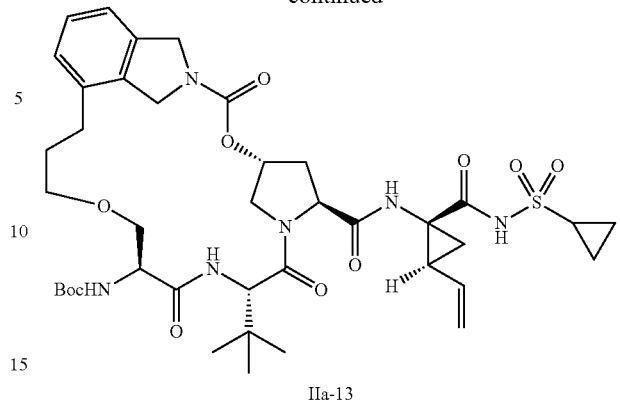

Following the procedure in Scheme IV, left acid fragment A9-1 (52 mg, 0.08 mmol), the crude amine C7 (29 mg, 0.08 mmol), HATU (50 mg, 0.12 mmol) and DiPEA (20 mg, 0.16 mmol) were dissolved in DCM (10 mL). After stirring overnight at the room temperature, water and DCM were added, and the mixture was extracted with DCM three times. The combined organic layer was washed with water and brine, dried over $Na_2SO_4$, filtered, concentrated and purified by flash column chromatography to give the title compound IIa-13 (16 mg, 22.9%) as white powder.

$^1$H NMR (400 MHz, CDC$_3$) δ 10.05 (brs, 1H), 7.58 (s, 1H), 7.20 (d, J=7.6 Hz, 1H), 7.10-7.05 (m, 2H), 5.80-5.72 (m, 1H), 5.45-5.38 (m, 2H), 5.27-5.13 (m, 2H), 4.79-4.65 (m, 4H), 4.53-4.29 (m, 4H), 3.81-3.72 (m, 2H), 3.55-3.46 (m, 3H), 2.90-2.82 (m, 1H), 2.75-2.68 (m, 1H), 2.55-2.50 (m, 2H), 2.35-2.20 (m, 1H), 2.09-1.80 (m, 4H), 1.59-1.50 (m, 2H), 1.45 (s, 9H), 1.04 (s, 9H), 1.00-0.96 (m, 2H); ESI-MS m/z 851.00 (M+Na)$^+$.

EXAMPLE 14

Compound IIa-14 tert-butyl N-[(1R,17S,20S,23S)-20-tert-butyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate

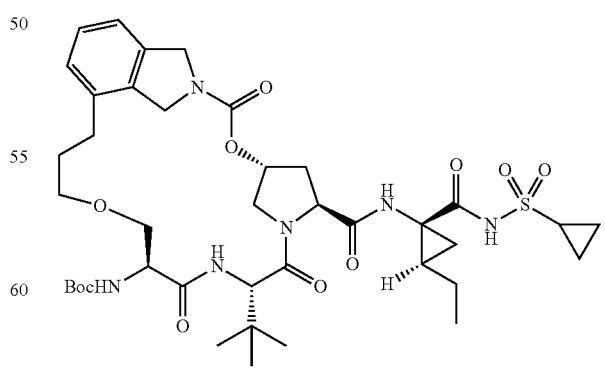

Intermediate C6 in Example 1 was hydrogenated and deprotected by removing Boc group, coupled with A9-1, and then purified to give Compound IIa-14.

Step 1: Preparation of the Intermediate C7-1

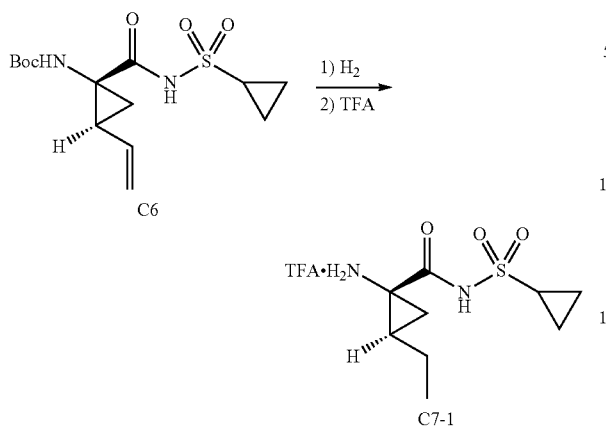

10% Pd/C (80 mg, 20%) was added into a solution of C6 (200 mg, 0.65 mmol) in EA (10 mL). Then the mixture was stirred overnight under $H_2$ at the normal pressure, filtered, concentrated and purified by flash column chromatography to give Boc-C7-1 (120 mg, 58.0%) as white solid.

$^1$H NMR (400 MHz, $CDC_3$) δ 9.68 (brs, 1H), 5.08 (brs, 1H), 2.98-2.92 (m, 1H), 1.60-1.56 (m, 1H), 1.47 (s, 9H), 1.45-1.39 (m, 4H), 1.35-1.29 (m, 2H), 1.11-1.06 (m, 2H), 1.01 (t, J=7.2 Hz, 3H).

Following the procedure in Scheme III, Boc-C7-1 (40 mg, 0.12 mmol) was dissolved in DCM (5 mL) and TFA (1 mL, 20%) was added dropwise. Then the mixture was stirred for 2 hours and concentrated to give Compound C7-1 (42 mg, 97.3%) as brown oil, which was used directly in the next reaction without further purification.

Step 2: Preparation of compound IIa-14

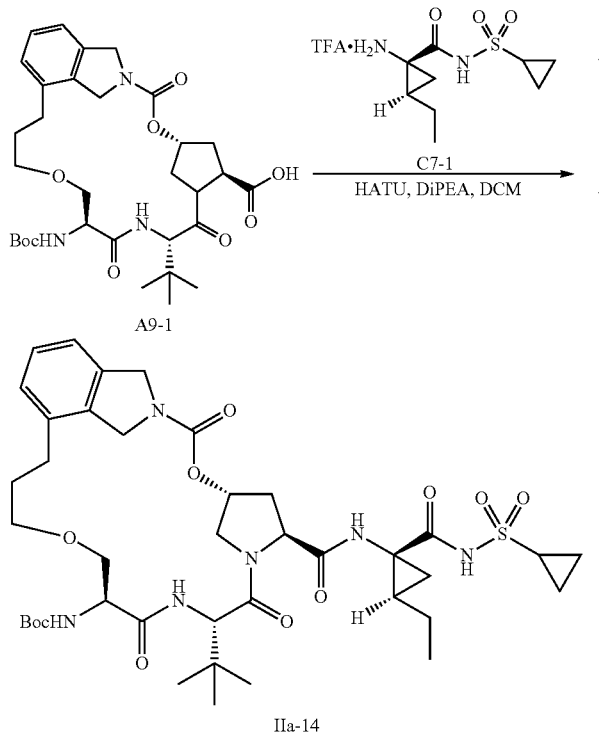

Following the procedure in Scheme IV, left acid fragment A9-1 (80 mg, 0.13 mmol), the amine fragment C7-1 (42 mg, 0.13 mmol), HATU (80 mg, 0.20 mmol) and DiPEA (34 mg, 0.26 mmol) were dissolved in DCM (10 mL). After stirring overnight at the room temperature, water and DCM were added, and the mixture was extracted with DCM (3×). The combined organic layer was washed with water and brine, dried over $Na_2SO_4$, filtered, concentrated and purified by flash column chromatography to give the title compound IIa-14 (4.3 mg, 15.7%) as white powder.

$^1$H NMR (400 MHz, $CDC_3$) δ 7.52 (brs, 1H), 7.33 (brs, 1H), 7.21 (t, J=7.6 Hz, 1H), 7.11 (d, J=7.6 Hz, 1H), 7.05 (d, J=7.6 Hz, 1H), 5.43-5.40 (m, 1H), 5.37 (s, 1H), 4.79-4.67 (m, 4H), 4.54-4.44 (m, 2H), 4.35-4.27 (m, 2H), 3.78-3.75 (m, 2H), 3.54-3.50 (m, 2H), 3.46-3.40 (m, 1H), 2.93-2.90 (m, 1H), 2.69-2.62 (m, 1H), 2.60-2.54 (m, 1H), 2.40-2.33 (m, 1H), 2.22-2.18 (m, 1H), 2.00-1.90 (m, 2H), 1.64-1.60 (m, 2H), 1.54-1.50 (m, 2H), 1.44 (s, 9H), 1.36-1.30 (m, 2H), 1.14-1.10 (m, 2H), 1.04 (s, 9H), 0.96-0.93 (m, 3H); ESI-MS m/z 853.00 (M+Na)$^+$.

EXAMPLE 15

Compound IIa-15 tert-butyl N-[(1R,12E,17S,20S,23S)-20-tert-butyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

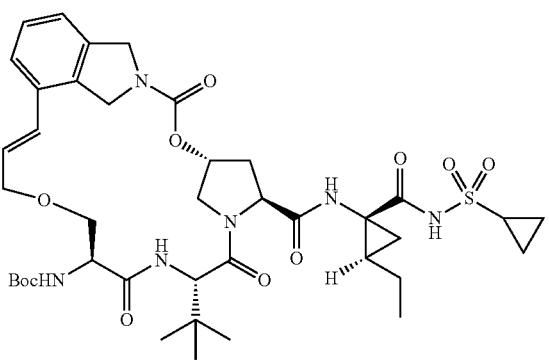 [SMILES: CC[C@@H]1C[C@]1(NC(=O)[C@@H]1C[C@@H]2CN1C(=O)[C@H](C(C)(C)C)NC(=O)[C@@H](NC(=O)OC(C)(C)C)COC/C=C/c1cccc3c1CN(C3)C(=O)O2)C(=O)NS(=O)(=O)C1CC1]

Following the procedure in Scheme IV, left acid fragment A9 (98 mg, 0.16 mmol), the amine fragment C7-1 (56 mg, 0.16 mmol), HATU (92 mg, 0.24 mmol) and DiPEA (342 mg, 0.32 mmol) were dissolved in DCM (10 mL). After stirring overnight at the room temperature, water and DCM were added, and the mixture was extracted with DCM (3×). The combined organic layer was washed with water and brine, dried over $Na_2SO_4$, filtered, concentrated and purified by flash column chromatography to give the title compound IIa-15 (56 mg, 42.4%) as white powder.

$^1$H NMR (400 MHz, $CDC_3$) δ 7.48 (brs, 1H), 7.30-7.24 (m, 2H), 7.16 (d, J=6.4 Hz, 1H), 6.77 (d, J=16.4 Hz, 1H), 6.05 (d, J=16.4 Hz, 1H), 5.58 (d, J=7.2 Hz, 1H), 5.29 (s, 1H), 4.89-4.85 (m, 1H), 4.77-4.71 (m, 3H), 4.46-4.29 (m, 6H), 4.09-4.00 (m, 2H), 3.76-3.73 (m, 1H), 3.46-3.40 (m, 1H), 2.93-2.90 (m, 1H), 2.57-2.50 (m, 1H), 2.40-2.33 (m, 1H), 1.63-1.52 (m, 4H), 1.49 (s, 9H), 1.36-1.18 (m, 5H), 1.05 (s, 9H), 0.96 (t, J=8.0 Hz, 3H); ESI-MS m/z 851.00 (M+Na)$^+$.

EXAMPLE 16

Compound IIa-16 tert-butyl N-[(1R,12E,17S,20S,23S)-20-cyclohexyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

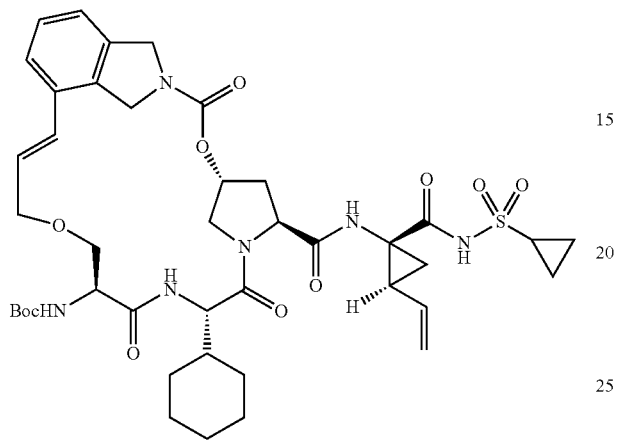

Compound IIa-16 was prepared according to the synthesis procedure of Compound IIa-1, except that N-Boc-L-tert-Leucine was replaced by N-Boc-cyclohexyl-L-Gly-OH.

$^1$H NMR (400 MHz, CDC$_3$) δ 10.09 (brs, 1H), 7.30-7.27 (m, 2H), 7.20-7.16 (m, 2H), 6.76 (d, J=16.0 Hz, 1H), 6.04 (d, J=16.0 Hz, 1H), 5.75-5.70 (m, 1H), 5.55-5.50 (m, 1H), 5.33 (s, 1H), 5.25-5.11 (m, 2H), 4.84-4.74 (m, 4H), 4.42-4.29 (m, 5H), 4.15-4.10 (m, 1H), 4.04-4.00 (m, 1H), 3.95-3.85 (m, 1H), 3.79-3.75 (m, 1H), 3.52-3.48 (m, 1H), 2.92-2.85 (m, 1H), 2.53-2.48 (m, 1H), 2.45-2.40 (m, 1H), 2.02-1.95 (m, 2H), 1.76-1.70 (m, 4H), 1.46 (s, 9H), 1.36-0.98 (m, 12H); ESI-MS m/z 875.00 (M+Na)$^+$.

EXAMPLE 17

Compound IIa-17 tert-butyl N-[(1R,17S,20S,23S)-20-cyclohexyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate

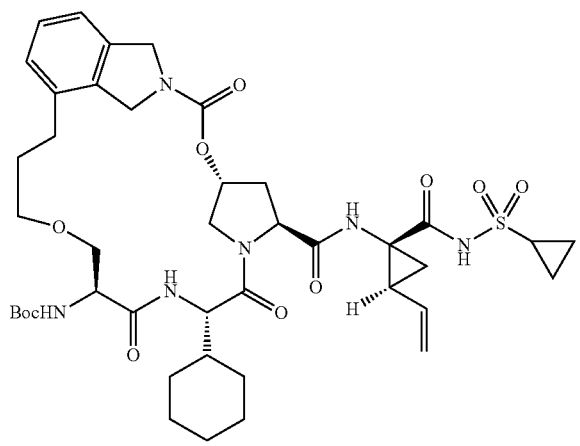 [SMILES: C=C[C@@H]1C[C@]1(NC(=O)[C@@H]1C[C@@H]2CN1C(=O)[C@H](C1CCCCC1)NC(=O)[C@@H](NC(=O)OC(C)(C)C)COCCCc1cccc3c1CN(C3)C(=O)O2)C(=O)NS(=O)(=O)C1CC1]

Compound IIa-17 was prepared according to the synthesis procedure of Compound IIa-13.

$^1$H NMR (400 MHz, CDC$_3$) δ 10.02 (brs, 1H), 7.65 (brs, 1H), 7.40 (brs, 1H), 7.23 (t, J=7.6 Hz, 1H), 7.11 (d, J=7.6 Hz, 1H), 7.05 (d, J=7.6 Hz, 1H), 5.72-5.63 (m, 1H), 5.50 (d, J=7.6 Hz, 1H), 5.41 (s, 1H), 5.25-5.12 (m, 2H), 4.79-4.65 (m, 3H), 4.56-4.48 (m, 2H), 4.39-4.32 (m, 3H), 3.83-3.80 (m, 1H), 3.73-3.71 (m, 1H), 3.56-3.53 (m, 1H), 3.46-3.43 (m, 2H), 2.90-2.86 (m, 1H), 2.74-2.67 (m, 1H), 2.58-2.50 (m, 2H), 2.42-2.36 (m, 1H), 2.07-2.00 (m, 1H), 1.95-1.92 (m, 1H), 1.82-1.65 (m, 6H), 1.44 (s, 9H), 1.37-1.31 (m, 4H), 1.21-1.15 (m, 3H), 1.08-0.98 (m, 5H); ESI-MS m/z 877.00 (M+Na)$^+$.

EXAMPLE 18

Compound IIa-18 tert-butyl N-[(1R,17S,20S,23S)-20-cyclohexyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate

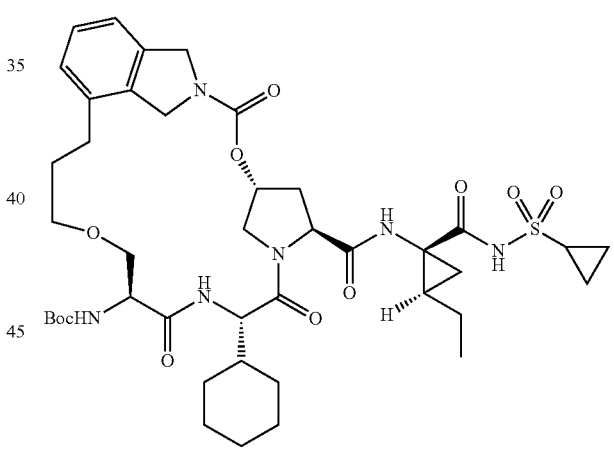

Compound IIa-18 was prepared according to synthesis procedure of Compound IIa-14.

$^1$H NMR (400 MHz, CDC$_3$) δ 10.06 (brs, 1H), 7.55 (brs, 1H), 7.43 (brs, 1H), 7.23 (t, J=7.6 Hz, 1H), 7.11 (d, J=7.6 Hz, 1H), 7.05 (d, J=7.6 Hz, 1H), 5.49 (d, J=7.2 Hz, 1H), 5.40 (s, 1H), 4.78-4.65 (m, 3H), 4.56-4.47 (m, 2H), 4.39-4.31 (m, 3H), 3.83-3.80 (m, 1H), 3.73-3.71 (m, 1H), 3.56-3.54 (m, 1H), 3.46-3.43 (m, 2H), 2.96-2.90 (m, 1H), 2.75-2.68 (m, 1H), 2.58-2.48 (m, 2H), 2.42-2.36 (m, 1H), 2.31-2.17 (m, 2H), 1.79-1.58 (m, 8H), 1.44 (s, 9H), 1.37-1.30 (m, 4H), 1.22-1.15 (m, 3H), 1.13-1.03 (m, 5H), 0.98 (t, J=7.2 Hz, 3H); ESI-MS m/z 879.00 (M+Na)$^+$.

EXAMPLE 19

Compound IIa-19 tert-butyl N-[(1R,12E,17S,20S,23S)-20-cyclohexyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

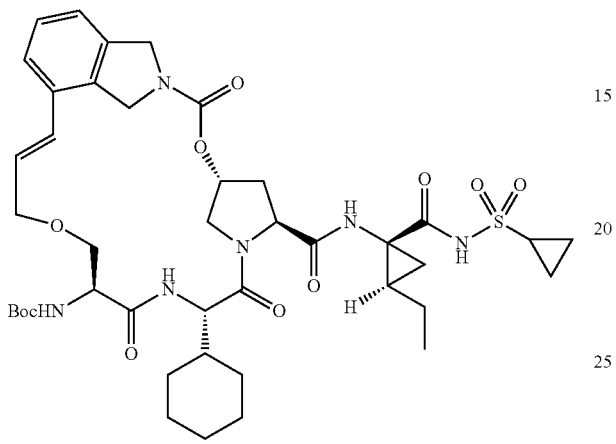

Compound IIa-19 was prepared according to synthesis procedure of Compound IIa-15.

$^1$H NMR (400 MHz, CDC$_3$) δ 10.02 (brs, 1H), 7.32-7.25 (m, 1H), 7.17-7.16 (m, 1H), 6.77 (d, J=16.4 Hz, 1H), 6.05 (d, J=16.4 Hz, 1H), 5.53 (d, J=6.4 Hz, 1H), 5.35 (s, 1H), 4.89-4.86 (m, 1H), 4.78-4.73 (m, 3H), 4.45-4.30 (m, 3H), 4.15-4.11 (m, 1H), 4.05-4.03 (m, 1H), 3.78-3.76 (m, 1H), 3.55-3.51 (m, 1H), 2.99-2.91 (m, 1H), 2.58-2.52 (m, 1H), 2.48-2.41 (m, 1H), 1.81-1.57 (m, 8H), 1.48 (s, 9H), 1.41-1.32 (m, 5H), 1.22-1.15 (m, 3H), 1.09-1.03 (m, 4H), 0.98 (t, J=7.2 Hz, 3H); ESI-MS m/z 879.00 (M+Na)$^+$.

EXAMPLE 20

Compound IIa-20 tert-butyl N-[(1R,12E,18S,21S,24S)-21-cyclohexyl-24-{[(1R,2S)-1-[(cyclopropanesulfonyl)carbamoyl]-2-ethenylcyclopropyl]carbamoyl}-3,19,22-trioxo-2,15-dioxa-4,20,23-triazatetracyclo[20.2.1.1$^{4,7}$.0$^{6,11}$]heptacosa-6,8,10,12-tetraen-18-yl]carbamate

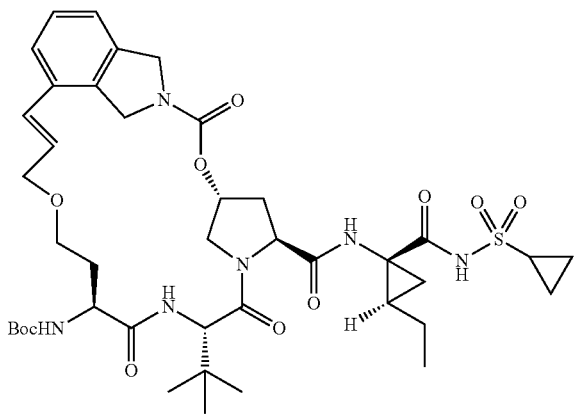 [SMILES: CC[C@@H]1C[C@]1(NC(=O)[C@@H]1C[C@@H]2CN1C(=O)[C@H](C(C)(C)C)NC(=O)[C@@H](NC(=O)OC(C)(C)C)CCOC/C=C/c1cccc3c1CN(C3)C(=O)O2)C(=O)NS(=O)(=O)C1CC1]

Compound IIa-20 was prepared according to the synthesis procedure of Compound IIa-1, except that N-Boc-L-Serine methyl ester was replaced by N-Boc-L-Homoserine methyl ester.

$^1$H NMR (400 MHz, CDC$_3$) δ 7.57 (brs, 1H), 7.28-7.25 (m, 2H), 7.16 (d, J=7.2 Hz, 1H), 6.52 (d, J=18.0 Hz, 1H), 6.04 (d, J=18.0 Hz, 1H), 5.67-5.55 (m, 1H), 5.46-5.40 (m, 2H), 5.34-5.12 (m, 2H), 4.75-4.61 (m, 6H), 4.45-4.40 (m, 2H), 4.25-4.22 (m, 2H), 4.06-4.00 (m, 2H), 3.93-3.90 (m, 1H), 3.50-3.47 (m, 2H), 2.89-2.85 (m, 1H), 2.57-2.50 (m, 1H), 2.38-2.31 (m, 1H), 2.17-2.08 (m, 2H), 1.85-1.80 (m, 1H), 1.43 (s, 9H), 1.40-1.20 (m, 6H), 1.06 (s, 9H); ESI-MS m/z 863.05 (M+Na)$^+$.

EXAMPLE 21

Compound IIa-21 tert-butyl N-[(1R,12E,17R,20S,23S)-20-tert-butyl-23-{[(1R,2S)-1-[(cyclopropanesulfonyl)carbamoyl]-2-ethenylcyclopropyl]carbamoyl}-3,18,21-trioxo-2-oxa-15-thia-4,19,22-triazatetracyclo[20.2.1.1$^{4,7}$.0$^{6,11}$]hexacosa-6,8,10,12-tetraen-17-yl]carbamate

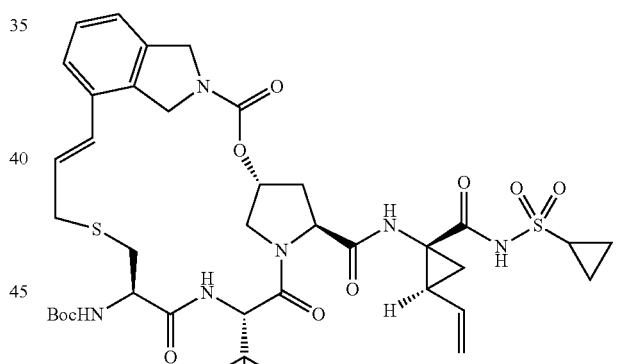

Compound IIa-21 was prepared according to the synthesis procedure of Compound IIa-1, except that N-Boc-L-Serine methyl ester was replaced by N-Boc-L-Cysteine methyl ester.

$^1$H NMR (400 MHz, CDC$_3$) δ 9.96 (brs, 1H), 7.64 (brs, 1H), 7.39-7.25 (m, 2.7H), 7.18-7.16 (m, 1.3H), 6.19 (d, J=15.6 Hz, 1H), 5.75-5.65 (m, 1H), 5.54 (brs, 1H), 5.32-5.13 (m, 2H), 5.07 (d, J=7.2 Hz, 1H), 4.79-4.68 (m, 4H), 4.56-4.53 (m, 3H), 4.39 (d, J=11.2 Hz, 1H), 4.26 (brs, 1H), 3.80-3.76 (m, 1H), 3.13 (d, J=7.6 Hz, 2H), 3.03-3.00 (m, 1H), 2.93-2.87 (m, 1H), 2.50-2.43 (m, 1H), 2.37-2.30 (m, 1H), 2.01-1.94 (m, 1H), 1.48 (s, 9H), 1.45-1.39 (m, 2H), 1.39-1.27 (m, 4H), 1.05 (s, 9H); ESI-MS m/z 865.00 (M+Na)$^+$.

EXAMPLE 22

Compound IIa-22 tert-butyl N-[(1R,12E,17S,20S,23S)-20-cyclopentyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate

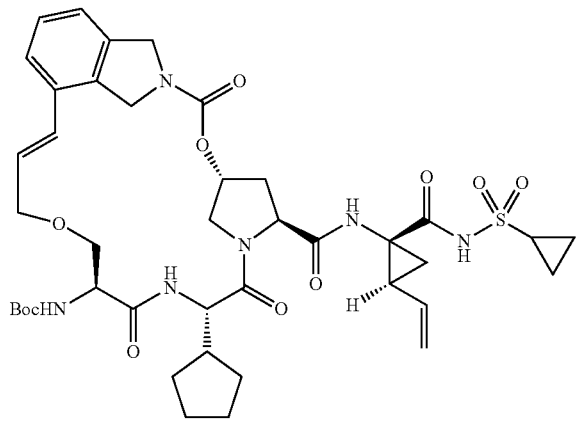 [SMILES: C=C[C@@H]1C[C@]1(NC(=O)[C@@H]1C[C@@H]2CN1C(=O)[C@H](C1CCCC1)NC(=O)[C@@H](NC(=O)OC(C)(C)C)COC/C=C/c1cccc3c1CN(C3)C(=O)O2)C(=O)NS(=O)(=O)C1CC1]

Compound IIa-22 was prepared according to the synthesis procedure of Compound IIa-1, except that N-Boc-L-tert-Leucine was replaced by N-Boc-cyclopentyl-L-Gly-OH.

$^1$H NMR (400 MHz, CDC$_3$) δ 10.00 (brs, 1H), 7.66-7.57 (m, 1H), 7.33-7.23 (m, 2H), 7.17-7.13 (m, 2H), 6.69-6.53 (m, 1H), 6.01-5.78 (m, 3H), 5.52-5.10 (m, 4H), 4.85-4.67 (m, 4H), 4.51-4.18 (m, 6H), 3.90-3.81 (m, 2H), 3.61-3.34 (m, 1H), 2.92-2.85 (m, 1H), 2.56-2.50 (m, 1H), 2.40-2.36 (m, 1H), 2.09-1.99 (m, 2H), 1.78-1.72 (m, 2H), 1.60-1.55 (m, 4H), 1.49 (s, 9H), 1.46-1.35 (m, 4H), 1.13-1.01 (m, 4H); ESI-MS m/z 861.00 (M+Na)$^+$.

EXAMPLE 23

Compound IIb-1 tert-butyl N-[(3R,5S,8S,11S,15E)-8-tert-butyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),15,17(25),18,20(24),21-hexaen-11-yl]carbamate

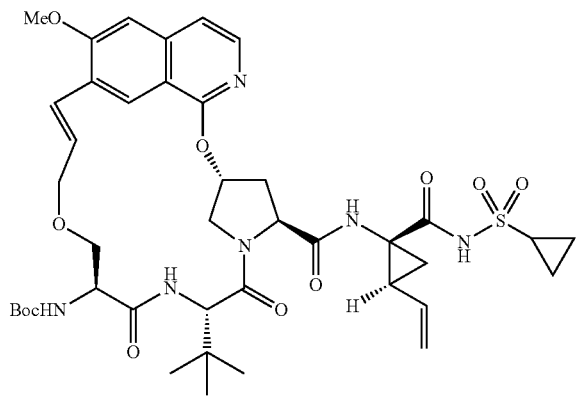 [SMILES: C=C[C@@H]1C[C@]1(NC(=O)[C@@H]1C[C@@H]2CN1C(=O)[C@H](C(C)(C)C)NC(=O)[C@@H](NC(=O)OC(C)(C)C)COC/C=C/c1cc3c(nccc3cc1OC)O2)C(=O)NS(=O)(=O)C1CC1]

Compound IIb-1 was prepared by Schemes II, III, and IV.

Intermediate B2: (2S,4R)-1-tert-butyl 2-methyl 4-(7-bromo-6-methoxyisoquinolin-1-yloxy)pyrrolidine-1,2-dicarboxylate

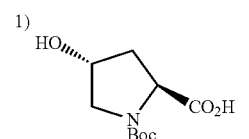

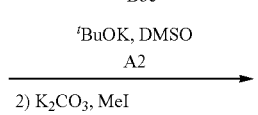

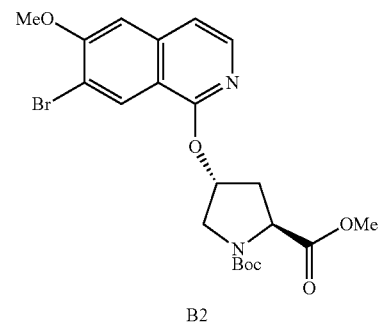

Following the procedure in Scheme II, material A2 (466 mg, 2.01 mmol) was dissolved in DMSO (10 m L). $^t$BuOK (616 mg, 5.49 mmol) was added in small portions with stirring. After stirring for a further 20 min at the room temperature, a solution of B1 (500 mg, 1.83 mmol, prepared according to WO2008/051475) in DMSO was added dropwise. The mixture was stirred for another 2 h at r.t. and 2N HCl was added to adjust the pH to 1 to 2. Then the mixture was extracted with EtOAc (3×). The combined organic layer was washed with water and brine, dried over Na$_2$SO$_4$, filtered and concentrated to give the crude acid A3 (600 mg, 70.6%), which was used directly in the next reaction without further purification.

The crude acid (4.0 g, 8.62 mmol) was dissolved in DMF (50 mL). K$_2$CO$_3$ (2.38 g, 17.24 mmol) was added in small portions with stirring. Then CH$_3$I (1.59 g, 11.2 mmol) was added dropwise. The mixture was stirred for another 1 h at r.t. and the reaction solution was added into water. Then the mixture was extracted with EtOAc (3×). The combined organic layer was washed with water and brine, dried over Na$_2$SO$_4$, filtered, concentrated and purified by flash column chromatography to give the intermediate B2 (3.7 g, 89.4%).

$^1$H NMR (400 MHz, CDCl$_3$) δ 8.22 (s, 1H), 7.81-7.79 (m, 1H), 7.00-6.98 (m, 1H), 6.89 (s, 1H), 5.67-5.64 (m, 1H), 4.51-4.44 (m, 1H), 3.89-3.87 (m, 5H), 3.69 (s, 3H), 2.53-2.45 (m, 1H), 2.29-2.22 (m, 1H), 1.37 (s, 9H).

Intermediate B3: (2S,4R)-1-tert-butyl 2-methyl 4-(6-methoxy-7-vinylisoquinolin-1-yloxy)pyrrolidine-1,2-dicarboxylate

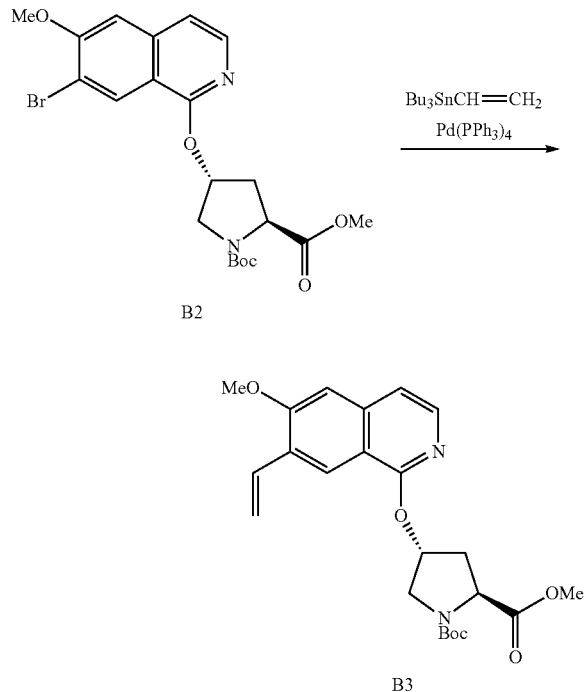

The above bromide B2 (1.1 g, 2.29 mmol) was dissolved in toluene (25 mL). Bu$_3$SnCH=CH$_2$ (1.09 g, 3.44 mmol) and Pd(PPh$_3$)$_4$ (264 mg, 0.229 mmol) were added. The mixture was refluxed for 5 h under N$_2$. After cooled to r.t., the mixture was filtered, concentrated and purified by flash column chromatography to give the intermediate B3 (0.84 g, 86.0%).

$^1$H NMR (400 MHz, CDC$_3$) δ 8.18 (s, 1H), 7.87-7.84 (m, 1H), 7.11-7.09 (m, 2H), 6.98 (s, 1H), 5.93 (d, J=17.2 Hz, 1H), 5.77-5.75 (m, 1H), 5.4 (d, J=11.6 Hz, 1H), 4.62-4.51 (m, 1H), 3.97-3.93 (m, 5H), 3.78 (s, 3H), 2.66-2.58 (m, 1H), 2.39-2.35 (m, 1H), 1.44 (s, 9H).

Intermediate B4: (2S,4R)-methyl 1-((S)-2-(tert-butoxycarbonylamino)-3,3-dimethylbutanoyl)-4-(6-methoxy-7-vinylisoquinolin-1-yloxy)pyrrolidine-2-carboxylate

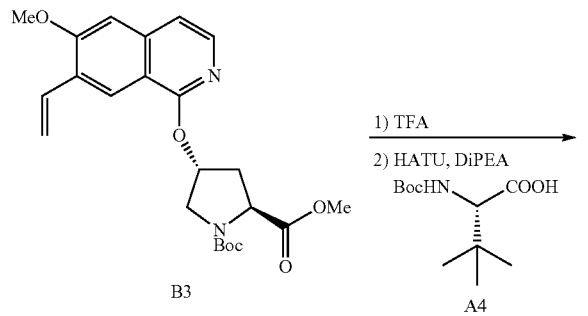

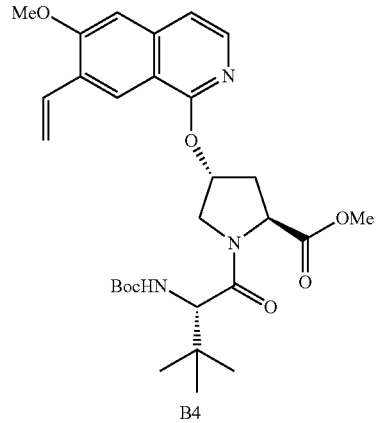

Following the procedure in Scheme II, B3 (840 mg, 1.96 mmol) was dissolved in DCM (10 mL) and CF$_3$COOH (3 mL) was added dropwise in ice bath. After stirring for 3 h, the mixture was concentrated and Na$_2$CO$_3$ solution was added. Then the mixture was extracted with EA (3×). The combined organic layer was washed with water and brine, dried over Na$_2$SO$_4$, filtered, concentrated to give crude deprotected compound (550 mg, 86%) as brown oil, which was used directly in the next reaction without further purification.

N-BocLeu (636 mg, 2.75 mmol), deprotected compound (900 mg, 2.75 mmol), HATU (1.36 g, 3.57 mmol) and DiPEA (460 mg, 3.57 mmol) were dissolved in DCM (15 mL). After stirring overnight at the room temperature, water was added and the mixture was extracted with DCM (3×). The combined organic layer was washed with water and brine, dried over Na$_2$SO$_4$, filtered, concentrated and purified by flash column chromatography to give the title compound B4 (810 mg, 54.5%) as brown oil.

ESI-MS m/z 564.0 (M+H)$^+$.

Intermediate B5: (2S,4R)-methyl 1-((S)-2-((S)-3-(allyloxy)-2-(tert-butoxycarbonylamino)propanamido)-3,3-dimethylbutanoyl)-4-(6-methoxy-7-vinylisoquinolin-1-yloxy)pyrrolidine-2-carboxylate

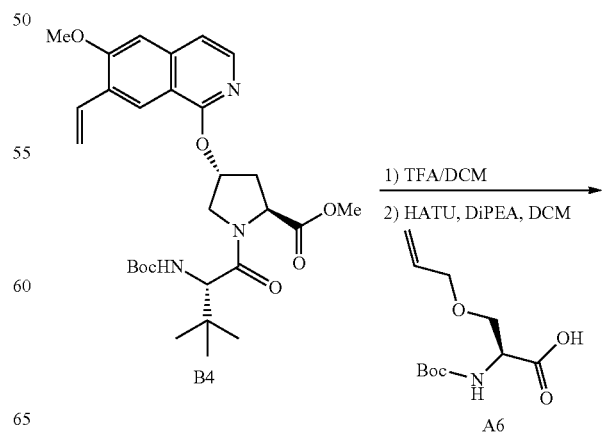

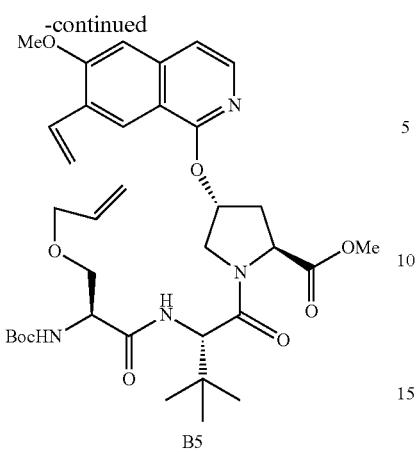

B5

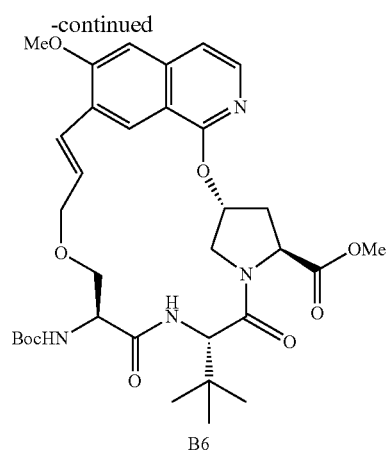

B6

Following the procedure in Scheme II, B4 (810 mg, 1.5 mmol) was dissolved in DCM (12 mL) and TFA (2.5 mL) was added dropwise. Then the mixture was stirred for 2 h at the room temperature and concentrated. Water and DCM was added and the pH was adjusted to ~12 with 2N NaOH. The mixture was extracted with DCM (3×). The combined organic layer was washed with brine, dried over $Na_2SO_4$, filtered and concentrated to give the crude Boc-removed product, which was used directly in the next reaction without further purification.

Amino acid A6 (363 mg, 1.48 mmol), the crude Boc-removed product (652 mg, 1.48 mmol), HATU (732 mg, 1.92 mmol) and DiPEA (248 mg, 1.92 mmol) were dissolved in DCM (20 mL). After stirring overnight at the room temperature, water and DCM were added, and the mixture was extracted with DCM (3×). The combined organic layer was washed with water and brine, dried over $Na_2SO_4$, filtered, concentrated and purified by flash column chromatography to give the title compound B5 (830 mg, 84.07%) as light yellow oil.

ESI-MS m/z 691.50 $(M+Na)^+$.

Intermediate B6: tert-butyl N-[(3R,5S,8S,11S,15E)-8-tert-butyl-5-methoxylcarbonyl-18-methoxy-7,10-dioxo-2,13-dioxa-6,9,23-triazatetracyclo[15.6.2.13, 6.020,24]hexacosa-1(23),15,17(25), 18,20(24),21-hexaen-11-yl]carbamate Following the procedure in Scheme 2, B5 (830 mg, 1.244 mmol) was dissolved in DCM (340 mL) and Zhan catalyst (90 mg, 0.124 mmol) was added. Then the mixture was stirred overnight at r.t. To the mixture was added 0.1 mL DMSO. Then the mixture was concentrated and purified by flash column chromatography to give the title compound B6 (540 mg, 68.0%). ESI-MS m/z 663.50 $(M+Na)^+$.

Intermediate B7: tert-butyl N-[(3R,5S,8S,11S,15E)-8-tert-butyl-5-hydroxylcarbonyl-18-methoxy-7,10-dioxo-2,13-dioxa-6,9,23-triazatetracyclo[15.6.2.13, 6.020,24]hexacosa-1(23),15,17(25), 18,20(24),21-hexaen-11-yl]carbamate

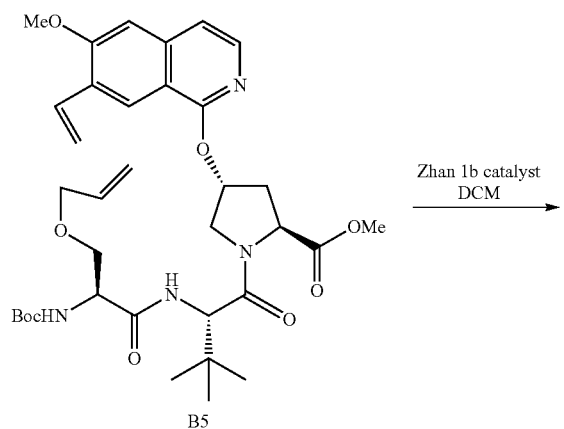

B5

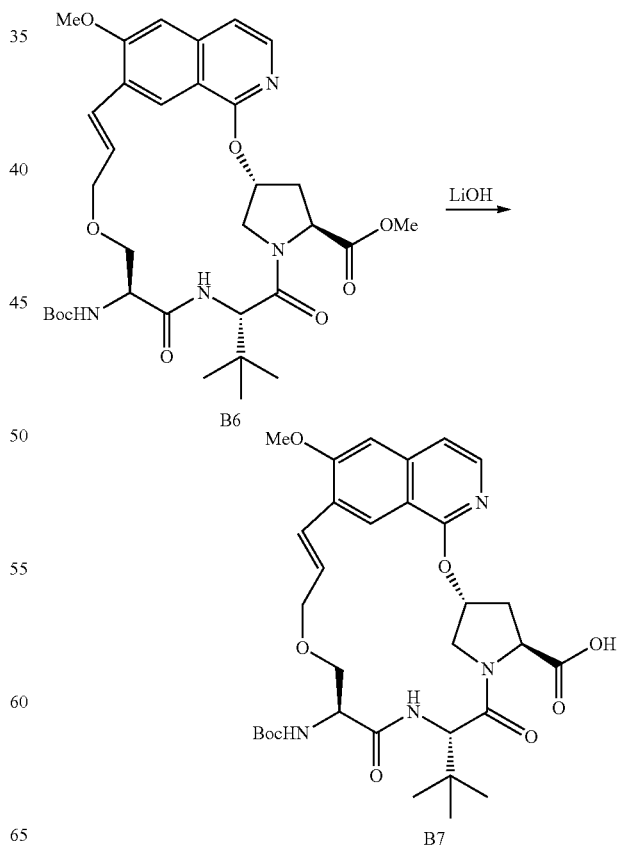

B6

B7

Following the procedure in Scheme II, intermediate B7 (170 mg, 0.266 mmol) was added in a solution of LiOH (67 mg, 1.6 mmol) in a mixture of MeOH/THF/H$_2$O (4 mL/4 mL/1 mL). After stirring for 1 h at r.t. the pH was adjusted to ~4 with 1N HCl, the water layer was separated, and the mixture was extracted with EA (2×). The combined organic layer was washed with brine, dried over Na$_2$SO$_4$, filtered and concentrated to give the title compound B7 (160 mg, 100%) as light yellow oil, which was used directly in the next reaction without further purification.

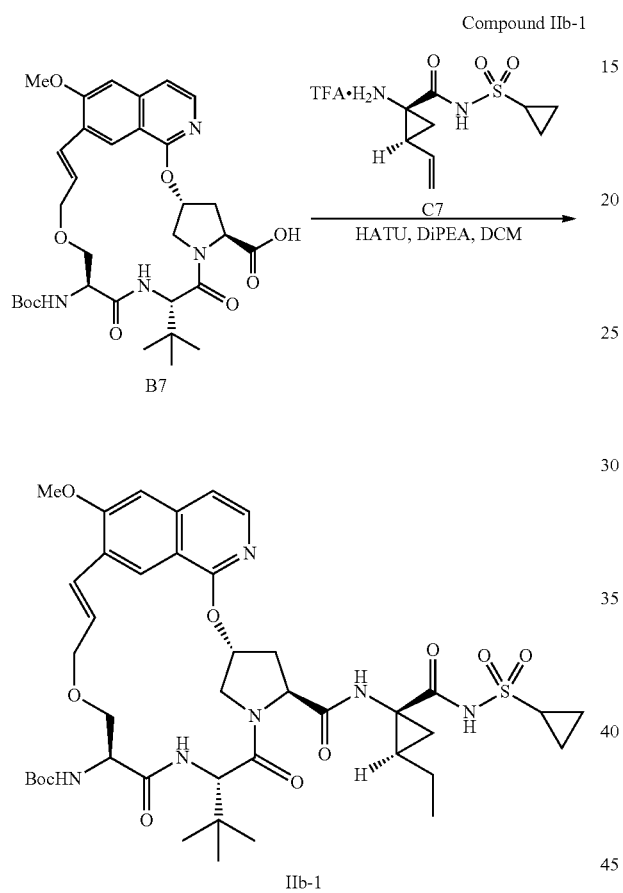

Following the procedure in Scheme IV, left acid fragment B7 (160 mg, 0.255 mmol), amine fragment C7 (64 mg, 0.280 mmol), HATU (126 mg, 0.331 mmol) and DiPEA (43 mg, 0.331 mmol) were dissolved in DCM (6 mL). After stirring overnight at the room temperature, water and DCM were added, and the mixture was extracted with DCM (3×). The combined organic layer was washed with water and brine, dried over Na$_2$SO$_4$, filtered, concentrated and purified by flash column chromatography to give the title compound IIb-1 (26 mg, 12.0%) as white powder.

$^1$H NMR (400 MHz, CDC$_3$) δ 8.47 (s, 1H), 7.87 (d, J=5.6 Hz, 1H), 7.52 (d, J=6.0 Hz, 1H), 7.36 (s, 1H), 7.12 (d, J=5.6 Hz, 1H), 6.94 (s, 1H), 6.90 (d, J=15.6 Hz, 1H), 6.35-6.28 (m, 1H), 5.71-5.61 (m, 3H), 5.22 (d, J=16.8 Hz, 1H), 5.11 (d, J=10.8 Hz, 1H), 4.60-4.53 (m, 2H), 4.45-4.40 (m, 1H), 4.34-4.26 (m, 2H), 4.04-3.89 (m, 6H), 2.90-2.86 (m, 1H), 2.78-2.73 (m, 1H), 2.47-2.41 (m, 1H), 2.05-1.99 (m, 2H), 1.93-1.90 (m, 1H), 1.45 (s, 9H), 1.42-1.38 (m, 2H), 1.08 (s, 9H) 1.02-0.98 (m, 2H); ESI-MS m/z 861.00 (M+Na)$^+$.

EXAMPLE 24

Compound IIb-2 tert-butyl N-[(3R,5S,8S,11S)-8-tert-butyl-5-{[(1R,2S)-1-[(cyclopropanesulfonyl)carbamoyl]-2-ethenyl-cyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),17(25),18,20(24),21-pentaen-11-yl] carbamate

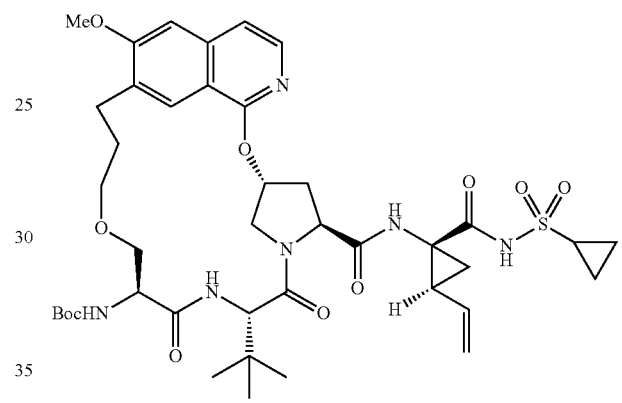

Compound B6 in example 23 was hydrogenated and hydrolyzed, then coupled with right fragment C7, and purified to give Compound IIb-2.

Step 1: Preparation of the Intermediate B7-1

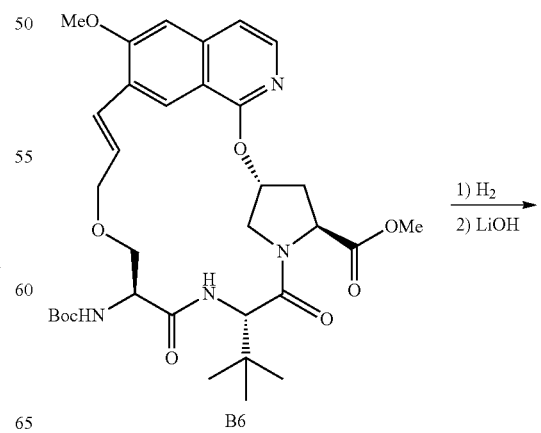

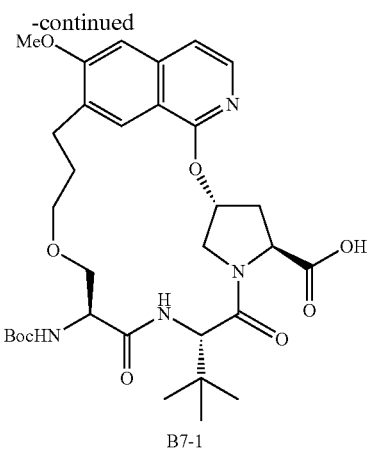

10% Pd/C (80 mg, 10%) was added in a solution of B6 (170 mg, 0.271 mmol) in EA (30 mL). Then the mixture was stirred for 3 h under $H_2$, filtered and concentrated to the crude hydrogenated product as light yellow oil, which was used directly in the next reaction without further purification.

The hydrogenated product was added in a solution of LiOH (64 mg, 1.527 mmol) in MeOH/THF/$H_2O$ (4 mL/4 mL/1 mL). After stirring for 2 h at r.t., the pH was adjusted to ~4 with 1N HCl and the mixture was extracted with EA (2×). The combined organic layer was washed with brine, dried over $Na_2SO_4$, filtered and concentrated to give the light yellow oil B7-1 (150 mg, 96.0%), which was used directly in the next reaction without further purification.

Step 2: Preparation of Compound IIb-2

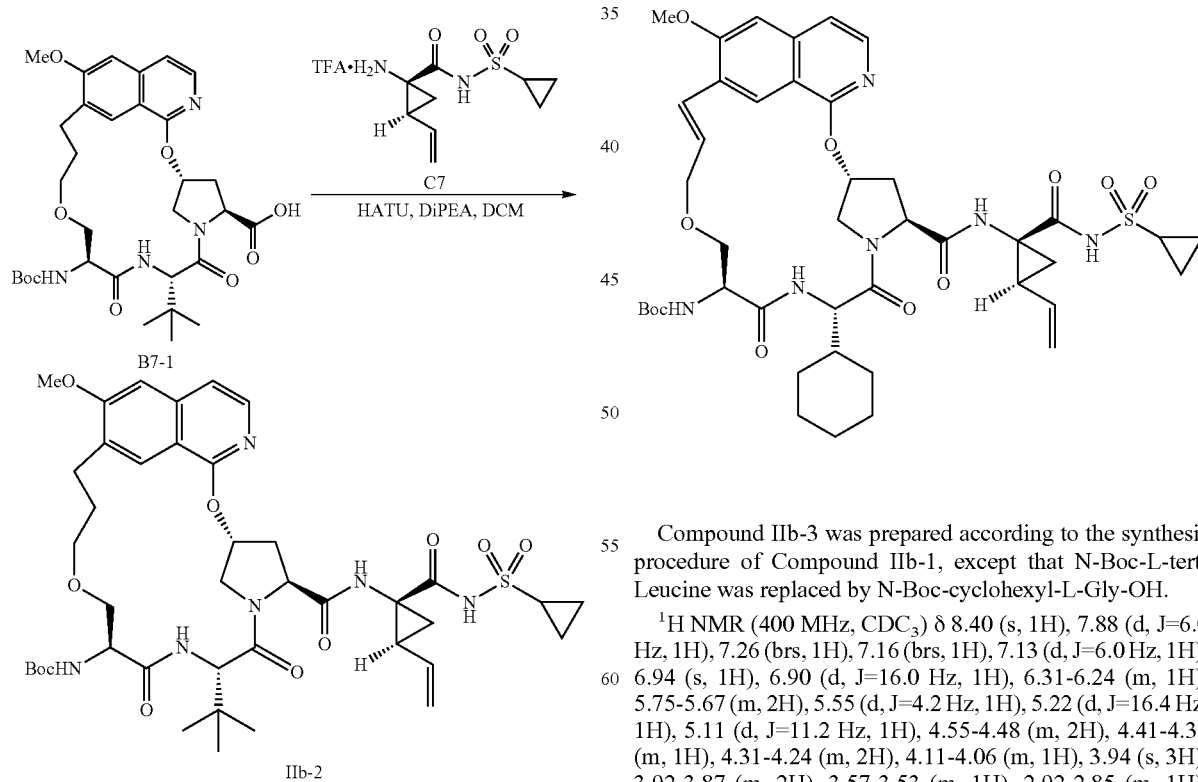

Following the procedure in Scheme IV, left acid fragment B7-1 (150 mg, 0.238 mmol), the amine fragment C7 (118 mg, 0.309 mmol), HATU (126 mg, 0.331 mmol) and DiPEA (46 mg, 0.357 mmol) were dissolved in DCM (6 mL). After stirring overnight at the room temperature, water and DCM were added. Then the mixture was extracted with DCM (3×). The combined organic layer was washed with water and brine, dried over $Na_2SO_4$, filtered, concentrated and purified by flash column chromatography to give the title compound IIb-2 (80 mg, 52.5%) as white powder.

$^1$H NMR (400 MHz, $CDC_3$) δ 7.86 (d, J=6.0 Hz, 1H), 7.82 (s, 1H), 7.60 (brs, 1H), 7.30 (d, J=8.8 Hz, 1H), 7.13 (d, J=6.0 Hz, 1H), 6.94 (s, 1H), 5.73 (brs, 1H), 5.69-5.64 (m, 1H), 5.48 (d, J=7.6 Hz, 1H), 5.23 (d, J=16.8 Hz, 1H), 5.12 (d, J=10.4 Hz, 1H), 4.85 (d, J=8.8 Hz, 1H), 4.50-4.47 (m, 2H), 4.40-4.37 (m, 2H), 3.92-3.87 (m, 4H), 3.64-3.60 (m, 2H), 3.37-3.30 (m, 2H), 2.87-2.72 (m, 3H), 2.45-2.39 (m, 1H), 2.06-1.99 (m, 1H), 1.95-1.89 (m, 3H), 1.44 (s, 9H), 1.40-1.36 (m, 2H), 1.06 (s, 9H), 1.02-0.98 (m, 4H); ESI-MS m/z 863.00 $(M+Na)^+$.

EXAMPLE 25

Compound IIb-3 tert-butyl N-[(3R,5S,8S,11S,15E)-8-cyclohexyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo [15.6.2.1$^{3,6}$.0$^{20,24}$]hexacosa-1(23),15,17(25),18,20(24),21-hexaen-11-yl]carbamate Compound IIb-3 was prepared according to the synthesis procedure of Compound IIb-1, except that N-Boc-L-tert-Leucine was replaced by N-Boc-cyclohexyl-L-Gly-OH.

$^1$H NMR (400 MHz, $CDC_3$) δ 8.40 (s, 1H), 7.88 (d, J=6.0 Hz, 1H), 7.26 (brs, 1H), 7.16 (brs, 1H), 7.13 (d, J=6.0 Hz, 1H), 6.94 (s, 1H), 6.90 (d, J=16.0 Hz, 1H), 6.31-6.24 (m, 1H), 5.75-5.67 (m, 2H), 5.55 (d, J=4.2 Hz, 1H), 5.22 (d, J=16.4 Hz, 1H), 5.11 (d, J=11.2 Hz, 1H), 4.55-4.48 (m, 2H), 4.41-4.36 (m, 1H), 4.31-4.24 (m, 2H), 4.11-4.06 (m, 1H), 3.94 (s, 3H), 3.92-3.87 (m, 2H), 3.57-3.53 (m, 1H), 2.92-2.85 (m, 1H), 2.73-2.68 (m, 1H), 2.54-2.47 (m, 1H), 2.01-1.95 (m, 2H), 1.86-1.67 (m, 1H), 1.45 (s, 9H), 1.37-1.29 (m, 4H), 1.15-0.99 (m, 4H); ESI-MS m/z 887.00 $(M+Na)^+$.

EXAMPLE 26

Compound IIb-4 tert-butyl N-[(3R,5S,8S,11S)-8-cyclohexyl-5-{[(1R,2S)-1-[(cyclopropanesulfonyl)carbamoyl]-2-ethenyl-cyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),17(25),18,20(24),21-pentaen-11-yl]carbamate

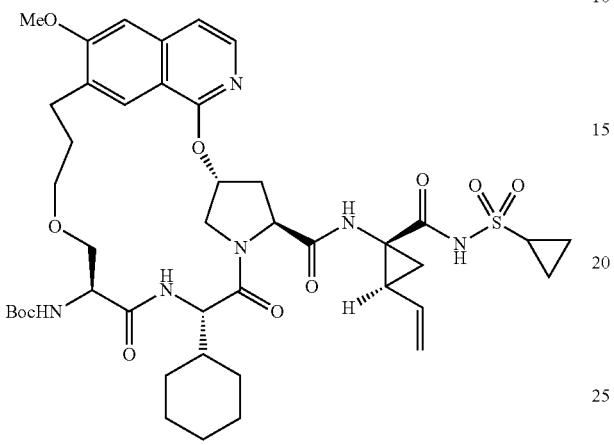

Compound IIb-4 was prepared according to the synthesis procedure of Compound IIb-2, except that N-Boc-L-tert-Leucine was replaced by N-Boc-cyclohexyl-L-Gly-OH.

$^1$H NMR (400 MHz, CDC$_3$) δ 7.87 (d, J=6.0 Hz, 1H), 7.82 (s, 1H), 7.63 (brs, 1H), 7.39 (brs, 1H), 7.13 (d, J=6.0 Hz, 1H), 6.94 (s, 1H), 5.80 (brs, 1H), 5.72-5.64 (m, 1H), 5.51 (d, J=7.6 Hz, 1H), 5.23 (d, J=17.2 Hz, 1H), 5.12 (d, J=10.4 Hz, 1H), 4.72-4.68 (m, 1H), 4.54 (d, J=11.6 Hz, 1H), 4.42-4.38 (m, 2H), 3.94-3.92 (m, 1H), 3.92 (s, 3H), 3.63 (d, J=4.0 Hz, 2H), 3.38-3.29 (m, 2H), 2.89-2.83 (m, 2H), 2.77-2.71 (m, 2H), 2.50-2.43 (m, 1H), 2.03-1.97 (m, 2H), 1.93-1.85 (m, 4H), 1.75-1.65 (m, 4H), 1.43 (s, 9H), 1.32-1.27 (m, 4H), 1.07-0.99 (m, 4H); ESI-MS m/z 889.00 (M+Na)$^+$.

EXAMPLE 27

Compound IIb-5 tert-butyl N-[(3R,5S,8S,11S,15E)-8-cyclohexyl-5-{[(1R,2R)-1-[(cyclopropanesulfonyl)carbamoyl]-2-ethylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),15,17(25),18,20(24),21-hexaen-11-yl]carbamate

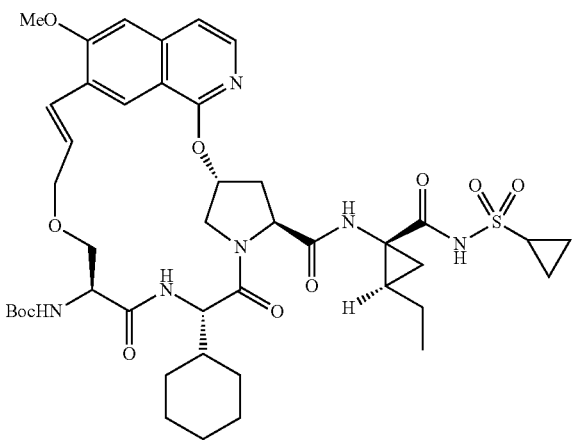 [SMILES: CC[C@@H]1C[C@]1(NC(=O)[C@@H]1C[C@@H]2CN1C(=O)[C@H](C1CCCCC1)NC(=O)[C@@H](NC(=O)OC(C)(C)C)COC/C=C/c1cc3c(nccc3cc1OC)O2)C(=O)NS(=O)(=O)C1CC1]

Compound IIb-5 was prepared according to the synthesis procedure of Compound IIb-1, except that fragment C7 was replaced by fragment C7-1.

$^1$H NMR (400 MHz, CDC$_3$) δ 10.02 (s, 1H), 8.43 (s, 1H), 7.91 (d, J=6.0 Hz, 1H), 7.19 (d, J=6.0 Hz, 1H), 7.07 (brs, 1H), 6.98 (s, 1H), 6.92 (d, J=16.0 Hz, 1H), 6.32-6.24 (m, 1H), 5.78 (brs, 1H), 5.60 (d, J=8.0 Hz, 1H), 4.60-4.48 (m, 2H), 4.47-4.30 (m, 3H), 4.11-4.06 (m, 1H), 3.97 (s, 3H), 3.95-3.91 (m, 2H), 3.56-3.50 (m, 1H), 2.94-2.90 (m, 1H), 2.80-2.73 (m, 1H), 2.60-2.50 (m, 1H), 1.93-1.65 (m, 10H), 1.48 (s, 9H), 1.32-1.27 (m, 6H), 1.16-1.06 (m, 4H), 0.95 (t, J=7.2 Hz, 3H); ESI-MS m/z 888.75 (M+Na)$^+$.

EXAMPLE 28

Compound IIb-6 tert-butyl N-[(3R,5S,8S,11S)-8-cyclohexyl-5-{[(1R,2S)-1-[(cyclopropanesulfonyl)carbamoyl]-2-ethylcyclopropyl]carbamoyl}-18-methoxy-7,10-dioxo-2,13-dioxa-6,9,23-triazatetracyclo[15.6.2.1$^{3,6}$.0$^{20,24}$]hexacosa-1(23),17(25),18,20(24),21-pentaen-11-yl]carbamate

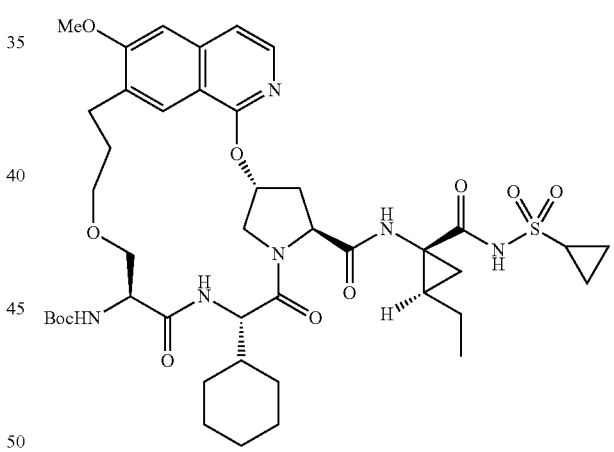

Compound IIb-6 was prepared according to the synthesis procedure of Compound IIb-4, except that fragment C7 was replaced by fragment C7-1.

$^1$H NMR (400 MHz, CDC$_3$) δ 10.06 (s, 1H), 7.90 (d, J=6.0 Hz, 1H), 7.86 (s, 1H), 7.18 (d, J=6.0 Hz, 1H), 6.98 (s, 1H), 5.86 (brs, 1H), 5.51 (brs, 1H), 4.70-4.60 (m, 1H), 4.58 (d, J=10.8 Hz, 1H), 4.50-4.42 (m, 2H), 3.99-3.97 (m, 1H), 3.94 (s, 3H), 3.63 (d, J=4.0 Hz, 2H), 3.37-3.30 (m, 2H), 2.94-2.89 (m, 2H), 2.78-2.71 (m, 2H), 2.54-2.48 (m, 1H), 2.00-1.50 (m, 10H), 1.45 (s, 9H), 1.39-1.20 (m, 8H), 1.07-0.99 (m, 4H), 0.96 (t, J=7.2 Hz, 3H); ESI-MS m/z 866.69 (M−H)$^-$.

EXAMPLE 29

Compound IIb-7 tert-butyl N-[(3R,5S,8S,11S,15E)-8-cyclohexyl-5-{[(1R,2S)-1-hydroxycarbonyl-2-ethenylcyclopropyl]carbamoyl}-18-methoxy-7,10-dioxo-2,13-dioxa-6,9,23-triazatetracyclo[15.6.2.13,6.020,24]hexacosa-1(23),15,17(25),18,20(24),21-hexaen-11-yl]carbamate

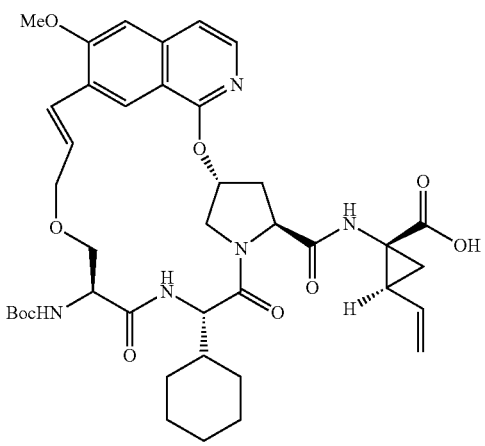 [SMILES: C=C[C@@H]1C[C@]1(NC(=O)[C@@H]1C[C@@H]2CN1C(=O)[C@H](C1CCCCC1)NC(=O)[C@@H](NC(=O)OC(C)(C)C)COC/C=C/c1cc3c(nccc3cc1OC)O2)C(=O)O]

Compound IIb-7 was prepared according to the synthesis procedure of Compound IIb-1, except that fragment C7 was replaced by fragment C5 followed by condensation and hydrolysis.

$^1$H NMR (400 MHz, CDC$_3$) δ 8.27 (s, 1H), 7.83 (d, J=5.2 Hz, 1H), 7.50 (brs, 1H), 7.32 (d, J=6.0 Hz, 1H), 7.08 (d, J=5.2 Hz, 1H), 6.89 (s, 1H), 6.82 (d, J=16.0 Hz, 1H), 6.21-6.15 (m, 1H), 5.71-5.64 (m, 2H), 5.52 (d, J=7.2 Hz, 1H), 5.22-5.04 (m, 2H), 4.60-4.48 (m, 2H), 4.42 (d, J=9.6 Hz, 1H), 4.23-4.20 (m, 1H), 4.11 (d, J=6.0 Hz, 2H), 3.88 (s, 3H), 3.80-3.70 (m, 2H), 3.43 (t, J=7.2 Hz, 1H), 2.80-2.73 (m, 1H), 2.60-2.50 (m, 1H), 1.98-1.88 (m, 2H), 1.73-1.50 (m, 8H), 1.45 (s, 9H), 1.18-1.01 (m, 4H); ESI-MS m/z 760.00 (M−H)$^-$.

EXAMPLE 30

Biological Activity Assays

Compounds of formuala (I) are tested for the ability to inhibit viral replication of the Hepatitis C viruses by the following in vitro assays.

HCV Replicon Assay

DMEM media:

DMEM (Life Technologies #41965-039) was supplemented with 10% FBS, 2 mM L-glutamine (Life Technologies #25030-024), penicillin (100 units/ml)/streptomycin (100 micrograms/ml) (Life Technologies #15140-114), 1× non-essential amino acids (Life Technologies #11140-035).

Complete media was prepared by mixing FBS, DMEM media with Geneticin (G418). The compete media was pre-incubated at 37° C. in a CO$_2$ incubator. Then, HCV replicon-containing huh-7 cells (V. Lohmann et. al. Science, 285, (1999)110-113) was taken out from 37° C. incubator. The residual medium was absorbed, and the cells were washed with PBS. After washing fluid was removed, 1 ml 0.25% trypsin/0.02% EDTA solution. The cells were washed by the above trypsin/EDTA solution to make sure that each cell was cleaned. After the trypsin/EDTA solution was absorbed, the mixture was incubated at 37° C. in a CO2 incubator for 3-5 minutes. Morphological changes were observed by inverted microscope, till the cells were detached from the wall of container completely.

3 ml of complete media was added to make the cells to suspend. The cells are counted with hematometer. Appropriate volumes of the complete media was added to adjust the cell density to 100,000/ml. Cells were plated with 100 μl of suspension at 10,000/well of 96 well plate. Plates were placed into 37° C. 5% CO2 incubator for 24 h.

Preparation of Drug Solution:

Drugs were diluted under aseptic conditions.

Stock solutions may be prepared before the assay, which means that the test compounds are dissolved in 100% DMSO to afford a final concentration of 2 mM. Before the 96 well culture was completed, the stock solution was diluted with culter media to 100 fold of the final concentration (100× solution).

96-well plates were taken out from 37° C. CO$_2$ incubator and morphological changes were observed by inverted microscope. In a ventilator, 1 μl of 100× drug solution was added to wells of 96 well plate until the final concentration of DMSO in the mixture is 1%. The plates were incubated at 37° C. in a CO$_2$ environment for 48 h. 30 μl of Stead-G1® Luciferase Assay System (bought from Promega) was added to each well of 96 well plates and each plate is shaken in a plate shaker for 5 minutes to ensure cells cleavaged completely. The fluorescence signal was quantitated in a Perkin-Elmer plate reader (Envision) and integral time was setted to be 2 second. The following data were achieved after recording and analyzing the data.

The activity results of the compounds in the examples (EC 50 on replicon 1b) were listed in Table 1, wherein, A refers to an EC$_{50}$ of less than 10 nM; B refers to an EC$_{50}$ of 10 nM-50 nM; C refers to an EC$_{50}$ of 50 nM-500 nM; D refers to an EC$_{50}$ of 500 nM-20 uM; and E refers to an EC$_{50}$ of more than 20 uM.

| Compound | EC$_{50}$ | Compound | EC$_{50}$ | Compound | EC$_{50}$ |
|---|---|---|---|---|---|
| IIa-1 | A | IIa-2 | B | IIa-3 | C |
| IIa-4 | D | IIa-5 | C | IIa-6 | C |
| IIa-7 | C | IIa-8 | B | IIa-9 | B |
| IIa-10 | A | IIa-11 | A | IIa-12 | A |
| IIa-13 | B | IIa-14 | C | IIa-15 | A |
| IIa-16 | A | IIa-17 | A | IIa-18 | B |
| IIa-19 | A | IIa-20 | A | IIa-21 | B |
| IIa-22 | A | IIb-1 | A | IIb-2 | A |
| IIb-3 | A | IIb-4 | A | IIb-5 | B |
| IIb-6 | C | IIb-7 | D | MK7009 | A |

The results showed that the present invention provides a new kind of compounds with high anti-HCV potency.

MK7009 is a compound in the comparing reference WO2007/015787, having the following structure:

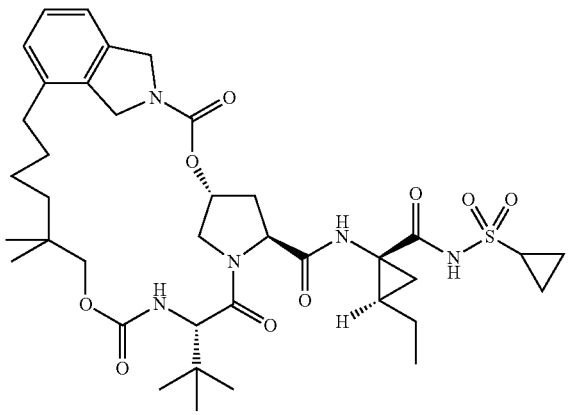 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1CN(C3)C(=O)O2)C(=O)NS(=O)(=O)C1CC1]

EXAMPLE 31

PK Assays

The following liver microsome metabolism assays validated the PK properties of compounds of Formula (I).

1. Buffer A: 1.0 L 0.1 M potassium phosphate monobasic buffer (including 1.0 mM EDTA); Buffer B: 1.0 L 0.1 M dipotassium phosphate buffer (including 1.0 mM EDTA); Buffer C: 0.1 M potassium phosphate buffer (including 1.0 mM EDTA), pH 7.4, add Buffer A to 700 ml of Buffer B until pH is 7.4.

2. Drug solution:
500 μM solution: a 10 μL (10 mM) DMSO was added to 190 μL ACN; 1.5 μM solution (dissolved in human microsome and the final concentration of microsome is 0.75 mg/mL): 1.5 μL (500 μM) of drug solution and 18.75 μL of human microsome (20 mg/mL) were added to 479.75 uL of Buffer C.

3. NADPH solution (6 mM, dissolved in Buffer C).

4. 30 L of drug solution (1.5 μM) was added to a 96-well plate, setting locations for different time points; Preincubated for 10 minutes at 37° C.

5. 15 L of NADPH (6 mM) was added to the location for 45-min time point; and timing started.

6. At 30, 15 and 5 min, 15 L of NADPH (6 mM) was added to each corresponding locations, respectively.

7. After the reaction was completed mins), 135 μL acetonitrile was added to the locations for all different time points; 15 L of NADPH (6 mM) was added to the location for 0 min time point.

8. Centrifugated at 3220 g for 10 min.

9. 50 μL of supernatant was collected and mixed with 50 μL, of ultrapure water. Samples were sent to LC/MS for analysis.

The results of compounds in Examples are listed in the following table:

| Compound | $t_{1/2}$ (min) |
| --- | --- |
| IIa-1 | 198 |
| IIa-16 | 193 |
| IIb-3 | 230 |
| MK7009 | 26 |

The results showed that the present invention provides a new kind of compounds with excellent PK properties, as anti-HCV inhibitors.

Examples of the present invention are only to illustrate the technical concept and features. Their purpose is to enable a person skilled in the art to understand and implement the contents according to the present invention, but not to limit the scope of the present invention. Within the spirit of the present invention, equivalent transformation or modification is also within the scope of protection.

The invention claimed is:

1. A compound of Formula (I) or a pharmaceutically acceptable salt, solvate, or prodrug thereof:

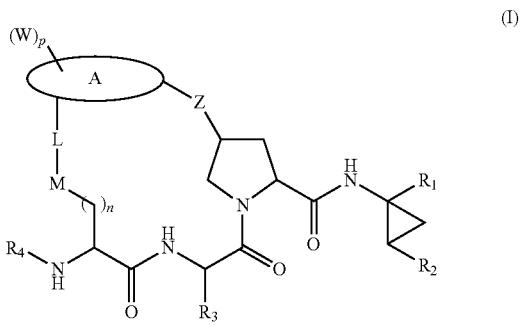

(I)

wherein,
$R_1$ is $-CO_2R_a$, $-CONR_bSO_2R_c$, $-CONR_dSO_2NR_eR_f$, or tetrazolyl;
$R_2$ is $C_1$-$C_6$ alkyl, $C_2$-$C_6$ alkenyl, or $C_3$-$C_8$ cycloalkyl, and said groups each are optionally substituted with 1-3 halo;
$R_3$ is $C_1$-$C_8$ alkyl, $C_3$-$C_8$ cycloalkyl, $C_1$-$C_8$ alkyl substituted with $C_3$-$C_8$ cycloalkyl, or $C_1$-$C_8$ alkyl or heteroalkyl substituted with aryl, and said groups each are optionally substituted with 1-3 halo;
$R_4$ is H, $C_1$-$C_6$ alkyl, $-SO_2R_c$, $-SO_2NR_dR_e$, $-CONR_fR_g$, $-COOR_h$, or $-COR_i$;
n is 1 or 2;
p is 0, 1 or 2;
M is $-O-$, $-S-$ or $-NH-$;
L is $C_1$-$C_6$ alkylene, $C_2$-$C_6$ alkenyl, or $C_2$-$C_6$ alkynyl;
W is halo, hydroxyl, $NO_2$, CN, $CF_3$, $OCF_3$, $-NR_aR_b$, $-SO_2R_c$, $-SOR_c$, $-SR_c$, $-SO_2NR_dR_e$, $-CONR_fR_g$, $-COOR_h$, $-NR_iCOR_j$, $-NR_kSO_2R_l$, $C_1$-$C_6$ alkyl, $-O-C_1$-$C_6$ alkyl, $C_3$-$C_7$ cycloalkyl, aryl, or heteroaryl;
Z is $C_1$-$C_6$ alkylene, $-O-$, $-O-C_1$-$C_5$ alkylene, $-C(O)O-$, $C_1$-$C_5$ alkylene-C(O)O—, $-C(O)NR_aR_b-$, or $C_1$-$C_5$ alkylene-C(O)NR$_a$R$_b-$;
ring A is a 8-14 membered fused bicyclic or tricyclic carbon structure, optionally substituted with 1-4 N, O, or S heteroatoms;
each $R_a$, $R_b$, $R_c$, $R_d$, $R_e$, $R_f$, $R_g$, $R_h$, $R_i$, $R_j$, $R_k$, $R_l$ is independently H, $C_1$-$C_6$ alkyl, $C_3$-$C_7$ cycloalkyl, $C_5$-$C_{10}$ aryl or heteroaryl, or $C_1$-$C_6$ alkylene $C_5$-$C_{10}$ aryl or heteroaryl.

2. The compound according to claim 1, wherein $R_1$ is $-CO_2R_a$, $-CONR_bSO_2R_c$, $-CONR_dSO_2NR_eR_f$, or tetrazolyl.

3. The compound according to claim 1, wherein $R_1$ is $-CONR_bSO_2R_c$.

4. The compound according to claim 1, wherein $R_4$ is $-COOR_h$.

5. The compound according to claim 1, having Formula (IIa):

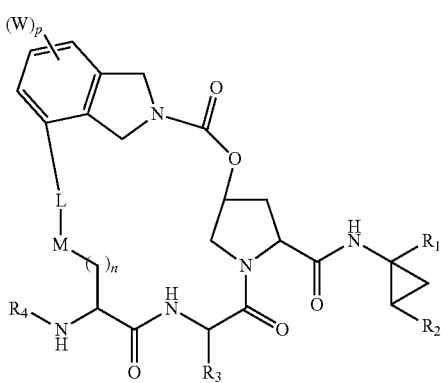

(IIa)

6. The compound according to claim 1, characterized in that $R_1$ is —$CONR_bSO_2R_c$ in Formula (IIa).

7. The compound according to claim 1, characterized in that $R_4$ is —$COOR_h$ in Formula (IIa).

8. The compound according to claim 1, having Formula (IIb):

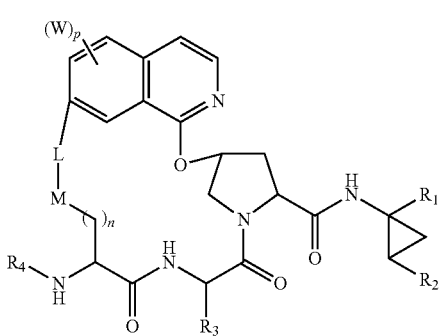

(IIb)

9. The compound according to claim 1, characterized in that $R_1$ is —$CONR_bSO_2R_c$ in Formula (IIb).

10. The compound according to claim 1, characterized in that $R_4$ is —$COOR_h$ in Formula (IIb).

11. The compound according to claim 1, characterized in that the compound is selected from:
tert-butyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;
(1R,12E,17S,20S,23S)-17-amino-20-tert-butyl-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide;
tert-butyl N-[(1R,12E,17R,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;
(1R,12E,17R,20S,23S)-17-amino-20-tert-butyl-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide;
(1R,12E,17S,20S,23S)-20-tert-butyl-23-N-[(1R,2S)-1-[(cyclopropanesulfonyl)carbamoyl]-2-ethenylcyclopropyl]-3,18,21-trioxo-17-C-pyrazine-2-2,15-dioxa-4,19,22-triazatetracyclo[20.2.1.1$^{4,7}$.0$^{6,11}$]hexacosa-6,8,10,12-tetraene-17,23-diamido;
(1R,12E,17R,20S,23S)-20-tert-butyl-23-N-[(1R,2S)-1-[(cyclopropanesulfonyl)carbamoyl]-2-ethenylcyclopropyl]-3,18,21-trioxo-17-C-pyrazine-2-2,15-dioxa-4,19,22-triazatetracyclo[20.2.1.1$^{4,7}$.0$^{6,11}$]hexacosa-6,8,10,12-tetraene-17,23-diamido;
(1R,12E,17S,20S,23S)-20-tert-butyl-N-[(1R,2S)-1-[(cyclopropanesulfonyl)carbamoyl]-2-ethenylcyclopropyl]-17-acetamido-3,18,21-trioxo-2,15-dioxa-4,19,22-triazatetracyclo[20.2.1.1$^{4,7}$.0$^{6,11}$]hexacosa-6,8,10,12-tetraene-23-carboxamide;
(1R,12E,17S,20S,23S)-20-tert-butyl-N-[(1R,2S)-1-[(cyclopropanesulfonyl)carbamoyl]-2-ethenylcyclopropyl]-17-methanesulfonamido-3,18,21-trioxo-2,15-dioxa-4,19,22-triazatetracyclo[20.2.1.1$^{4,7}$.0$^{6,11}$]hexacosa-6,8,10,12-tetraene-23-carboxamide;
ethyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.14$^{4,7}$.0$^{6,11}$]hexacosa-6,8,10,12-tetraen-17-yl]carbamate;
benzyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;
cyclopentyl N-[(1R,12E,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;
(1R,12E,17S,20S,23S)-20-tert-butyl-17-[(tert-butylcarbamoyl)amino]-N-[(1R,2S)-1-[(cyclopropanesulfonyl)carbamoyl]-2-ethenylcyclopropyl]-3,18,21-trioxo-2,15-dioxa-4,19,22-triazatetracyclo[20.2.1.1$^{4,7}$.0$^{6,11}$]hexacosa-6,8,10,12-tetraene-23-carboxamide;
tert-butyl N-[(1R,17S,20S,23S)-20-tert-butyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate;
tert-butyl N-[(1R,17S,20S,23S)-20-tert-butyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10-trien-17-yl]carbamate;
tert-butyl N-[(1R,12E,17S,20S,23S)-20-tert-butyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;
tert-butyl N-[(1R,12E,17S,20S,23S)-20-cyclohexyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;
tert-butyl N-[(1R,17S,20S,23S)-20-cyclohexyl-23-{[(1R,2S)-1-[(cyclopropanesulfonyl)carbamoyl]-2-ethenylcyclopropyl]carbamoyl}-3,18,21-trioxo-2,15-dioxa-4, 19,22-triazatetracyclo[20.2.1.1$^{4,7}$.0$^{6,11}$]hexacosa-6,8, 10-trien-17-yl]carbamate;

tert-butyl N-[(1R,17S,20S,23S)-20-cyclohexyl-23-{[(1R, 2R)-1-[(cyclopropanesulfonyl)carbamoyl]-2-ethylcyclopropyl]carbamoyl}-3,18,21-trioxo-2,15-dioxa-4,19, 22-triazatetracyclo[20.2.1.1$^{4,7}$.0$^{6,11}$]hexacosa-6,8,10-trien-17-yl]carbamate;

tert-butyl N-[(1R,12E,17S,20S,23S)-20-cyclohexyl-23-{[(1R,2R)-1-[(cyclopropanesulfonyl)carbamoyl]-2-ethylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;

tert-butyl N-[(1R,12E,18S,21S,24S)-21-cyclohexyl-24-{[(1R,2S)-1-[(cyclopropanesulfonyl)carbamoyl]-2-ethenylcyclopropyl]carbamoyl}-3,19,22-trioxo-2,15-dioxa-4,20,23-triazatetracyclo[21.2.1.1$^{4,7}$.0$^{6,11}$]heptacosa-6,8,10,12-tetraen-18-yl]carbamate;

tert-butyl N-[(1R,12E,17R,20S,23S)-20-tert-butyl-23-{[(1R,2S)-1-[(cyclopropanesulfonyl)carbamoyl]-2-ethenylcyclopropyl]carbamoyl}-3,18,21-trioxo-2-oxa-15-thia-4,19,22-triazatetracyclo[20.2.1.1$^{4,7}$.0$^{6,11}$]hexacosa-6,8,10,12-tetraen-17-yl]carbamate;

tert-butyl N-[(1R,12E,17S,20S,23S)-20-cyclopentyl-23-{[(1R,2S)-1-[(cyclopropanesulfonyl)carbamoyl]-2-ethenylcyclopropyl]carbamoyl}-3,18,21-trioxo-2,15-dioxa-4,19,22-triazatetracyclo[20.2.1.1$^{4,7}$.0$^{6,11}$]hexacosa-6,8,10,12-tetraen-17-yl]carbamate;

tert-butyl N-[(3R,5S,8S,11S,15E)-8-tert-butyl-5-{[(1R, 2S)-1-[(cyclopropanesulfonyl)carbamoyl]-2-ethenylcyclopropyl]carbamoyl}-18-methoxy-7,10-dioxo-2, 13-dioxa-6,9,23-triazatetracyclo[15.6.2.1$^{3,6}$.0$^{20,24}$] hexacosa-1(23),15,17(25),18,20(24),21-hexaen-11-yl] carbamate;

tert-butyl N-[(3R,5S,8S,11S)-8-tert-butyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$] hexacosa-1(23),17(25),18,20(24),21-pentaen-11-yl] carbamate;

tert-butyl N-[(3R,5S,8S,11S,15E)-8-cyclohexyl-5-{[(1R, 2S)-1-[(cyclopropanesulfonyl)carbamoyl]-2-ethenylcyclopropyl]carbamoyl}-18-methoxy-7,10-dioxo-2, 13-dioxa-6,9,23-triazatetracyclo[15.6.2.1$^{3,6}$.0$^{20,24}$] hexacosa-1(23),15,17(25),18,20(24),21-hexaen-11-yl] carbamate;

tert-butyl N-[(3R,5S,8S,11S)-8-cyclohexyl-5-{[(1R,2S)-1-[(cyclopropanesulfonyl)carbamoyl]-2-ethenylcyclopropyl]carbamoyl}-18-methoxy-7,10-dioxo-2,13-dioxa-6,9,23-triazatetracyclo[15.6.2.1$^{3,6}$.0$^{20,24}$] hexacosa-1(23),17(25),18,20(24),21-pentaen-11-yl] carbamate;

tert-butyl N-[(3R,5S,8S,11S,15E)-8-cyclohexyl-5-{[(1R, 2R)-1-[(cyclopropanesulfonyl)carbamoyl]-2-ethylcyclopropyl]carbamoyl}-18-methoxy-7,10-dioxo-2,13-dioxa-6,9,23-triazatetracyclo[15.6.2.1$^{3,6}$.0$^{20,24}$] hexacosa-1(23),15,17(25),18,20(24),21-hexaen-11-yl] carbamate;

tert-butyl N-[(3R,5S,8S,11S)-8-cyclohexyl-5-{[(1R,2S)-1-[(cyclopropanesulfonyl)carbamoyl]-2-ethylcyclopropyl]carbamoyl}-18-methoxy-7,10-dioxo-2,13-dioxa-6, 9,23-triazatetracyclo[15.6.2.1$^{3,6}$.0$^{20,24}$]hexacosa-1 (23),17(25),18,20(24),21-pentaen-11-yl]carbamate;

tert-butyl N-[(3R,5S,8S,11S,15E)-8-cyclohexyl-5-{[(1R, 2S)-1-hydroxycarbonyl-2-ethenylcyclopropyl]carbamoyl}-18-methoxy-7,10-dioxo-2,13-dioxa-6,9,23-triazatetracyclo[15.6.2.13,6.020,24]hexacosa-1(23),15,17 (25),18,20(24),21-hexaen-11-yl]carbamate.

12. A pharmaceutical composition characterized in that said composition comprises a pharmaceutically acceptable carrier and a compound of claim 1 or a pharmaceutically acceptable salt, solvate, or prodrug thereof.

13. The pharmaceutical composition according to claim 12, characterized in that said pharmaceutical composition further comprises a second therapeutic agent, and said second therapeutic agent is an HCV antiviral agent, an immunomodulator, or an anti-infective agent.

14. The pharmaceutical composition according to claim 13, characterized in that the HCV antiviral agent is an HCV protease inhibitor or an HCV NS5B polymerase inhibitor.

15. The pharmaceutical composition according to claim 12, wherein the pharmaceutical composition is in the form of an aqueous dispersion, a liquid, a gel, a syrup, an elixir, a slurry, a suspension, a spray, a controlled-release formulation, a delayed-release preparations, a sustained-release formulation, an immediate-release agent, an instantizing agent, an effervescing agent, or a powder; or the pharmaceutical composition is in the form of pulse-release tablets, microgranules, tablets, pills, dragees, or capsules.

16. A method for treatment of infection by HCV, comprising administering to a subject in need thereof a therapeutically effective amount of a compound of claim 1.

17. The method according to claim 16, characterized in that the method further comprises administering a second therapeutic agent selected from the group consisting of an HCV antiviral agent, an immunomodulator, and an anti-infective agent.

18. The method according to claim 17, characterized in that the HCV antiviral agent is an HCV protease inhibitor or an HCV NS5B polymerase inhibitor.

19. The pharmaceutical composition according to claim 12, wherein the pharmaceutical composition is in a lyophilized form.

* * * * *

UNITED STATES PATENT AND TRADEMARK OFFICE
CERTIFICATE OF CORRECTION

PATENT NO. : 9,321,809 B2  
APPLICATION NO. : 14/375418  
DATED : April 26, 2016  
INVENTOR(S) : Ben Li et al.

Page 1 of 1

It is certified that error appears in the above-identified patent and that said Letters Patent is hereby corrected as shown below:

In the Claims

In Column 72, Claim 1, Lines 53-54, "–C(O)NR$_a$R$_r$–" should read "–C(O)NR$_a$R$_b$–."

Signed and Sealed this  
Twenty-first Day of June, 2016

Michelle K. Lee  
*Director of the United States Patent and Trademark Office*